(12) United States Patent
Guenther et al.

(10) Patent No.: US 11,136,295 B2
(45) Date of Patent: Oct. 5, 2021

(54) D-AMPHETAMINE COMPOUNDS, COMPOSITIONS, AND PROCESSES FOR MAKING AND USING THE SAME

(71) Applicant: KemPharm, Inc., Celebration, FL (US)

(72) Inventors: Sven Guenther, Coralville, IA (US); Guochen Chi, Coralville, IA (US); Travis Mickle, Kissimme, FL (US)

(73) Assignee: KEMPHARM, INC., Celebration, FL (US)

( * ) Notice: Subject to any disclaimer, the term of this patent is extended or adjusted under 35 U.S.C. 154(b) by 80 days.

(21) Appl. No.: 16/667,804

(22) Filed: Oct. 29, 2019

(65) Prior Publication Data

US 2020/0131130 A1    Apr. 30, 2020

Related U.S. Application Data

(60) Provisional application No. 62/800,494, filed on Feb. 2, 2019, provisional application No. 62/752,324, filed on Oct. 29, 2018.

(51) Int. Cl.

| | | |
|---|---|---|
| *C07D 213/56* | (2006.01) | |
| *A61K 31/4425* | (2006.01) | |
| *C07D 213/79* | (2006.01) | |
| *C07D 213/81* | (2006.01) | |
| *C07D 413/06* | (2006.01) | |
| *A61K 31/4458* | (2006.01) | |
| *C07D 401/06* | (2006.01) | |
| *A61K 47/55* | (2017.01) | |
| *A61K 9/00* | (2006.01) | |
| *A61K 31/4545* | (2006.01) | |
| *C07D 213/80* | (2006.01) | |
| *A61K 9/02* | (2006.01) | |

(52) U.S. Cl.
CPC .......... *C07D 213/79* (2013.01); *A61K 9/0019* (2013.01); *A61K 9/0043* (2013.01); *A61K 31/4458* (2013.01); *A61K 31/4545* (2013.01); *A61K 47/55* (2017.08); *C07D 213/80* (2013.01); *C07D 213/81* (2013.01); *C07D 401/06* (2013.01); *C07D 413/06* (2013.01); *A61K 9/0053* (2013.01); *A61K 9/02* (2013.01)

(58) Field of Classification Search
CPC ................ C07D 213/56; C07D 213/55; A61K 31/4425; A61K 31/4409; A61K 31/4402; A61P 25/26
USPC .................................. 546/323, 326; 514/354
See application file for complete search history.

(56) References Cited

U.S. PATENT DOCUMENTS

| | | | |
|---|---|---|---|
| 9,556,156 B2 * | 1/2017 | Dugar | ..................... A61P 23/00 |
| 2009/0186828 A1 | 7/2009 | Mickle | |
| 2010/0303903 A1 | 12/2010 | Hackett | |
| 2019/0142815 A1 | 5/2019 | Guenther | |
| 2019/0284166 A1 | 9/2019 | Mickle et al. | |

OTHER PUBLICATIONS

International Search Report and Written Opinion regarding PCT Application No. PCT/US2020/019140, dated May 26, 2020, 13 pages.
Braeckman, R, et al., Single-dose Pharmacokinetics of KP415, an Investigational Product Containing the Prodrug Serdexmethylphenidate (SDX), in Children and Adolescents with ADHD; American Professional Society of ADHD and Related Disorders Poster, Washington, D.C., dated Jan. 20, 2019.
International Search Report and Written Opinion regarding PCT Application No. PCT/US2020/019146, dated Jun. 8, 2020, 13 pages.

* cited by examiner

*Primary Examiner* — Charanjit Aulakh
(74) *Attorney, Agent, or Firm* — McAndrews Held & Malloy, Ltd.

(57) ABSTRACT

Disclosed are d-amphetamine compounds and compositions comprising at least one organic acid covalently bound to d-amphetamine, a salt thereof, a derivative thereof, or a combination thereof. Methods of making and using the same are also disclosed.

38 Claims, 40 Drawing Sheets

D-AMPHETAMINE COMPOUNDS, COMPOSITIONS, AND PROCESSES FOR MAKING AND USING THE SAME

RELATED APPLICATIONS

The present patent application is related to and claims the priority benefit of U.S. Provisional Patent Application Ser. No. 62/800,494, filed Feb. 2, 2019 and U.S. Provisional Patent Application Ser. No. 62/752,324, filed Oct. 29, 2018 the content of which is hereby incorporated by reference in its entirety into this disclosure.

FEDERALLY SPONSORED RESEARCH OR DEVELOPMENT

[Not Applicable]

BACKGROUND OF THE INVENTION

The presently described technology relates to novel compounds and compositions of d-amphetamine (i.e., 1-phenyl-propan-2-amine), including organic compounds covalently bonded or attached to d-amphetamine, salts thereof, derivatives thereof, or combinations thereof. Methods of making and using the compounds and compositions of the present technology are also disclosed.

Stimulants, including d-amphetamine and its derivatives, enhance the activity of the sympathetic nervous system and/or central nervous system (CNS) and are prescribed for the treatment of a range of conditions and disorders predominantly encompassing, for example, attention deficit hyperactivity disorder (ADHD), attention deficit disorder (ADD), obesity, narcolepsy, appetite suppression, depression, anxiety, and wakefulness.

Attention deficit hyperactivity disorder (ADHD) in children has been treated with stimulants for many years. However, more recently, the increase in a number of prescriptions for ADHD therapy in the adult population has, at times, outperformed the growth of the pediatric market. Although there are various drugs currently in use for the treatment of ADHD, such as methylphenidate (commercially available from, for example, Novartis International AG (located in Basel, Switzerland) under the trademark Ritalin®) and non-stimulant atomoxetine (commercially from Eli Lilly and Company (located in Indianapolis, Ind.) as Strattera®), d-amphetamine has been the forerunner in ADHD therapy.

Initial drug therapy for ADHD was limited to fast-acting immediate release formulations of stimulants (e.g., Dexedrine®, pure dextroamphetamine sulfate, commercially available from Smith Kline and French located in the United Kingdom) which triggered an array of potentially undesirable side effects including, for example, fast wear-off of the therapeutic effect of the stimulant active ingredient causing rebound symptoms, cardiovascular stress/disorders (e.g., increased heart rate, hypertension, cardiomyopathy), other side effects (e.g., insomnia, euphoria, psychotic episodes), addiction and abuse.

Behavioral deterioration (rebound/"crashing") is observed in a significant portion of children with ADHD as the medication wears off, typically in the afternoon or early evening. Rebound symptoms include, for example, irritability, crankiness, hyperactivity worse than in the unmediated state, sadness, crying and in rare cases psychotic episodes. The symptoms may subside quickly or last several hours. Some patients may experience rebound/crashing so severe that treatment must be discontinued. Rebound/crashing effects can also give rise to addictive behavior by enticing patients to administer additional doses of stimulant with the intent to prevent anticipated rebound/crashing negative outcomes and side effects.

Stimulants, such as methylphenidate and d-amphetamine, have been shown to exhibit noradrenergic and dopaminergic effects that can lead to cardiovascular events comprising, for example, increased heart rate, hypertension, palpitations, tachycardia and in isolated cases cardiomyopathy, stroke, myocardial infarction, and sudden death. Consequently, currently available stimulants expose patients with pre-existing structural cardiac abnormalities or other severe cardiac indications to even greater health risks and are frequently not used or used with caution in this population. It is notable, however that the cardiovascular effects of stimulants, for example on heart rate and blood pressure, are dependent on the administered dose. As a result, a treatment which maintains the lowest effective stimulant blood concentrations for a therapeutically beneficial duration is believed to demonstrate fewer cardiovascular risks.

D-amphetamine and many of its derivatives (e.g., methamphetamine, 3,4-methylenedioxy-methamphetamine/"ecstasy") are widely abused for various purposes such as euphoria, extended periods of alertness/wakefulness, or rapid weight loss or by actual ADHD patients who developed excessive self-dosing habits to prevent rebound symptoms from manifesting, for example, in anxiety or depression. The effects desired by potential abusers originated from the stimulation of the central nervous system and prompted a Schedule II or even Schedule I classification for d-amphetamine (d- and l-d-amphetamine individually and any combination of both are Schedule II) and certain derivatives thereof after the passage of the Controlled Substance Act (CSA) in 1970. Both classifications are defined by the high propensity for abuse. Schedule II drugs have an accepted medical use while Schedule I substances do not fall under the CSA. So far, all d-amphetamine products, including compositions with sustained release formulations thereof, are obligated to include a black box warning on the drug label to inform patients about the potential for d-amphetamine abuse and dependence.

It has been shown in the conventional art that most side effects of amphetamines are caused by a large initial spike in blood concentration of the stimulant which quickly erodes to levels below therapeutic effectiveness (typically within 4-6 hours). As a consequence, the high potency of dextroamphetamine (d-amphetamine) was subsequently modulated by a series of new drugs with increasingly sustained release profiles achieved by delivering d-amphetamine more slowly into the bloodstream with the goal to create safer and less abusable treatment outcomes and regimens. The methods and technologies for generating smaller spikes in drug blood concentrations include, for example, use of mixed salts and isomer compositions (i.e., different salts of d- and less potent l-amphetamine), extended/controlled/sustained release formulations of amphetamine/dextroamphetamine salts (e.g., Adderall XR® commercially available from Shire U.S., Inc. located in Wayne, Pa.) and prodrugs of lisdexamfetamine salts (Vyvanse® also commercially available from Shire).

As a result, there still exists a need within the art for a safer dosage form of d-amphetamine and treatment regimen that is therapeutically effective and can provide sustained release and sustained therapeutic effect.

BRIEF SUMMARY OF THE INVENTION

The presently described technology provides, in part, novel compounds, and compositions of the stimulant d-amphetamine ("d-Amp", "dextroamphetamine"), salts thereof, other derivatives thereof, and combinations thereof.

In some aspects, the present technology provides compounds and/or compositions comprising d-amphetamine and one or more organic compounds. In some aspects of the present technology, the organic compound comprises a heterocyclic nitrogen compound. Heterocyclic nitrogen compounds are commonly found in nature and are involved in several biological functions in plants and animals. Examples of heterocyclic nitrogen compounds for use in the practice of the present technology include, but are not limited to, for example, pyridine derivatives, some of which play an important role in the nicotinate and tryptophan metabolism. In these compounds, one carbon of the phenyl ring is commonly replaced by a nitrogen atom.

In some aspects of the present technology, the organic compound comprises an amino acid. Amino acids are organic compounds containing both a carboxyl (—COOH) and amino (—NH$_2$) group, and a variable side chain group. Amino acids that may be used in the present technology can be natural, standard, non-standard, synthetic, and/or essential amino acids, and can be an L-amino acid or a D-amino acid, or a combination thereof. Examples of amino acids for use in the practice of the present technology include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, norleucine, 3-nitrotyrosine, pyroglutamic acid, nitroarginine, ornithine, homoarginine, citrulline, homocitrulline, homoserine, theanine, γ-aminobutyric acid, 6-aminohexanoic acid, sarcosine, carnitine, 2-aminoadipic acid, pantothenic acid, taurine, hypotaurine, lanthionine, thiocysteine, cystathionine, homocysteine, β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), 2-aminoisobutyric acid, isovaline, di-N-ethylglycine, N-methyl-alanine, L-abrine, 4-hydroxyproline, 5-hydroxylysine, 3-hydroxyleucine, 4-hydroxyisoleucine, 5-hydroxy-L-tryptophan, 1-aminocyclopropyl-1-carboxylic acid, azetidine-2-carboxylic acid, pipecolic acid, allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino-propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, 4-(dimethylamino)cinnamic acid, 2-pyridylalanine (2-Pal), and 3-pyridylalanine (3-Pal).

In some aspects, the compound has the structure of Formula IA

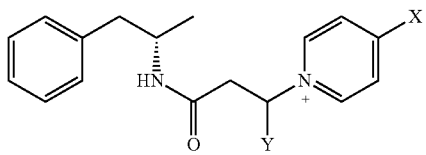

Formula IA where X is A-COO—R;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula IC

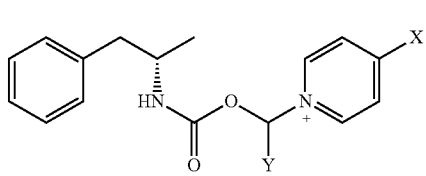

Formula IC where X is A-CO—NR$^1$R$^2$;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

It should be appreciated that the carbon atom attached to Y is a chiral center if Y is not hydrogen. It should further be appreciated that in certain aspects, X is attached to at least one of C-2, C-3, C-4, C-5 and/or C-6.

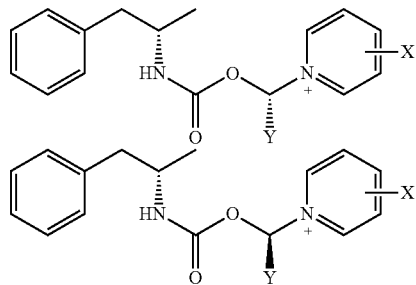

In some aspects, the present technology comprises conjugates where this chiral carbon has an R configuration. In other aspects, the present technology comprises conjugates where this chiral carbon has an S configuration. In further aspects, the present technology comprises a mixture of stereoisomers where some conjugates contain a chiral carbon having an R configuration and some conjugates contain a chiral carbon having an S configuration.

The presently described technology further provides methods of controlled therapeutic delivery of d-amphetamine compositions by oral administration. In at least one aspect, the presently described technology is focused on a slow/sustained controlled release composition of d-amphetamine, in compound form, that allows slow/sustained/controlled delivery of the stimulant into the blood system of a human or animal within a therapeutic window upon oral administration. At least some compositions/formulations of the current technology can lessen the rebound effect, cardiovascular stress, addiction/abuse potential and/or other common stimulant side effects associated with d-amphetamine and similar compounds. Such compositions may also increase the duration of therapeutic efficacy, ease of application, patient compliance and/or any combination of these characteristics when administered, in particular, orally.

The release of d-amphetamine following oral administration of the compounds of the present technology can occur gradually over an extended period of time thereby eliminating unintended excessive rapid elevations (e.g., large blood level concentration spikes) of drug levels in the bloodstream of a human or animal patient. Not wanting to be bound by any particular theory, it is also believed that such spikes in blood levels can lead to a euphoric drug "high" and cardiovascular effects like increased blood pressure and heart rate. Additionally, sustained blood levels are achieved within an effective therapeutic range for a longer duration than other conventional therapies, thereby preventing a rebound effect.

In some embodiments, the present technology provides particular d-amphetamine ("d-Amp", "dexamphetamine") compounds, compositions, or pharmaceutically acceptable salts thereof, to provide, for example, at least one single daily dose form of a d-amphetamine compound in a composition with unconjugated d-amphetamine that can provide both immediate and extended release PK profiles when compared to unconjugated d-amphetamine. The release profile in some instances provides the ability of the compound or composition to be administered using dosing regimens that are not easily utilized with the unconjugated d-amphetamine.

At least some compositions comprising the d-amphetamine compounds of the present technology are resistant to abuse by parenteral routes of administration, such as intravenous "shooting," intranasal "snorting," or inhalation "smoking," that are often employed during illicit use. The present technology thus provides a stimulant based treatment modality and dosage form for certain disorders requiring the stimulation of the CNS such as ADHD, ADD, obesity, narcolepsy, appetite suppressant, depression, anxiety, sleep disorders, excessive daytime sleepiness, insomnia, binge eating, and wakefulness with reduced or prevented abuse potential. Although not wanting to be bound by any particular theory, it is believed that compositions of the present technology result in substantially decreased abuse potential or abuse liability as compared to existing stimulant treatment modalities and dosage forms.

At least some compositions comprising the d-amphetamine compound of the present technology can also be used for treating stimulant (cocaine, methamphetamine) abuse and addiction, substance use disorder, improving battlefield alertness, and/or for combating fatigue.

The compositions of the present technology preferably have no or a substantially decreased pharmacological activity when administered through injection or intranasal routes of administration. However, they remain orally bioavailable with respect to d-amphetamine. The bioavailability can be a result of the hydrolysis of the covalent linkage between d-amphetamine and the remaining portion of the conjugate following oral administration. Hydrolysis is time-dependent, thereby allowing d-amphetamine and other metabolites such as p-hydroxyamphetamine and p-hydroxyephedrine to become available in its active form over an extended period of time. In at least one further aspect, release of d-amphetamine is diminished when compared to unconjugated d-amphetamine or eliminated when the composition of the present technology is delivered by parenteral routes.

For example, in one aspect, the composition of the present technology maintains its effectiveness and abuse resistance following the crushing of the tablet, capsule or other oral dosage form utilized to deliver the therapeutic component (i.e., active ingredient/drug) due to the controlled release components being a designed property of the composition, not the formulation. In contrast, conventional extended release formulations used to control the release of d-amphetamine are subject to release of up to the entire d-amphetamine content immediately following crushing. When the content of the crushed tablet is injected or snorted, the large dose of d-amphetamine produces the "rush" effect sought by addicts.

Other objects, advantages, and aspects of the invention are described below and will be obvious from this description and practice of the invention.

DETAILED DESCRIPTION OF THE INVENTION

Figure 1:
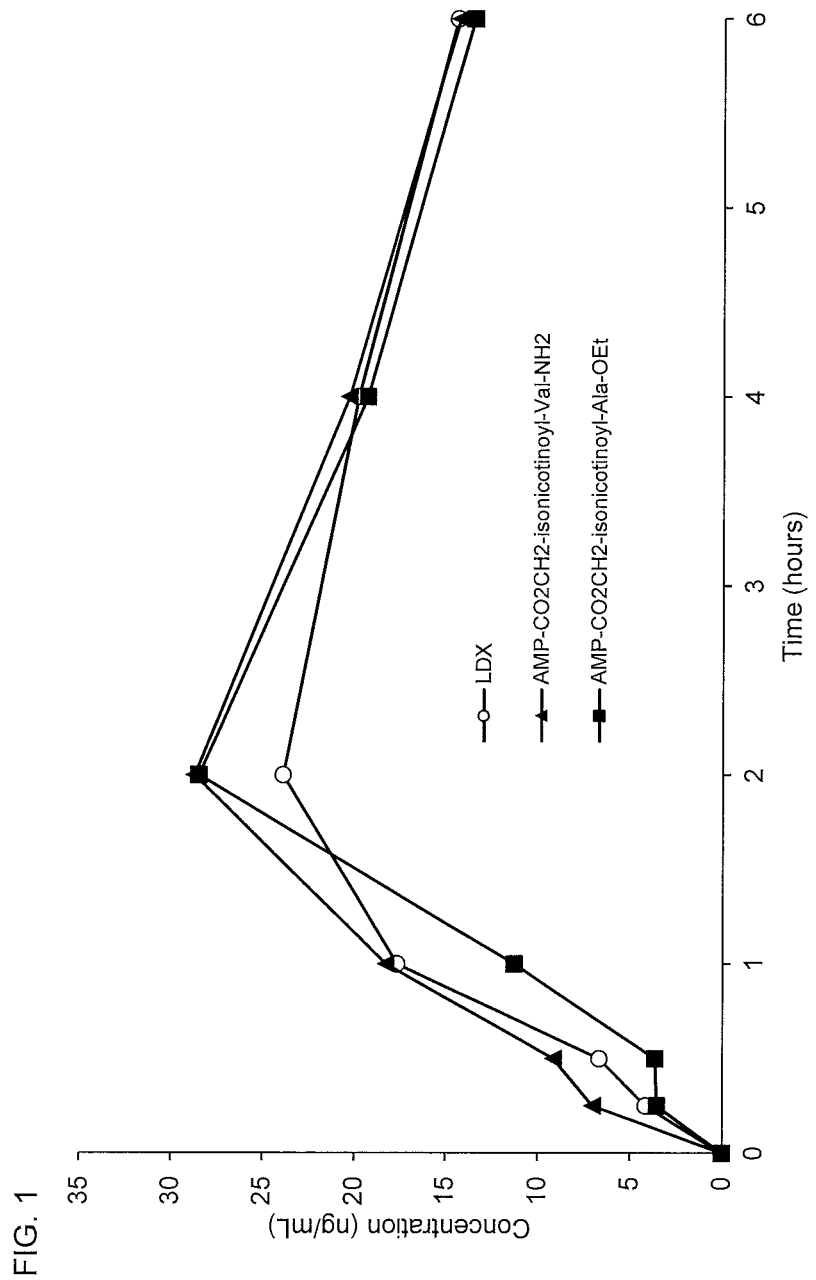
FIG. 1. Oral PK curves comparing lisdexamfetamine (LDX), d-amphetamine-$CO_2CH_2$-isonicotinoyl-valinamide (AMP-$CO_2CH_2$-isonicotinoyl-Val-$NH_2$), and d-amphetamine-$CO_2CH_2$-isonicotinoyl-ethyl alanine ethyl ester (AMP-$CO_2CH_2$-isonicotinoyl-Ala-OEt).
Figure 2:
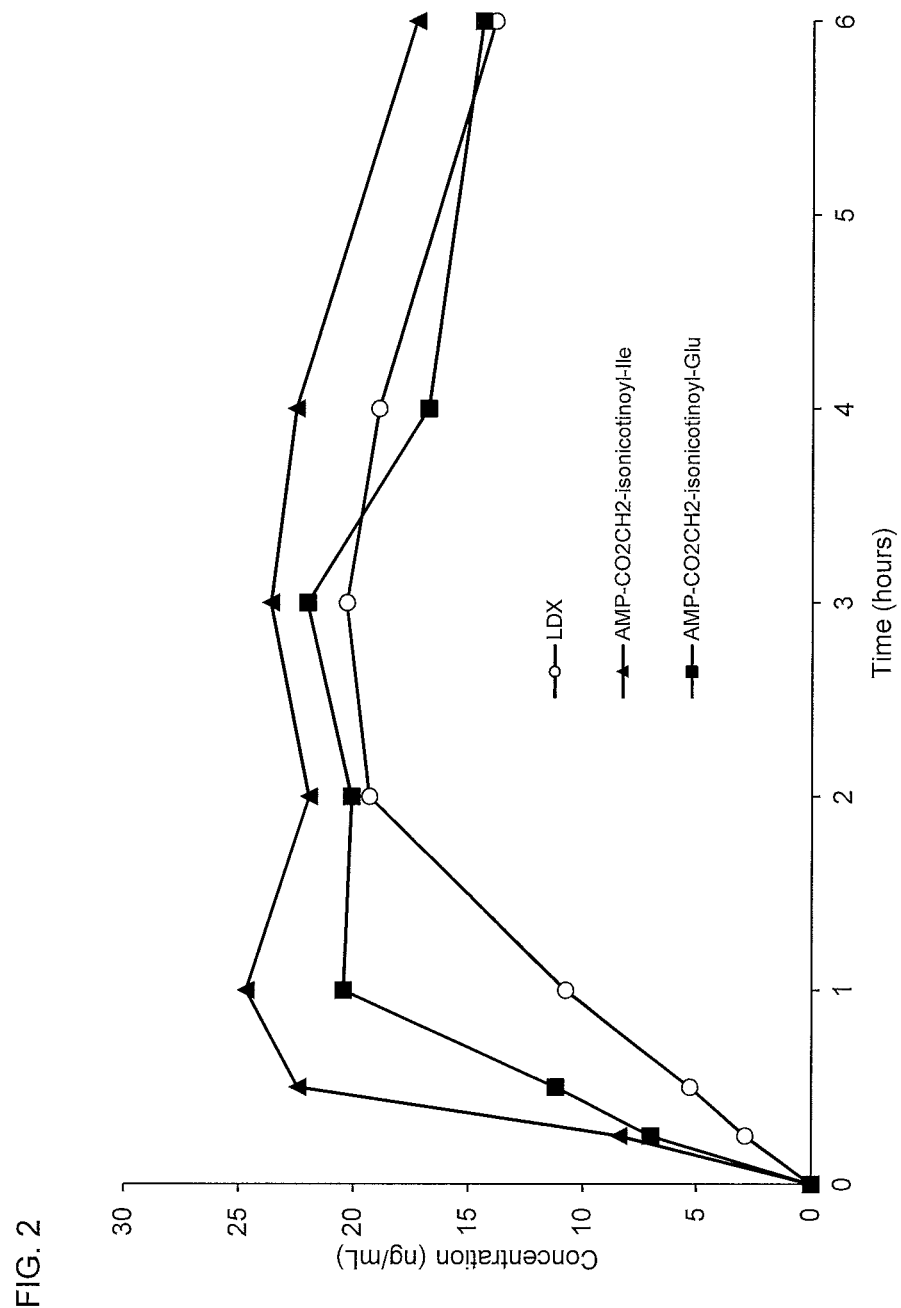
FIG. 2. Oral PK curves comparing lisdexamfetamine (LDX), d-amphetamine-$CO_2CH_2$-isonicotinoyl-isoleucine (AMP-$CO_2CH_2$-isonicotinoyl-Ile), and d-amphetamine-$CO_2CH_2$-isonicotinoyl-glutamate (AMP-$CO_2CH_2$-isonicotinoyl-Glu).
Figure 3:
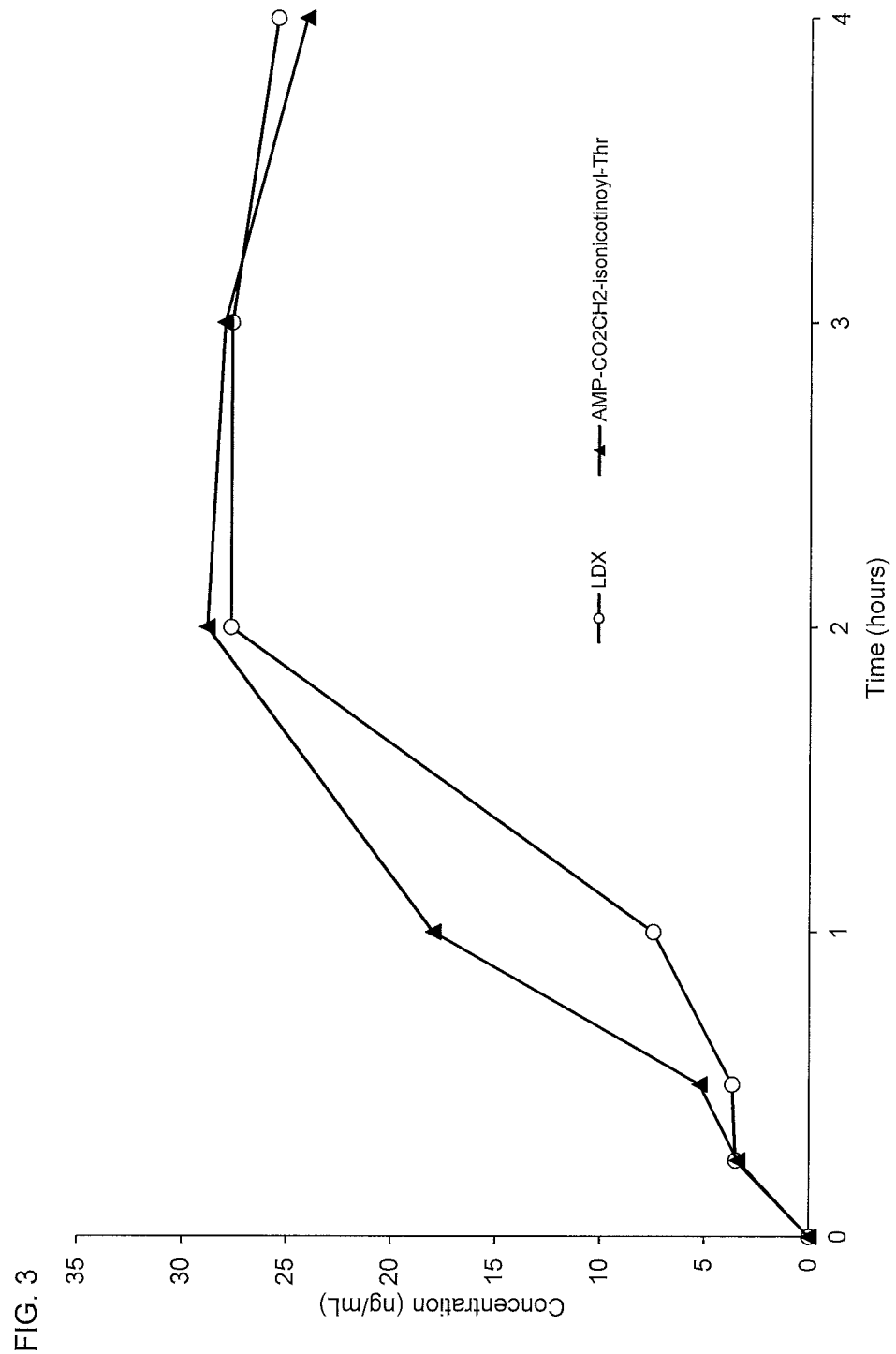
FIG. 3. Oral PK curves comparing lisdexamfetamine (LDX) and d-amphetamine-$CO_2CH_2$-isonicotinoyl-threonine (AMP-$CO_2CH_2$-isonicotinoyl-Thr).
Figure 4:
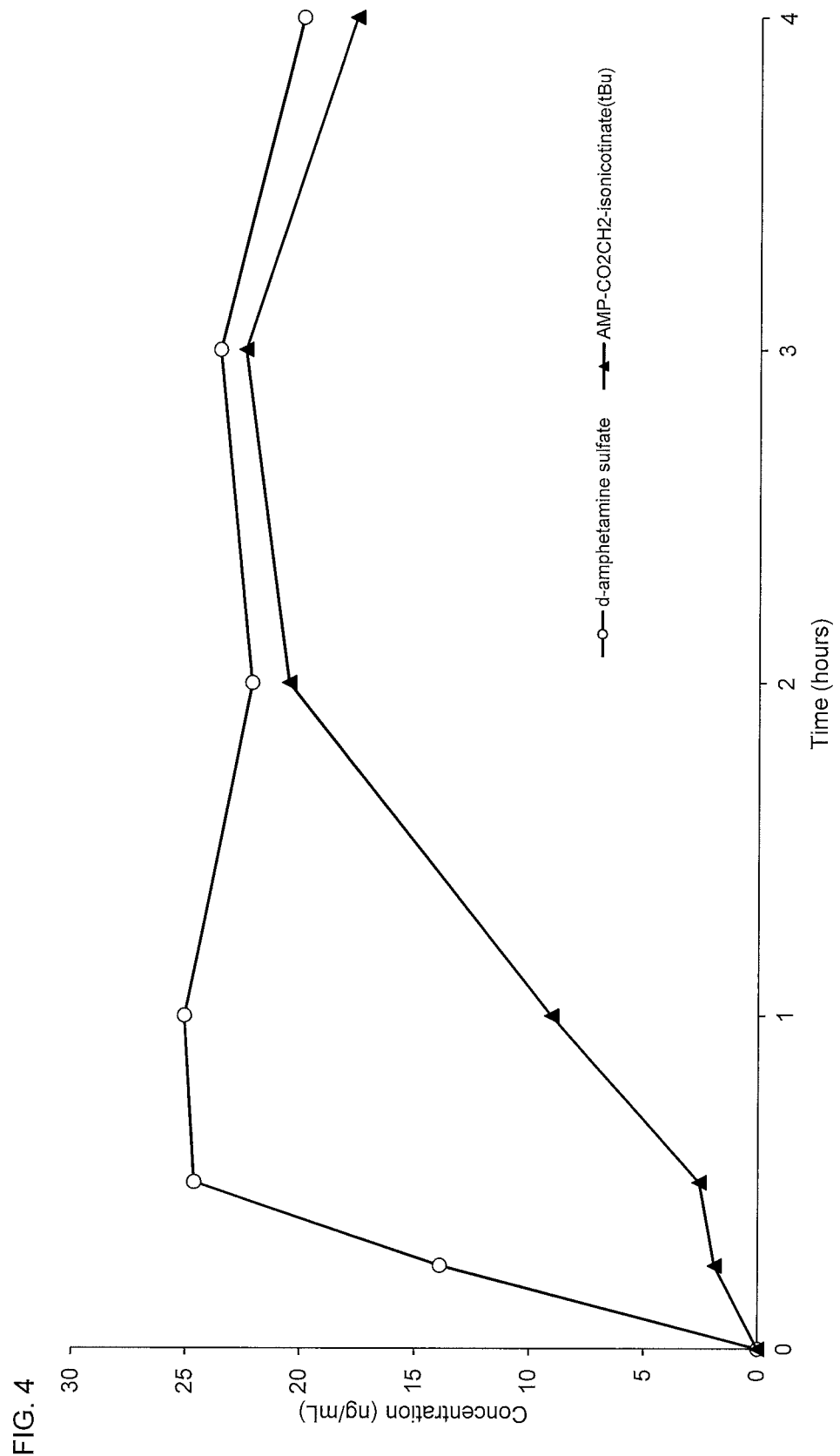
FIG. 4. Oral PK curves comparing d-amphetamine sulfate and d-amphetamine-$CO_2CH_2$-isonicotinate-tert-butyl ester (AMP-$CO_2CH_2$-isonicotinate(tBu)).
Figure 5:
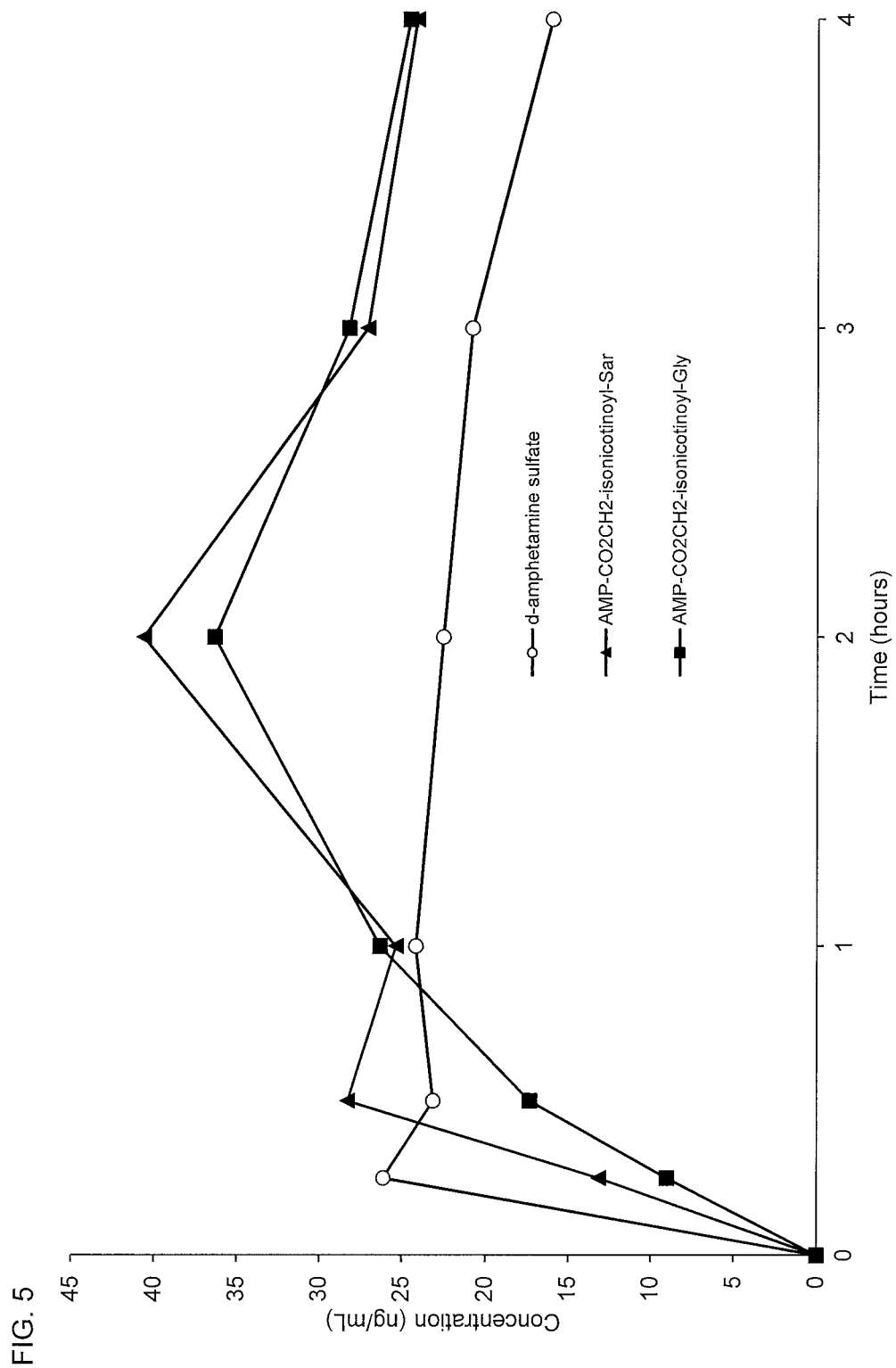
FIG. 5. Oral PK curves comparing d-amphetamine sulfate, d-amphetamine-$CO_2CH_2$-isonicotinoyl-sarcosine (AMP-$CO_2CH_2$-isonicotinoyl-Sar), and d-amphetamine-$CO_2CH_2$-isonicotinoyl-glycine (AMP-$CO_2CH_2$-isonicotinoyl-Gly).
Figure 6:
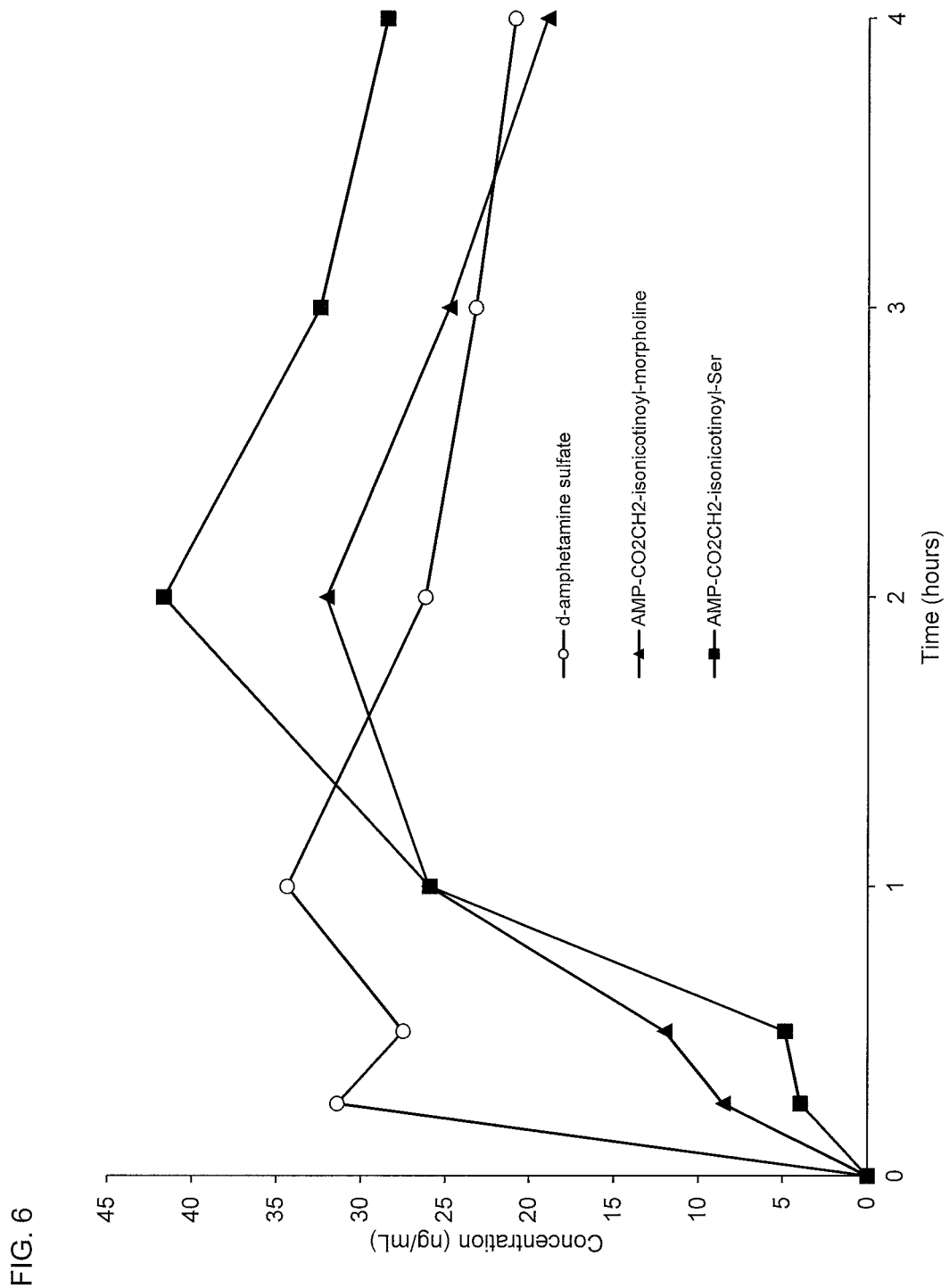
FIG. 6. Oral PK curves comparing d-amphetamine sulfate, d-amphetamine-$CO_2CH_2$-isonicotinoyl-morpholine (AMP-$CO_2CH_2$-isonicotinoyl-morpholine), and d-amphetamine-$CO_2CH_2$-isonicotinoyl-serine (AMP-$CO_2CH_2$-isonicotinoyl-Ser).
Figure 7:
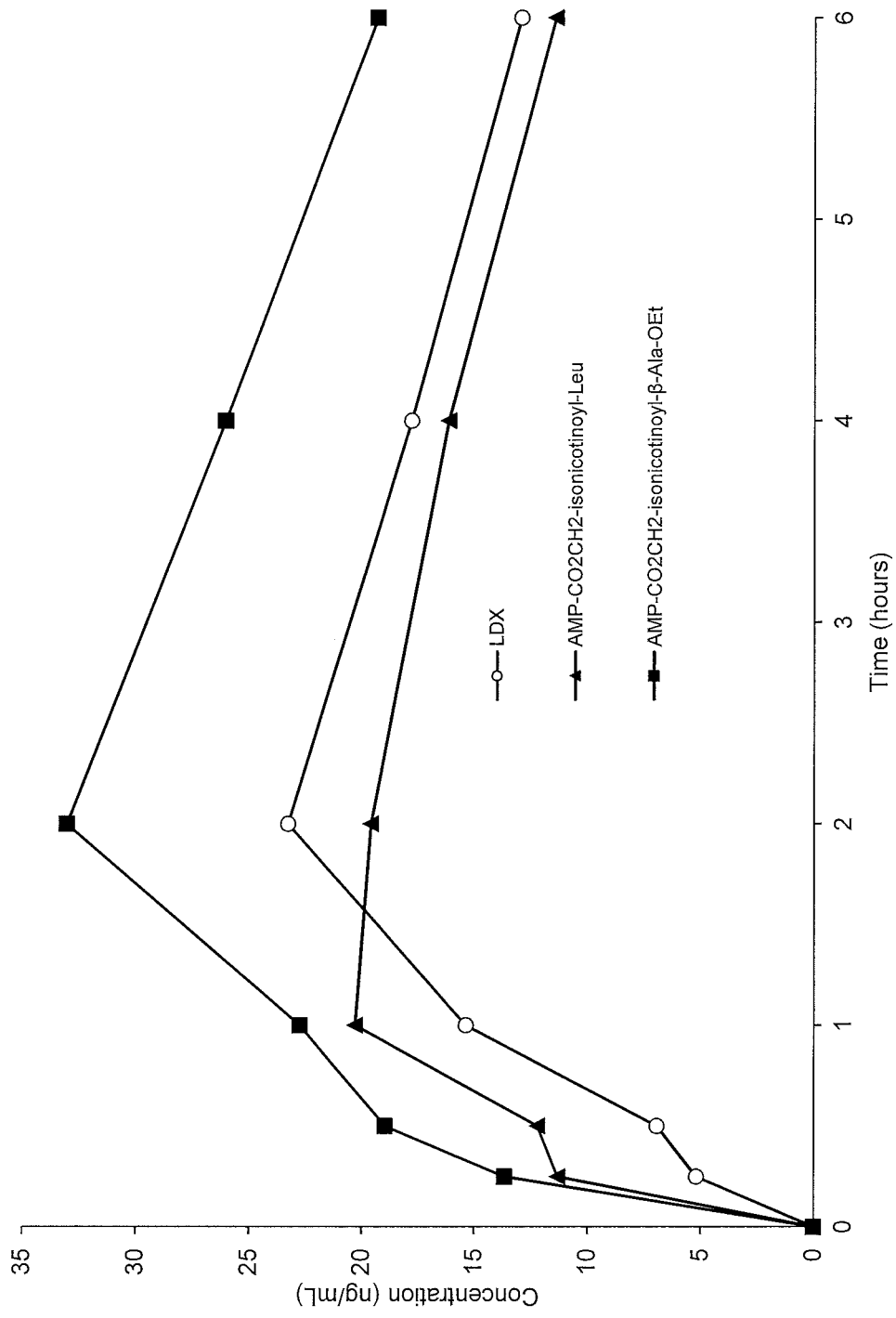
FIG. 7. Oral PK curves comparing lisdexamfetamine (LDX), d-amphetamine-$CO_2CH_2$-isonicotinoyl-leucine (AMP-$CO_2CH_2$-isonicotinoyl-Leu), and d-amphetamine-$CO_2CH_2$-isonicotinoyl-beta-alanine ethyl ester (AMP-$CO_2CH_2$-isonicotinoyl-β-Ala-OEt).
Figure 8:
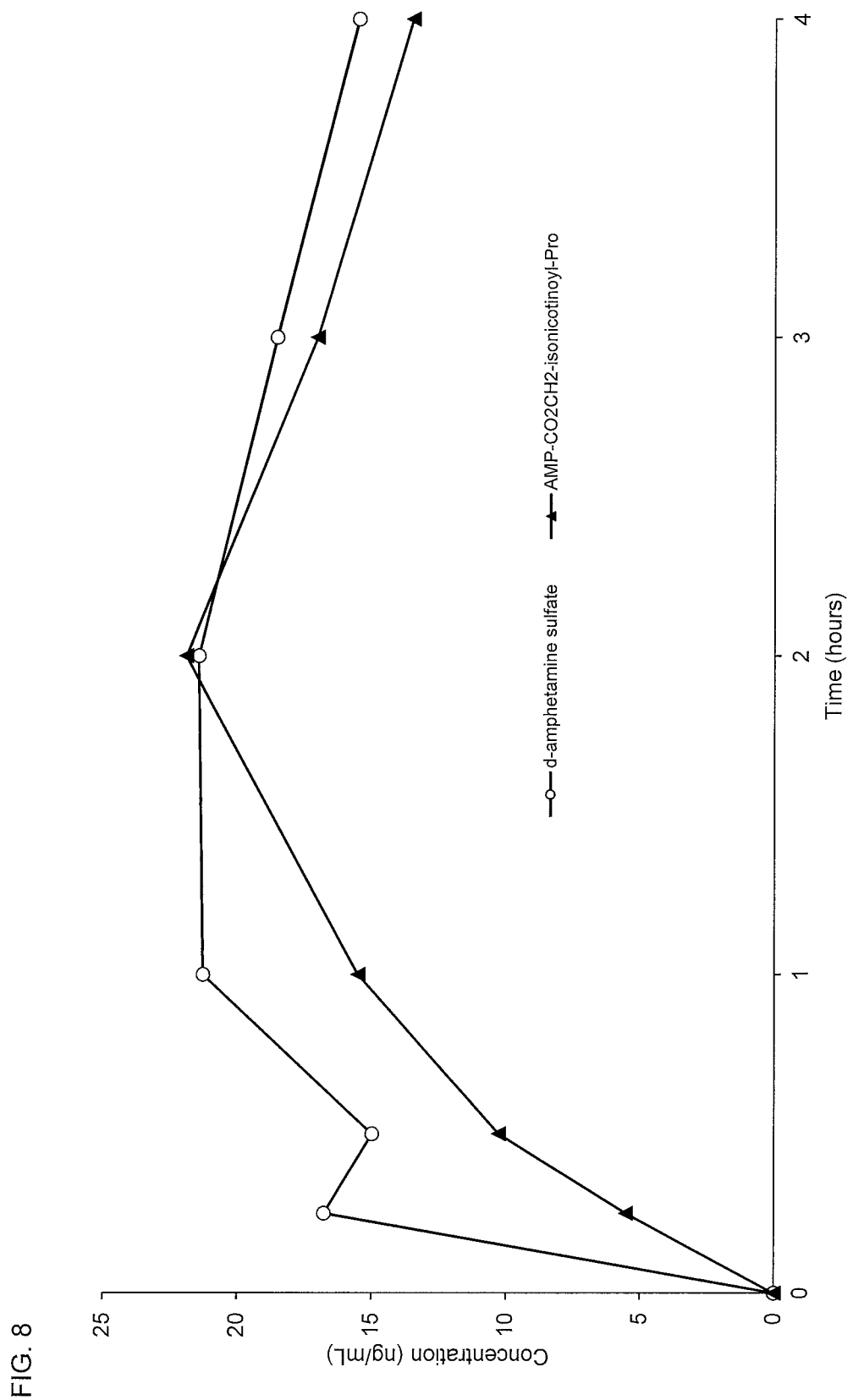
FIG. 8. Oral PK curves comparing d-amphetamine sulfate and d-amphetamine-$CO_2CH_2$-isonicotinoyl-proline (AMP-$CO_2CH_2$-isonicotinoyl-Pro).
Figure 9:
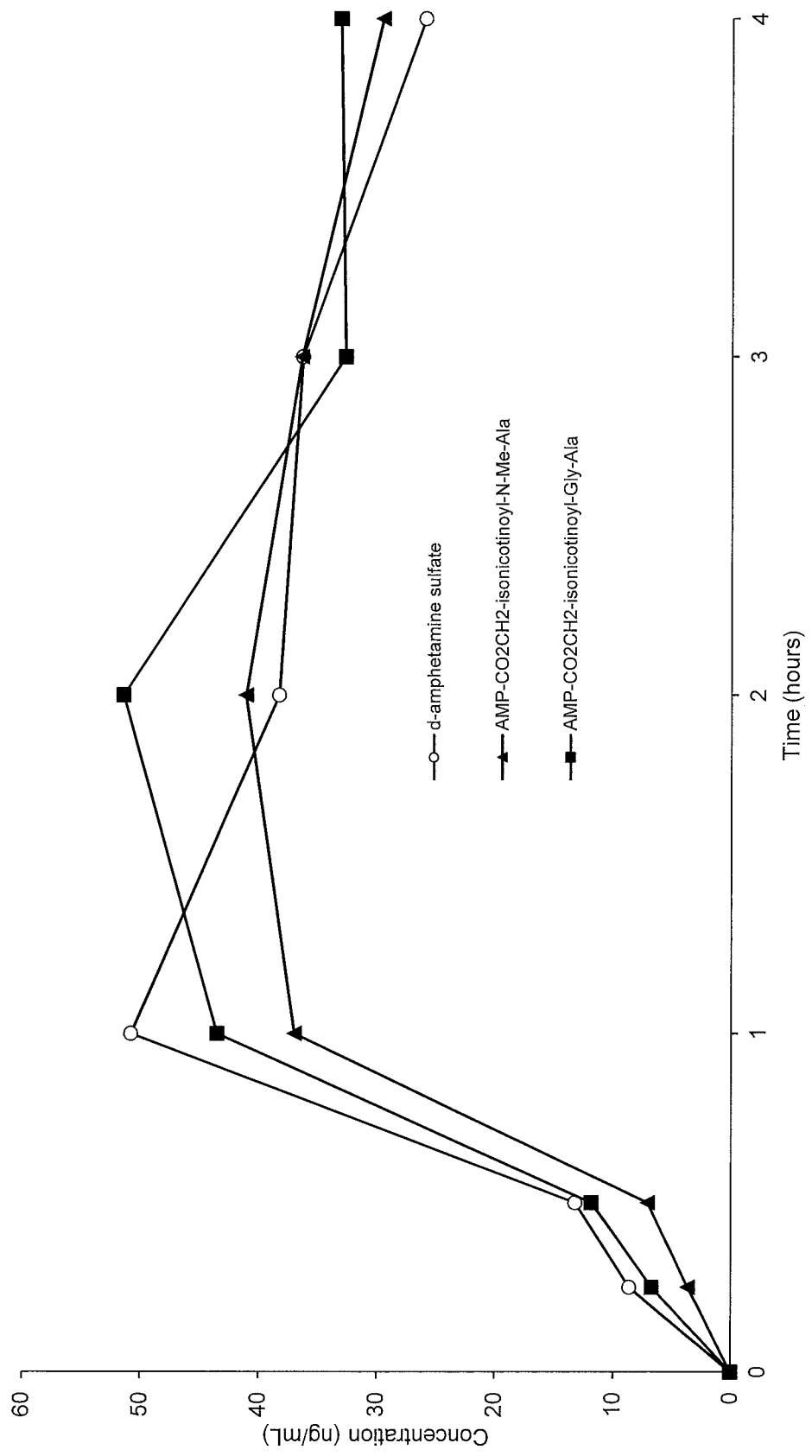
FIG. 9. Oral PK curves comparing d-amphetamine sulfate, d-amphetamine-$CO_2CH_2$-isonicotinoyl-N-methyl-L-alanine (AMP-$CO_2CH_2$-isonicotinoyl-N-Me-Ala), and d-amphetamine-$CO_2CH_2$-isonicotinoyl-glycyl-alanine (AMP-$CO_2CH_2$-isonicotinoyl-Gly-Ala).
Figure 10:
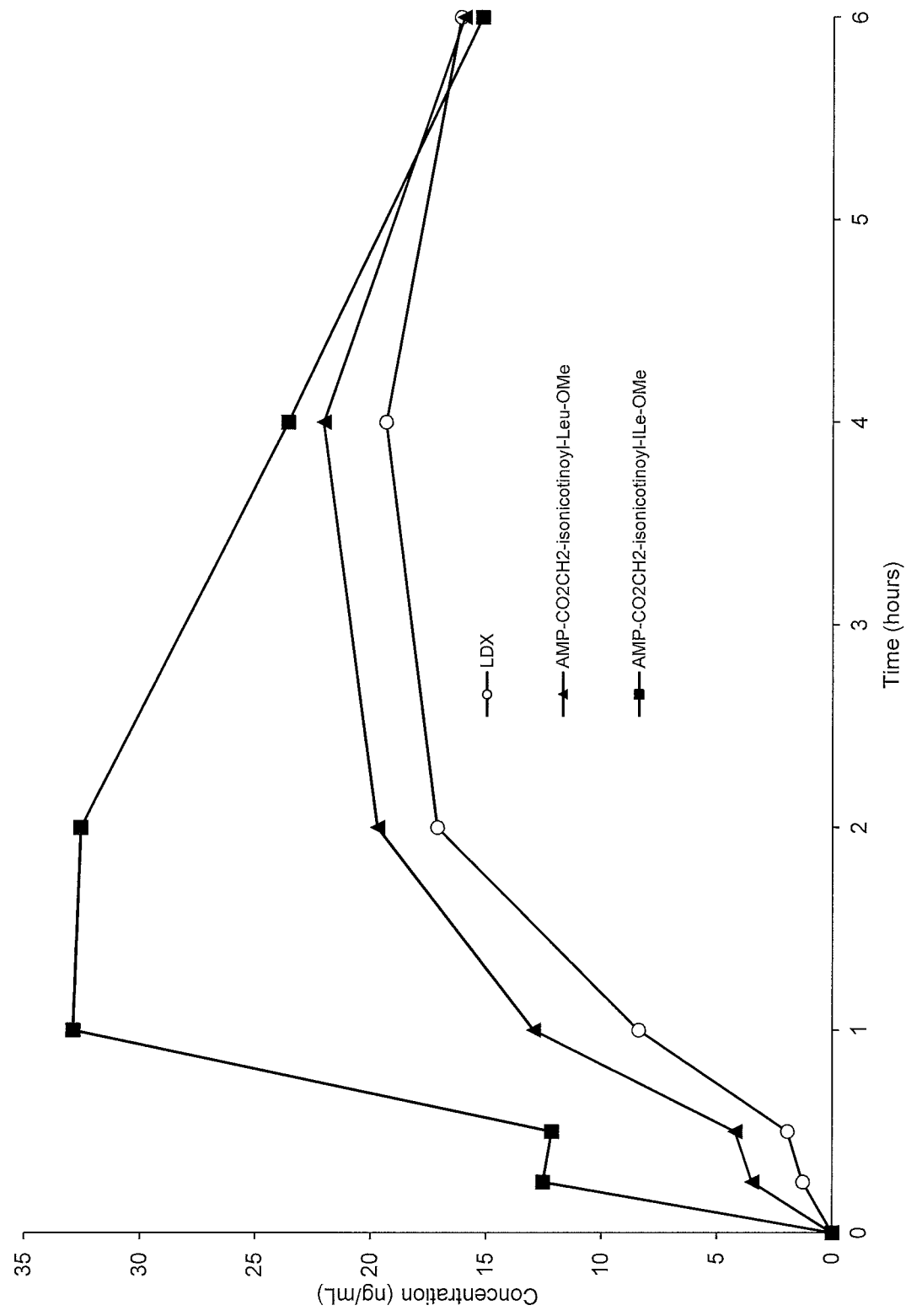
FIG. 10. Oral PK curves comparing lisdexamfetamine (LDX), d-amphetamine-$CO_2CH_2$-isonicotinoyl-leucine methyl ester (AMP-$CO_2CH_2$-isonicotinoyl-Leu-OMe), and d-amphetamine-$CO_2CH_2$-isonicotinoyl-isoleucine methyl ester (AMP-$CO_2CH_2$-isonicotinoyl-Ile-OMe).
Figure 11:
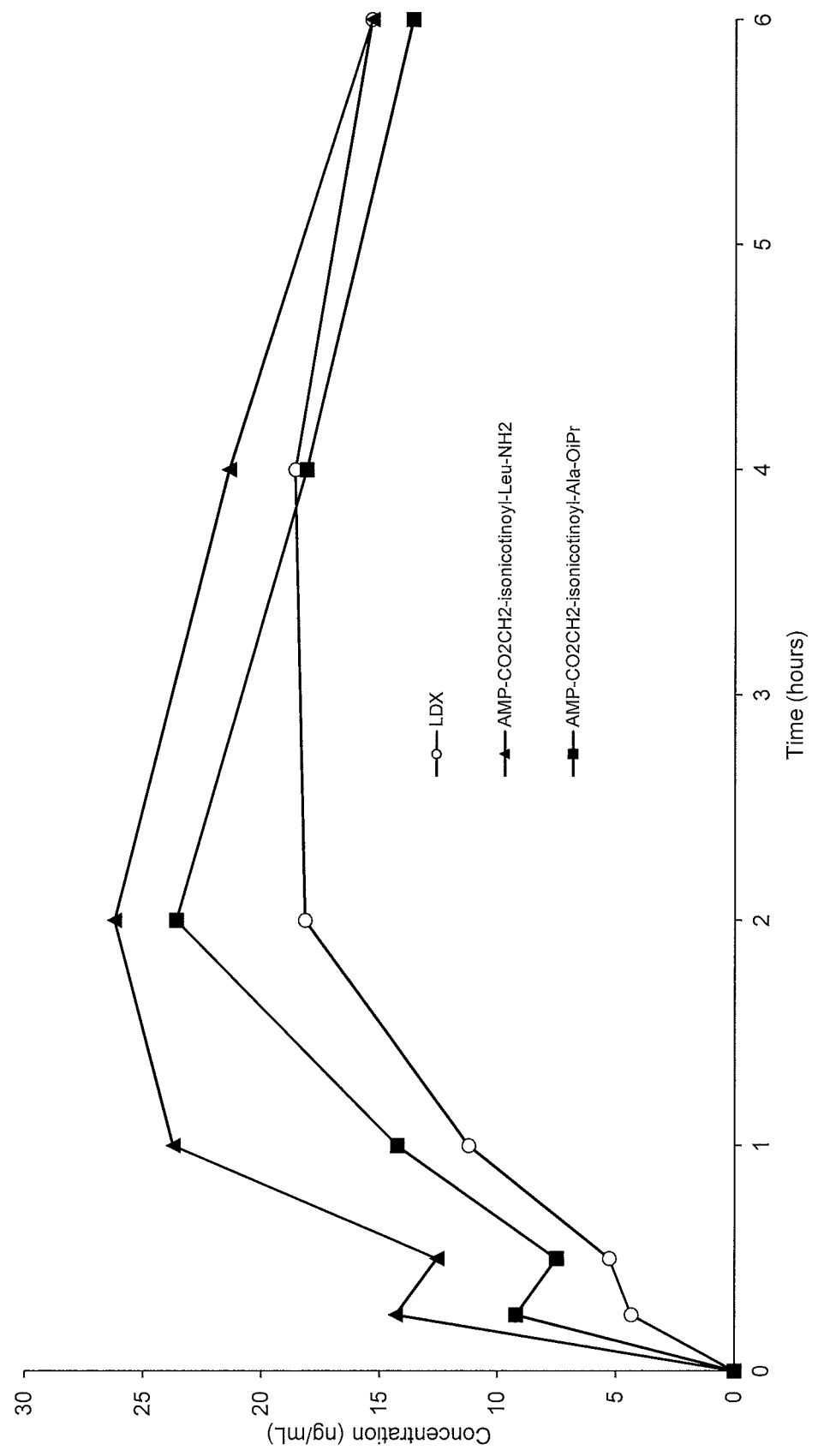
FIG. 11. Oral PK curves comparing lisdexamfetamine (LDX), d-amphetamine-$CO_2CH_2$-isonicotinoyl-leucine amide (AMP-$CO_2CH_2$-isonicotinoyl-Leu-$NH_2$), and d-amphetamine-$CO_2CH_2$-isonicotinoyl-alanine isopropyl ester (AMP-$CO_2CH_2$-isonicotinoyl-Ala-OiPr).
Figure 12:
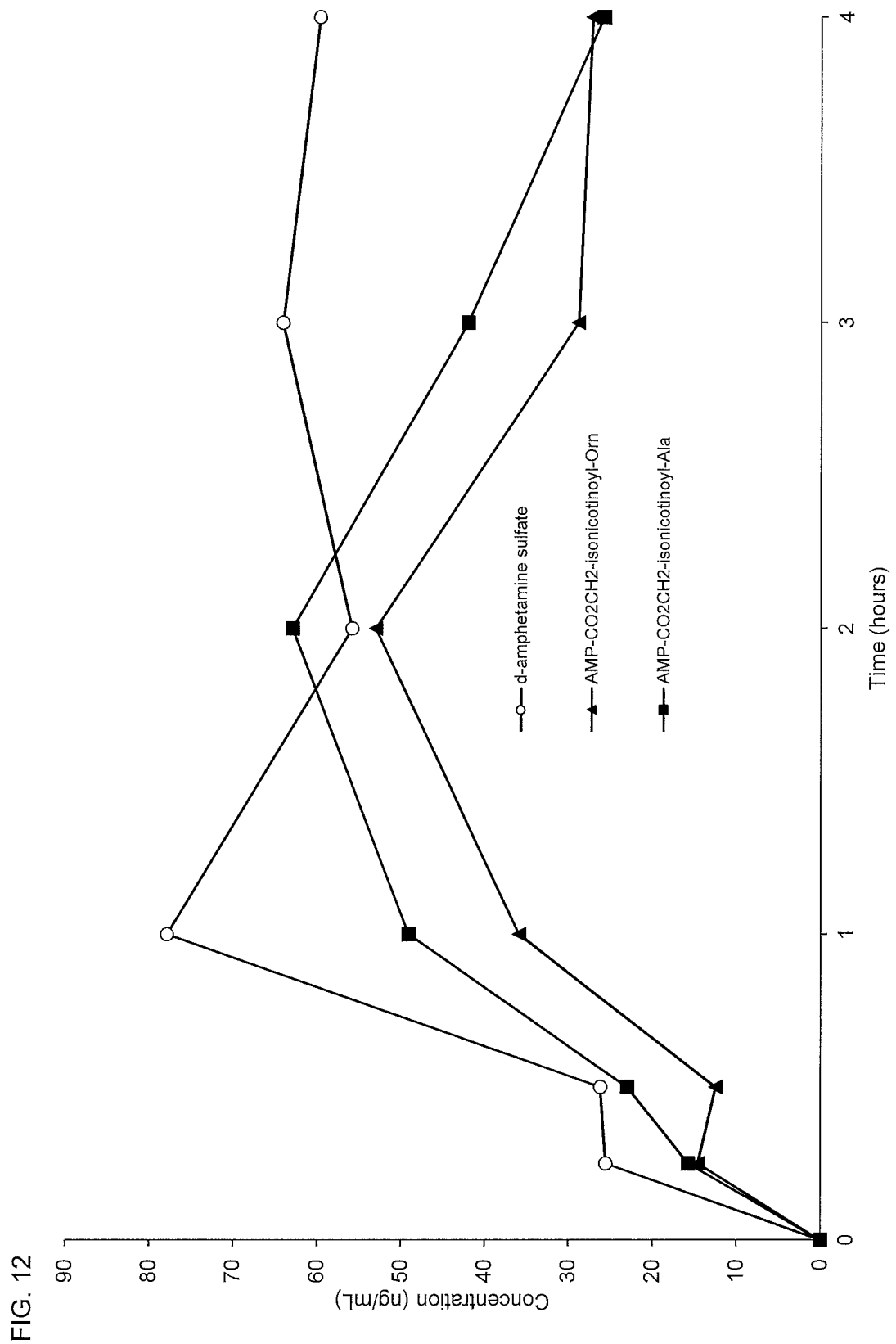
FIG. 12. Oral PK curves comparing d-amphetamine sulfate, d-amphetamine-$CO_2CH_2$-isonicotinoyl-ornithine (AMP-$CO_2CH_2$-isonicotinoyl-Orn), and d-amphetamine-$CO_2CH_2$-isonicotinoyl-alanine (AMP-$CO_2CH_2$-isonicotinoyl-Ala).
Figure 13:
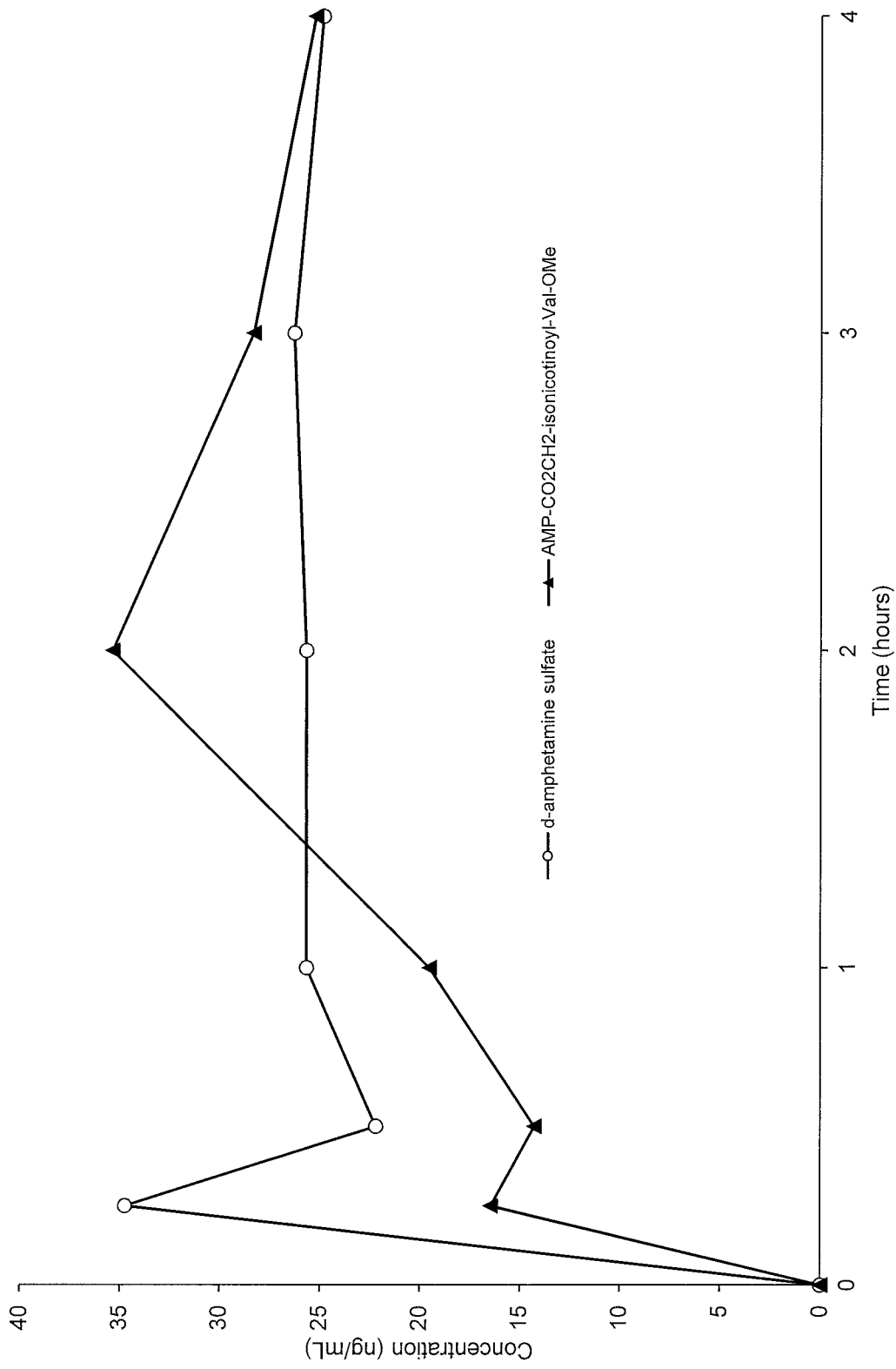
FIG. 13. Oral PK curves comparing d-amphetamine sulfate, d-amphetamine-$CO_2CH_2$-isonicotinoyl-valine methyl ester (AMP-$CO_2CH_2$-isonicotinoyl-Val-OMe).
Figure 14:
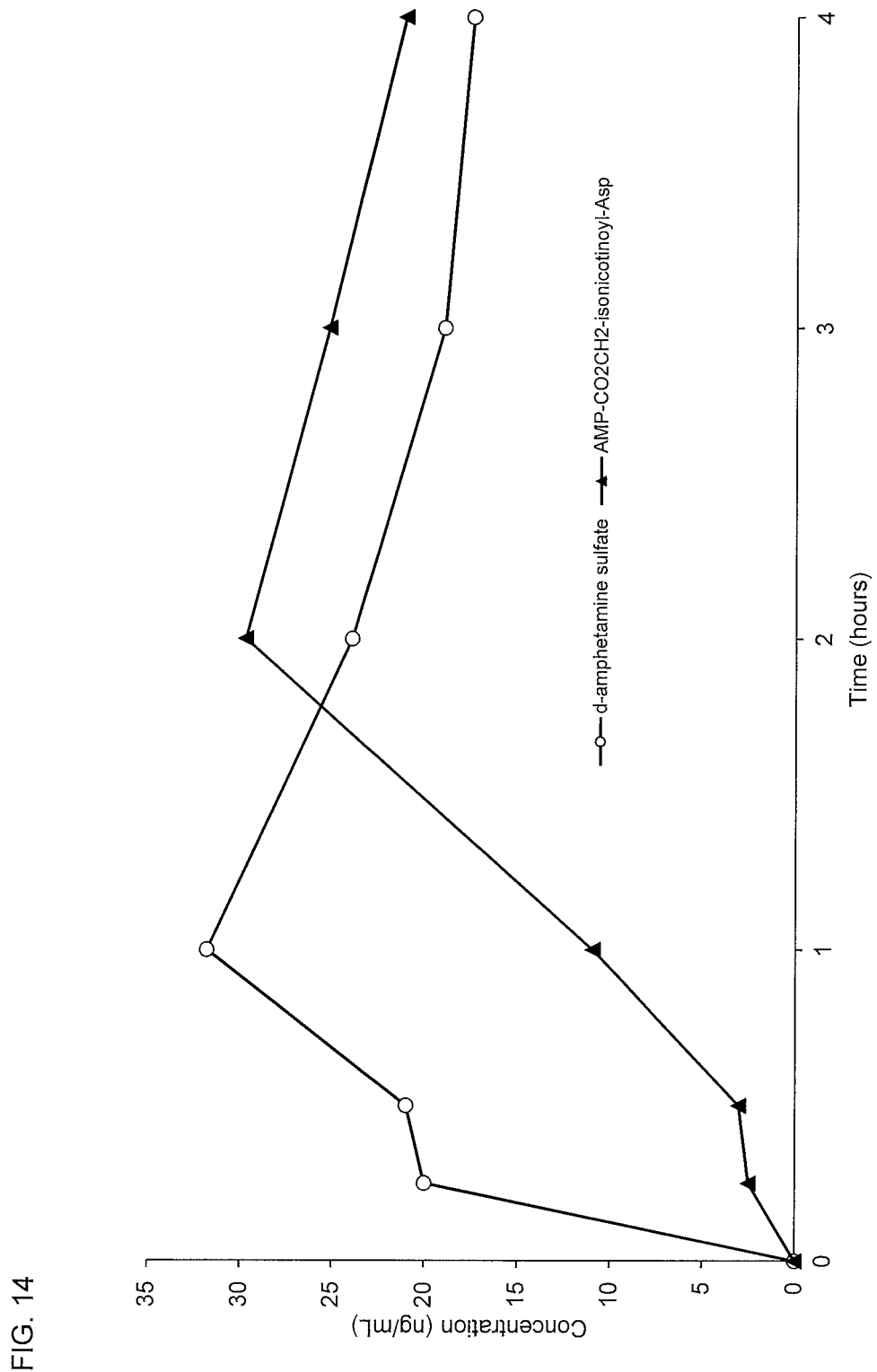
FIG. 14. Oral PK curves comparing d-amphetamine sulfate and d-amphetamine-$CO_2CH_2$-isonicotinoyl-aspartic acid (AMP-$CO_2CH_2$-isonicotinoyl-Asp)
Figure 15:
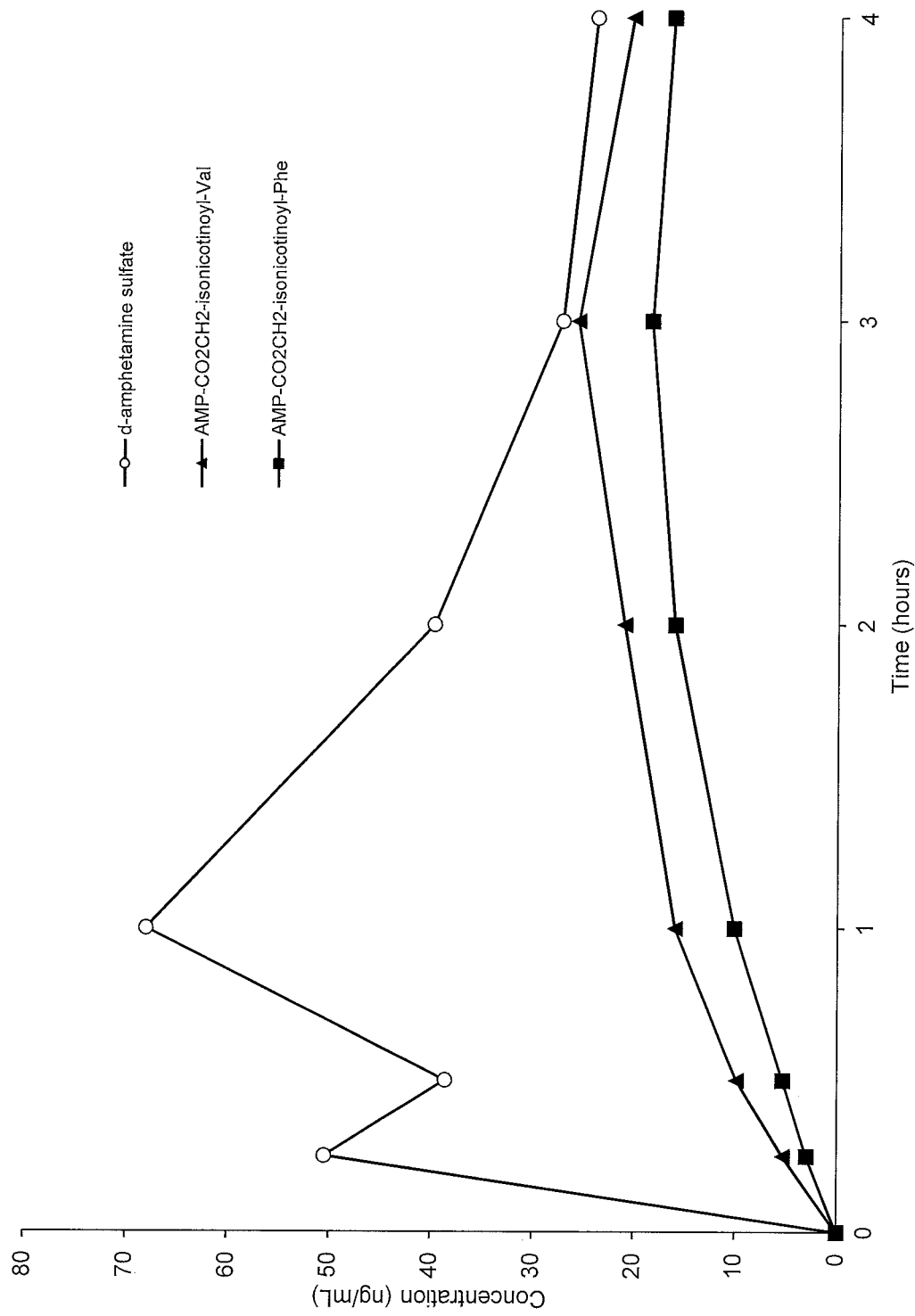
FIG. 15. Oral PK curves comparing d-amphetamine sulfate, d-amphetamine-$CO_2CH_2$-isonicotinoyl-valine (AMP-$CO_2CH_2$-isonicotinoyl-Val), and d-amphetamine-$CO_2CH_2$-isonicotinoyl-phenylalanine (AMP-$CO_2CH_2$-isonicotinoyl-Phe).
Figure 16:
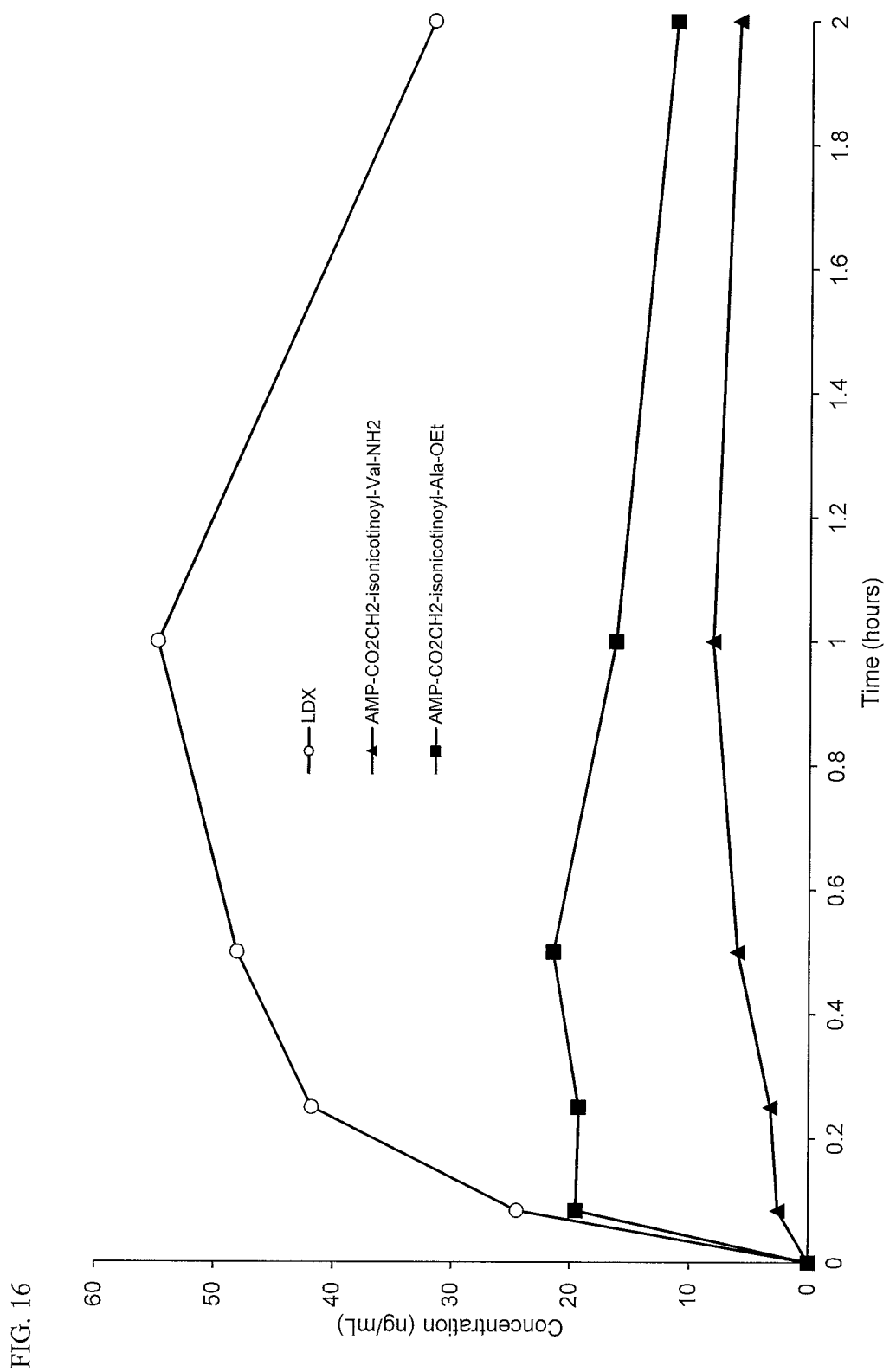
FIG. 16. Intravenous PK curves comparing lisdexamfetamine (LDX), d-amphetamine-$CO_2CH_2$-isonicotinoyl-valinamide (AMP-$CO_2CH_2$-isonicotinoyl-Val-$NH_2$), and d-amphetamine-$CO_2CH_2$-isonicotinoyl-alanine ethyl ester (AMP-$CO_2CH_2$-isonicotinoyl-Ala-OEt).
Figure 17:
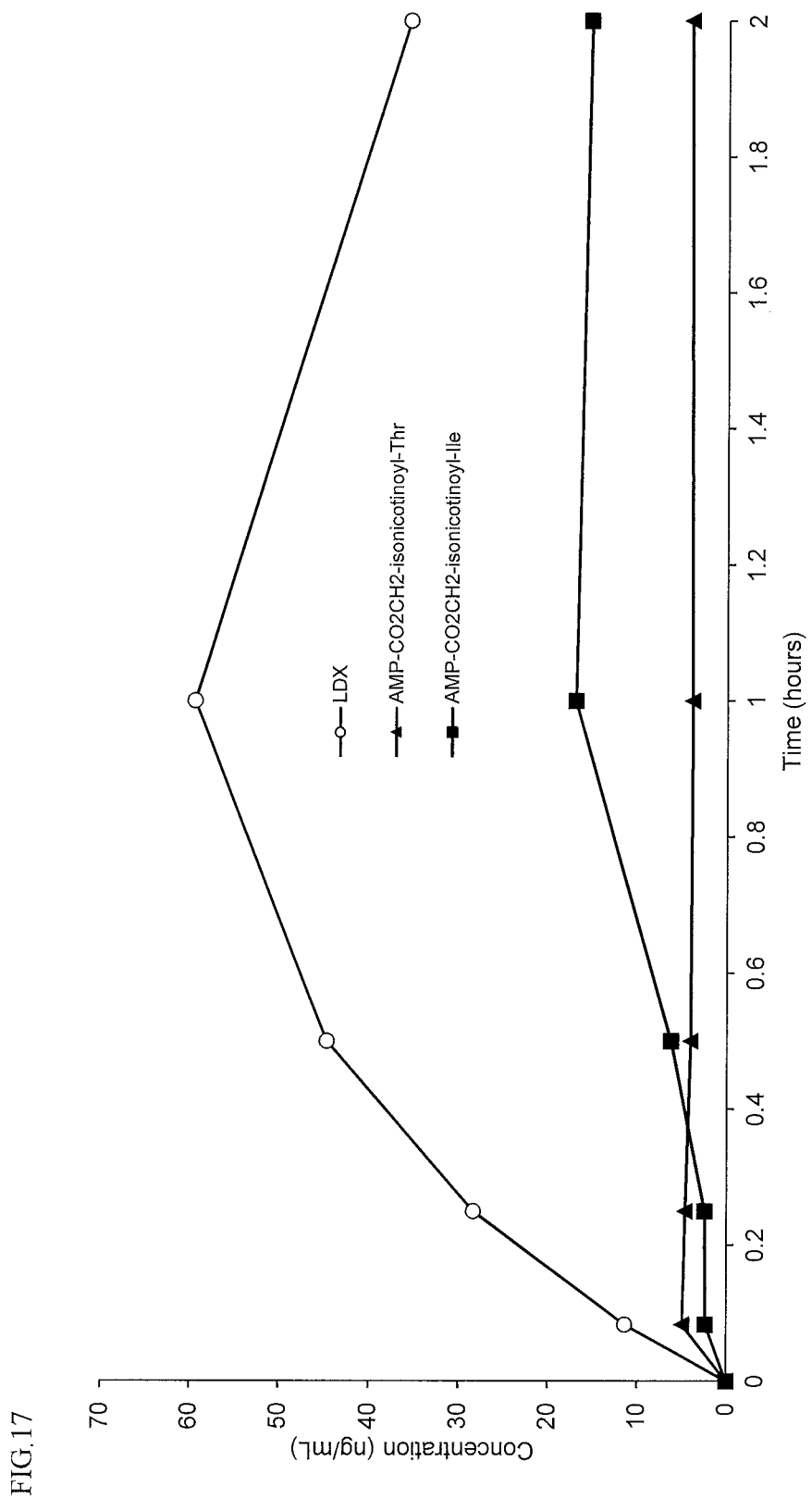
FIG. 17. Intravenous PK curves comparing lisdexamfetamine (LDX), d-amphetamine-$CO_2CH_2$-isonicotinoyl-threonine (AMP-$CO_2CH_2$-isonicotinoyl-Thr), and d-amphetamine-$CO_2CH_2$-isonicotinoyl-isoleucine (AMP-$CO_2CH_2$-isonicotinoyl-Ile).
Figure 18:
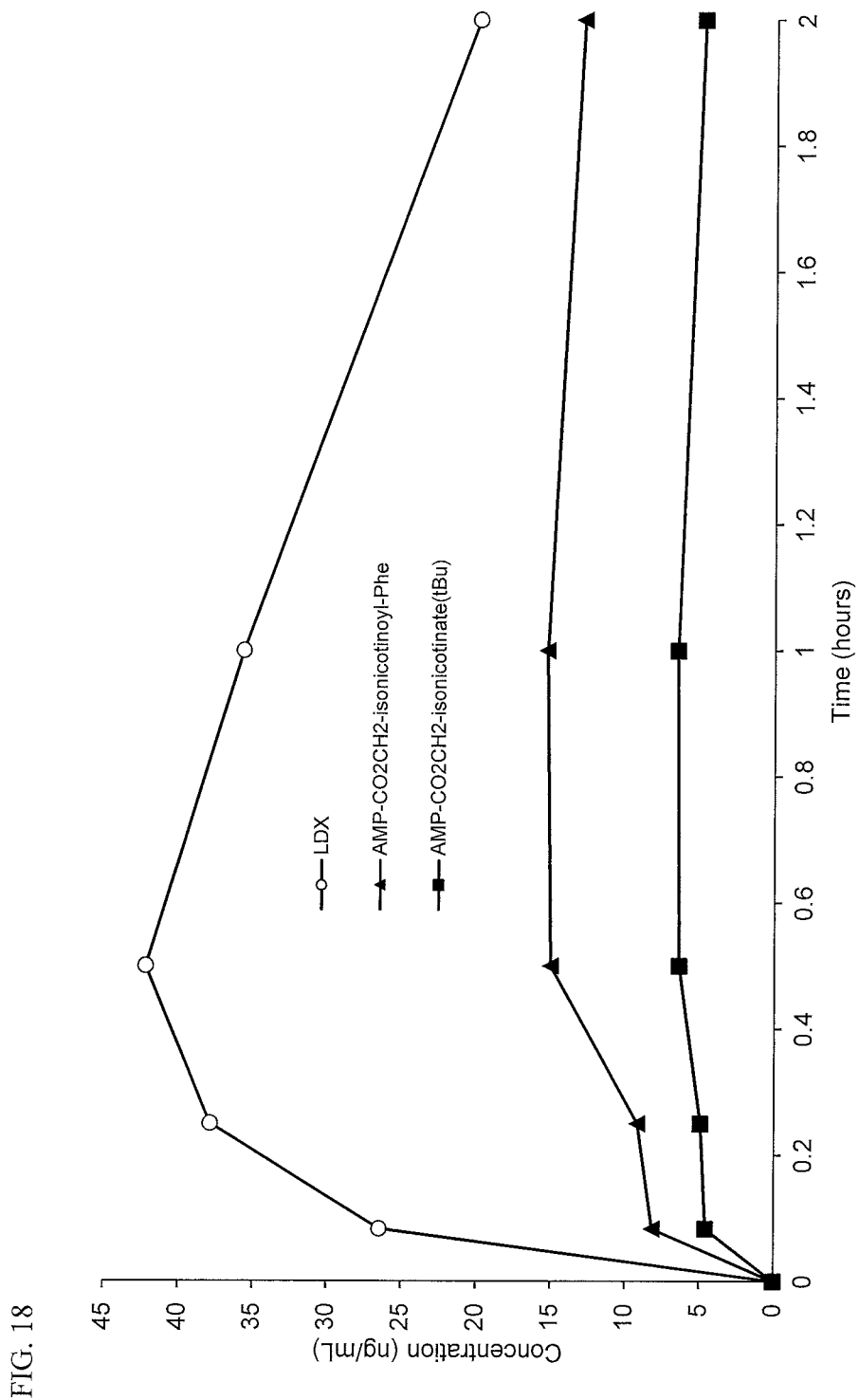
FIG. 18. Intravenous PK curves comparing lisdexamfetamine (LDX), d-amphetamine-$CO_2CH_2$-isonicotinoyl-phenylalanine (AMP-$CO_2CH_2$-isonicotinoyl-Phe), and d-amphetamine-$CO_2CH_2$-isonicotinate-tert-butyl ester (AMP-$CO_2CH_2$-isonicotinate(tBu)).
Figure 19:
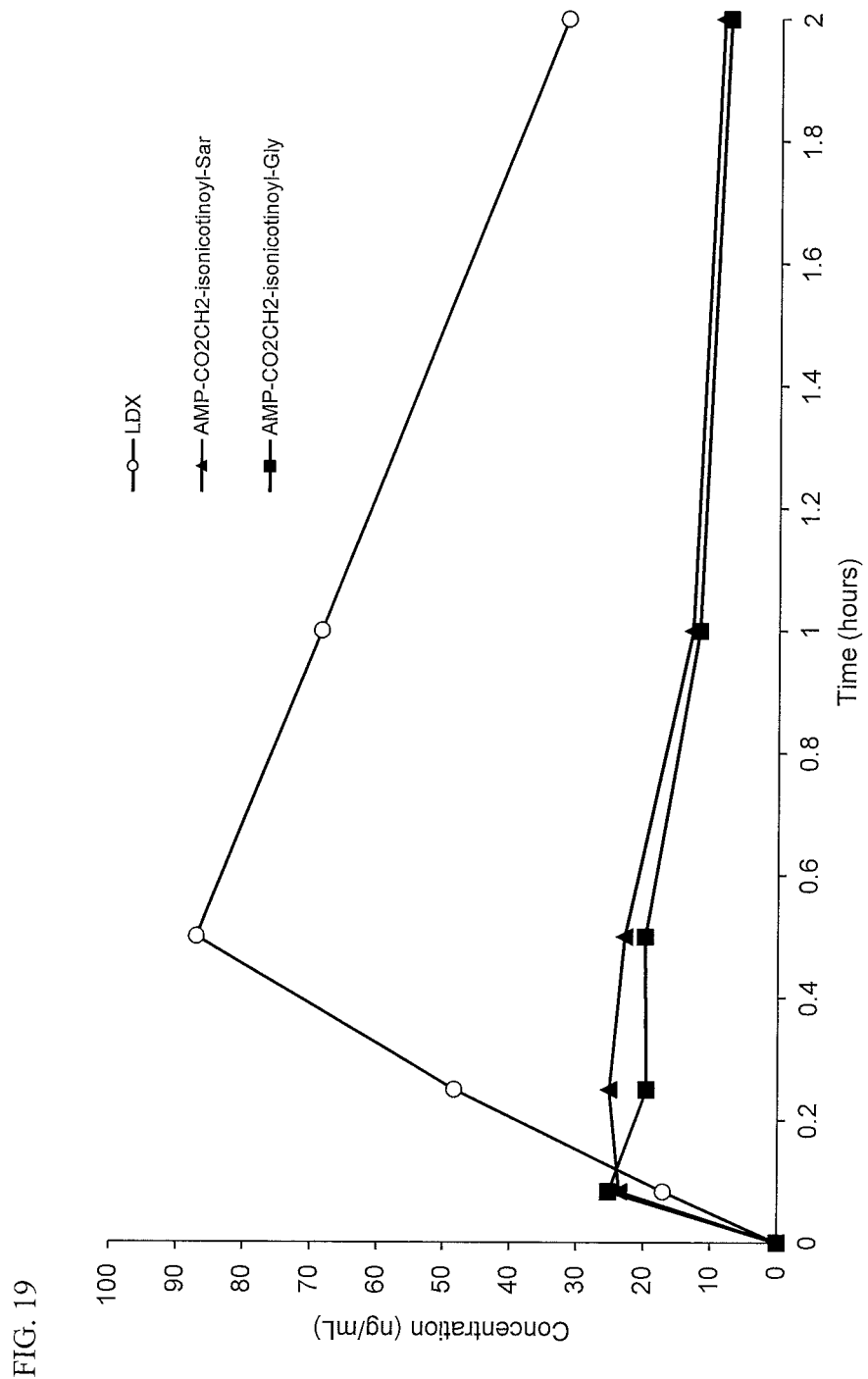
FIG. 19. Intravenous PK curves comparing lisdexamfetamine (LDX), d-amphetamine-$CO_2CH_2$-isonicotinoyl-sarcosine (AMP-$CO_2CH_2$-isonicotinoyl-Sar), and d-amphetamine-$CO_2CH_2$-isonicotinoyl-glycine (AMP-$CO_2CH_2$-isonicotinoyl-Gly).
Figure 20:
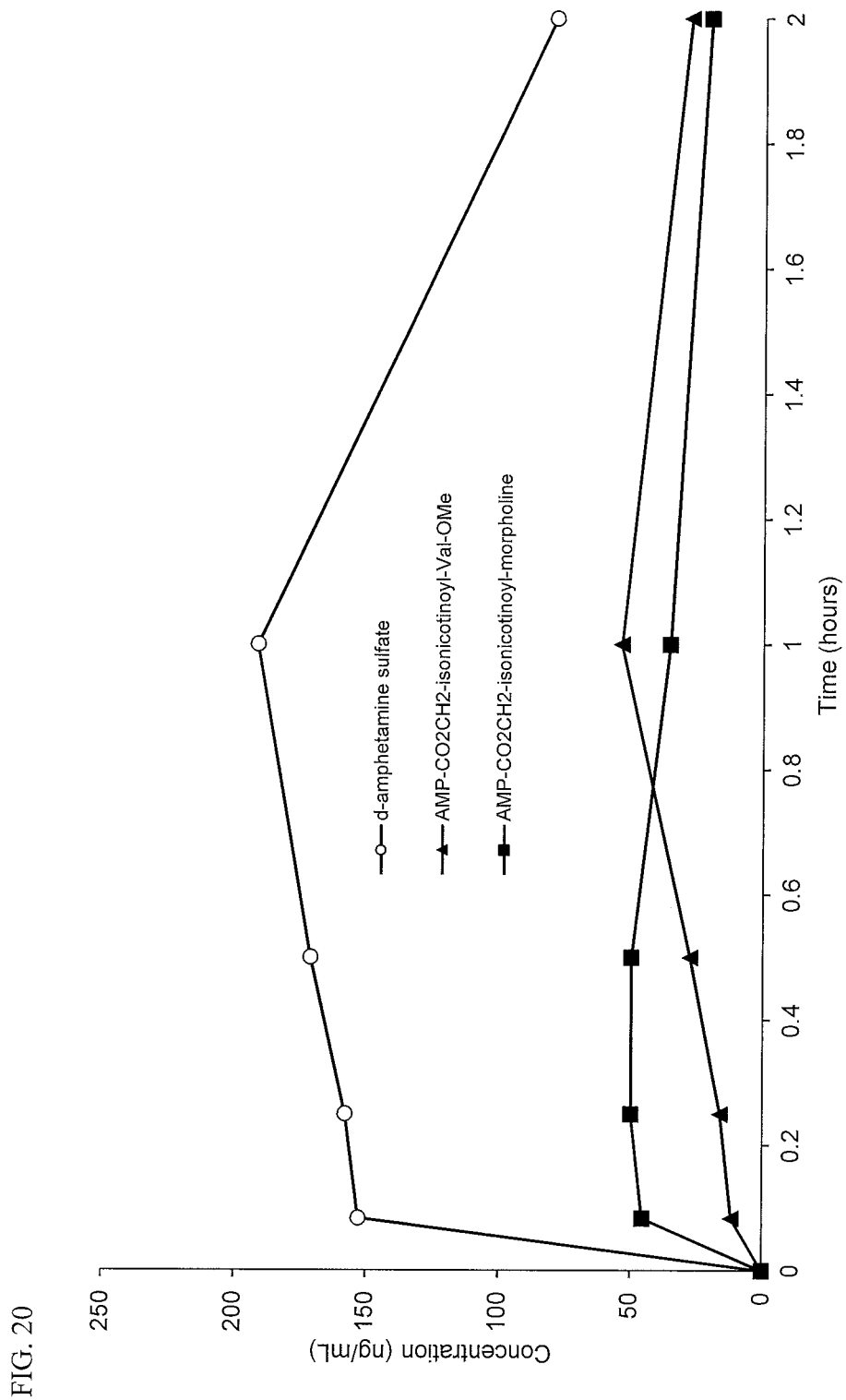
FIG. 20. Intravenous PK curves comparing d-amphetamine sulfate, d-amphetamine-$CO_2CH_2$-isonicotinoyl-valine methyl ester (AMP-$CO_2CH_2$-isonicotinoyl-Val-OMe), and d-amphetamine-$CO_2CH_2$-isonicotinoyl-morpholine (AMP-$CO_2CH_2$-isonicotinoyl-morpholine).
Figure 21:
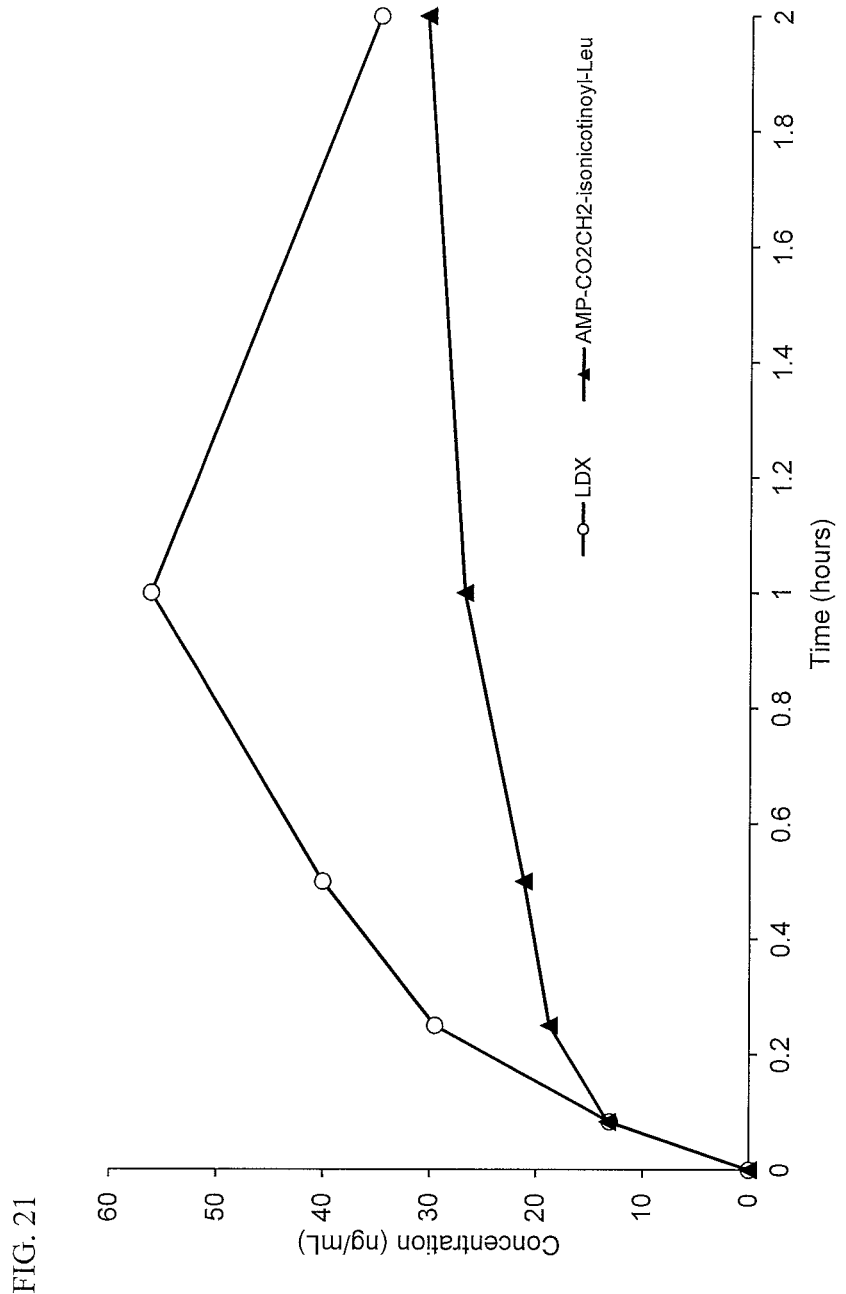
FIG. 21. Intravenous PK curves comparing lisdexamfetamine (LDX) and d-amphetamine-$CO_2CH_2$-isonicotinoyl-leucine (AMP-$CO_2CH_2$-isonicotinoyl-Leu).
Figure 22:
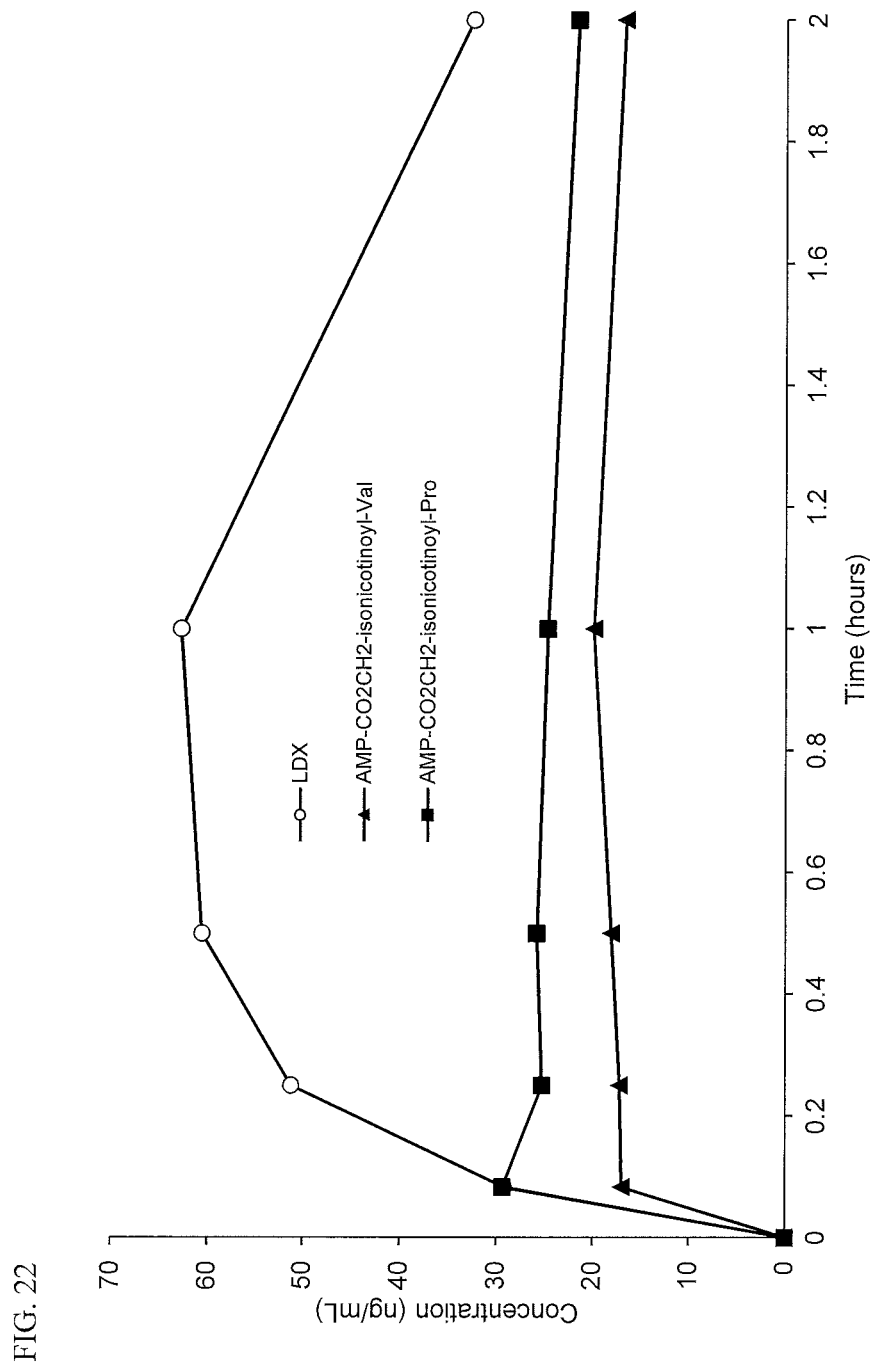
FIG. 22. Intravenous PK curves comparing lisdexamfetamine (LDX), d-amphetamine-$CO_2CH_2$-isonicotinoyl-valine (AMP-$CO_2CH_2$-isonicotinoyl-Val), and d-amphetamine-$CO_2CH_2$-isonicotinoyl-proline (AMP-$CO_2CH_2$-isonicotinoyl-Pro).
Figure 23:
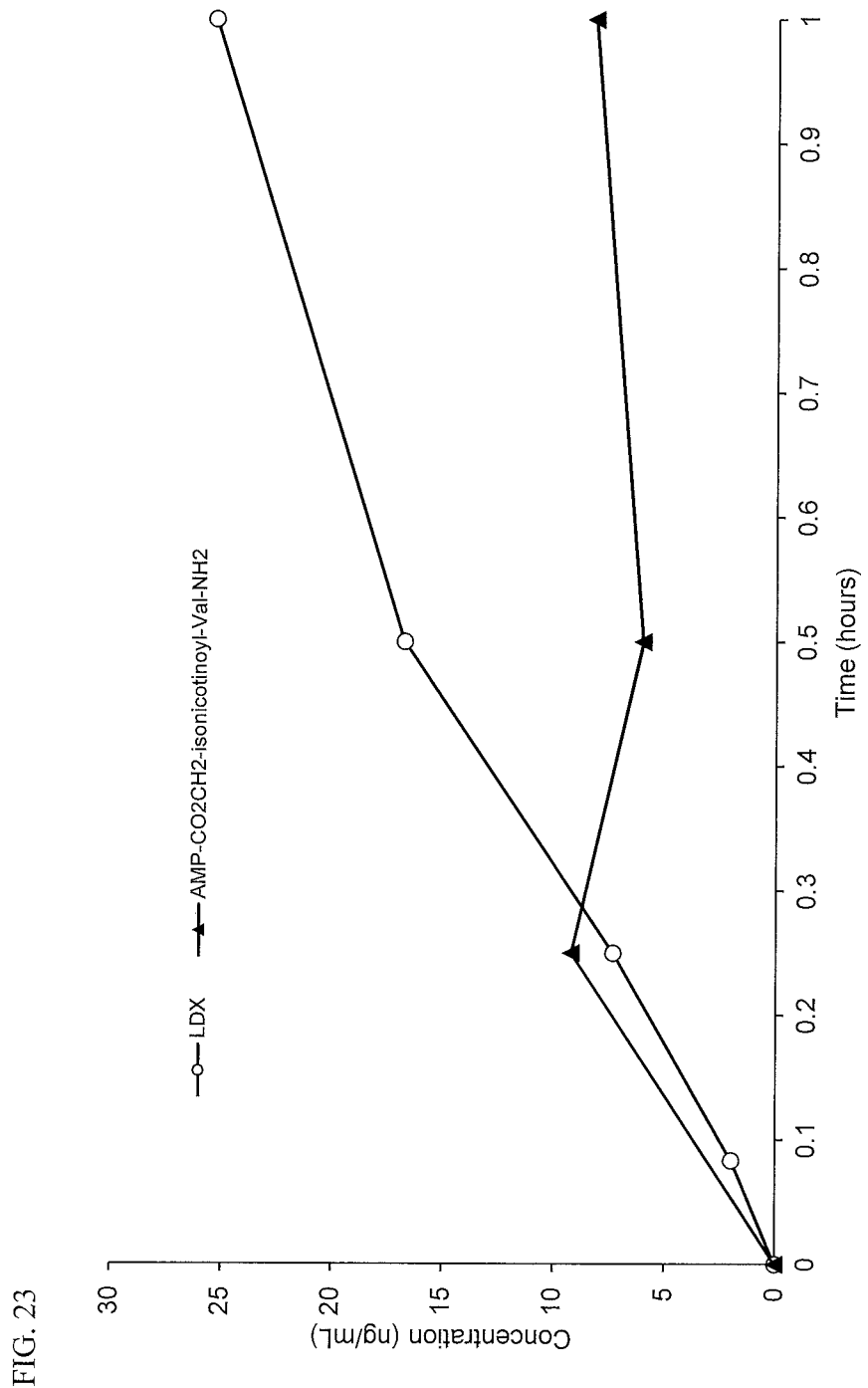
FIG. 23. Intranasal PK curves comparing lisdexamfetamine (LDX) and d-amphetamine-$CO_2CH_2$-isonicotinoyl-valinamide (AMP-$CO_2CH_2$-isonicotinoyl-Val-$NH_2$).
Figure 24:
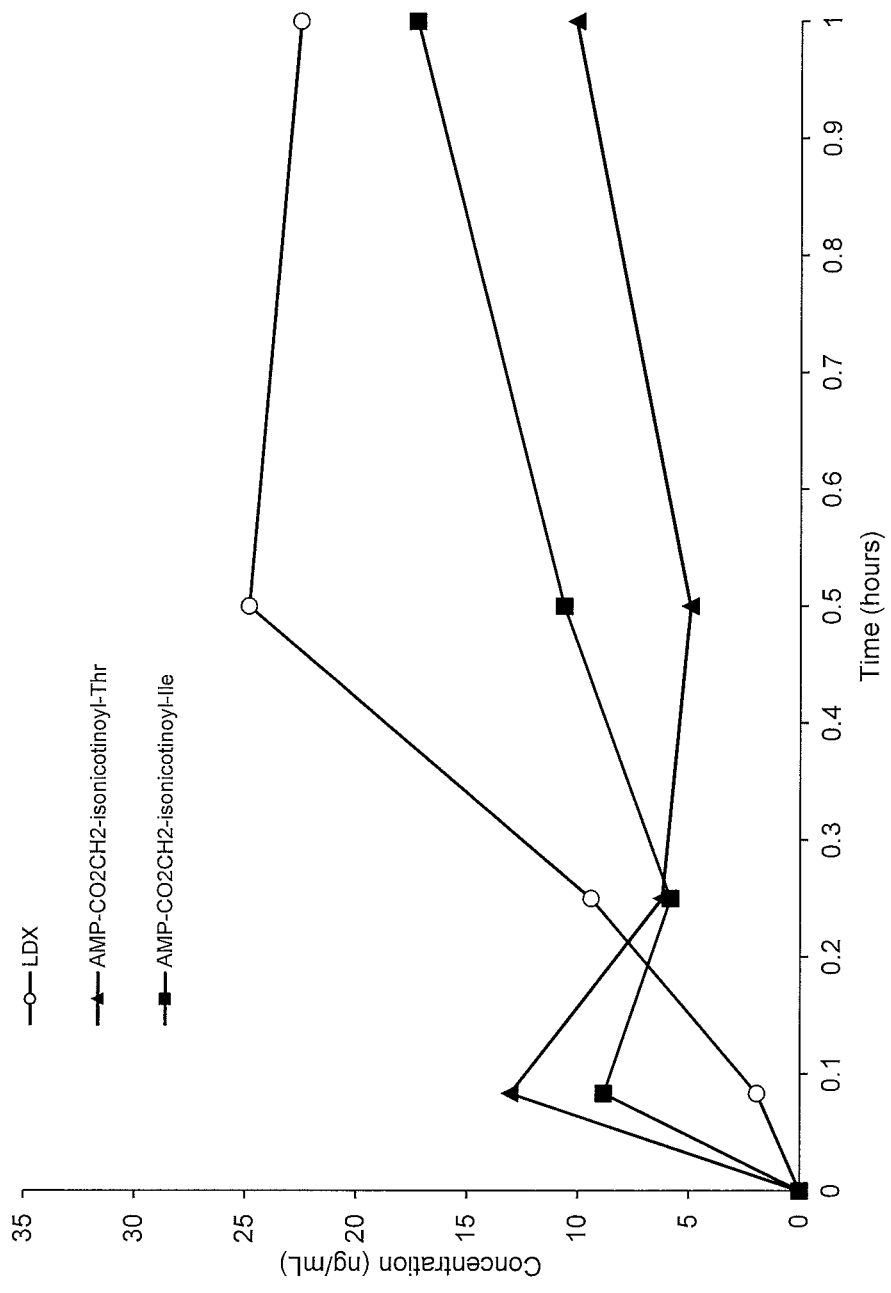
FIG. 24. Intranasal PK curves comparing lisdexamfetamine (LDX), d-amphetamine-$CO_2CH_2$-isonicotinoyl-threonine (AMP-$CO_2CH_2$-isonicotinoyl-Thr), and d-amphetamine-$CO_2CH_2$-isonicotinoyl-isoleucine (AMP-$CO_2CH_2$-isonicotinoyl-Ile).
Figure 25:
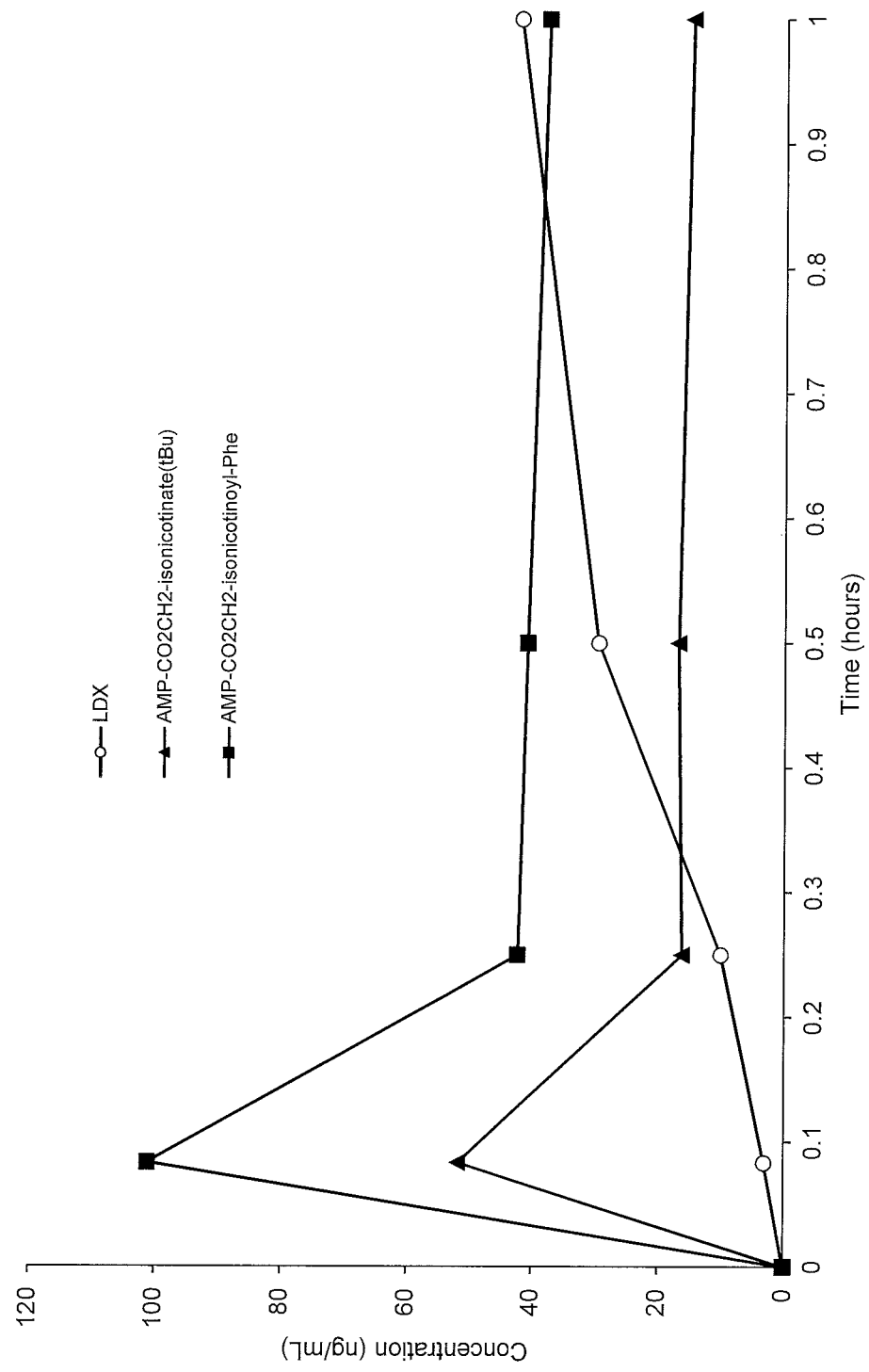
FIG. 25. Intranasal PK curves comparing lisdexamfetamine (LDX), d-amphetamine-$CO_2CH_2$-isonicotinate-tert-butyl ester (AMP-$CO_2CH_2$-isonicotinate(tBu)), and d-amphetamine-$CO_2CH_2$-isonicotinoyl-phenylalanine (AMP-$CO_2CH_2$-isonicotinoyl-Phe).
Figure 26:
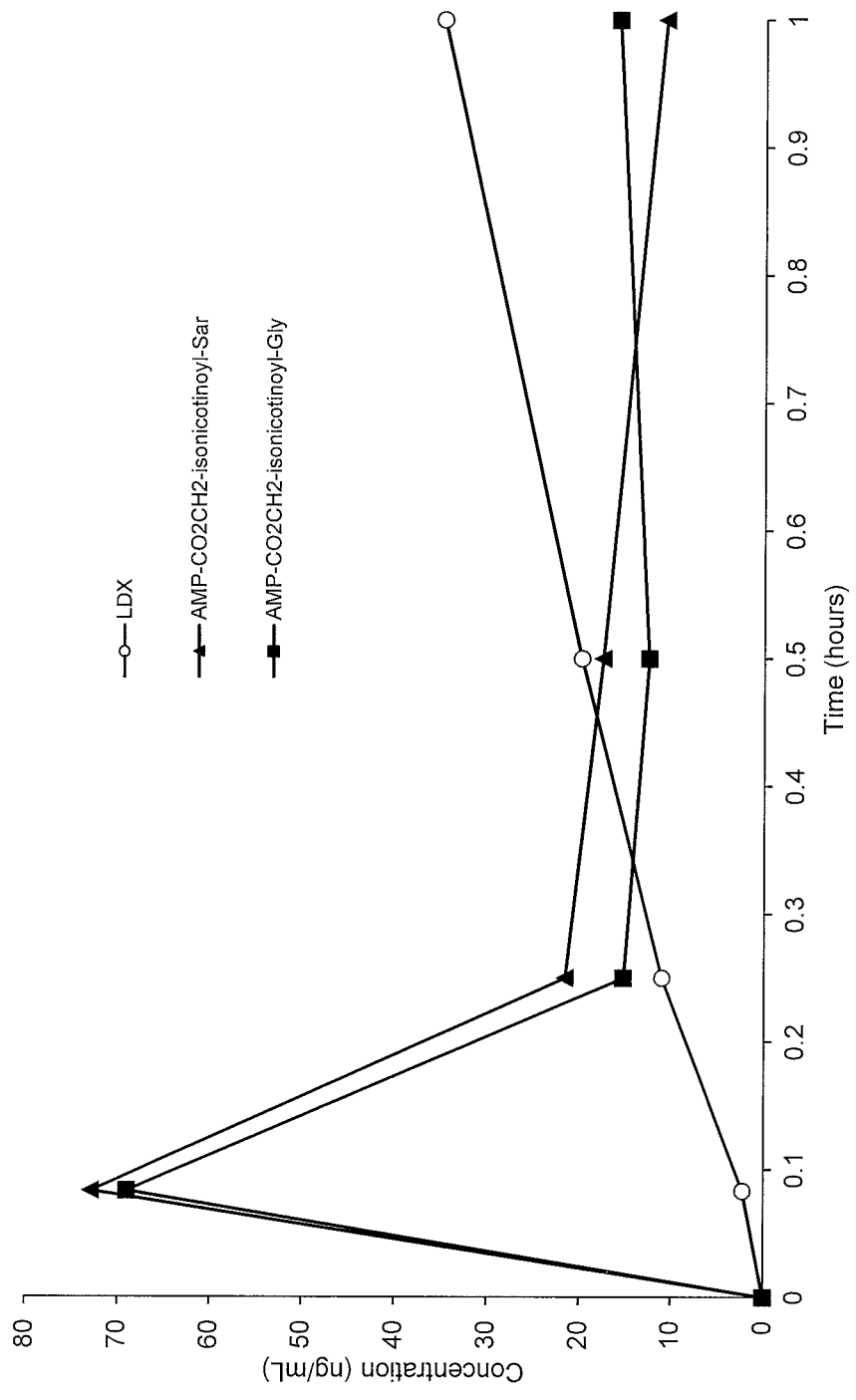
FIG. 26. Intranasal PK curves comparing lisdexamfetamine (LDX), d-amphetamine-$CO_2CH_2$-isonicotinoyl-sarcosine (AMP-$CO_2CH_2$-isonicotinoyl-Sar), and d-amphetamine-$CO_2CH_2$-isonicotinoyl-glycine (AMP-$CO_2CH_2$-isonicotinoyl-Gly).
Figure 27:
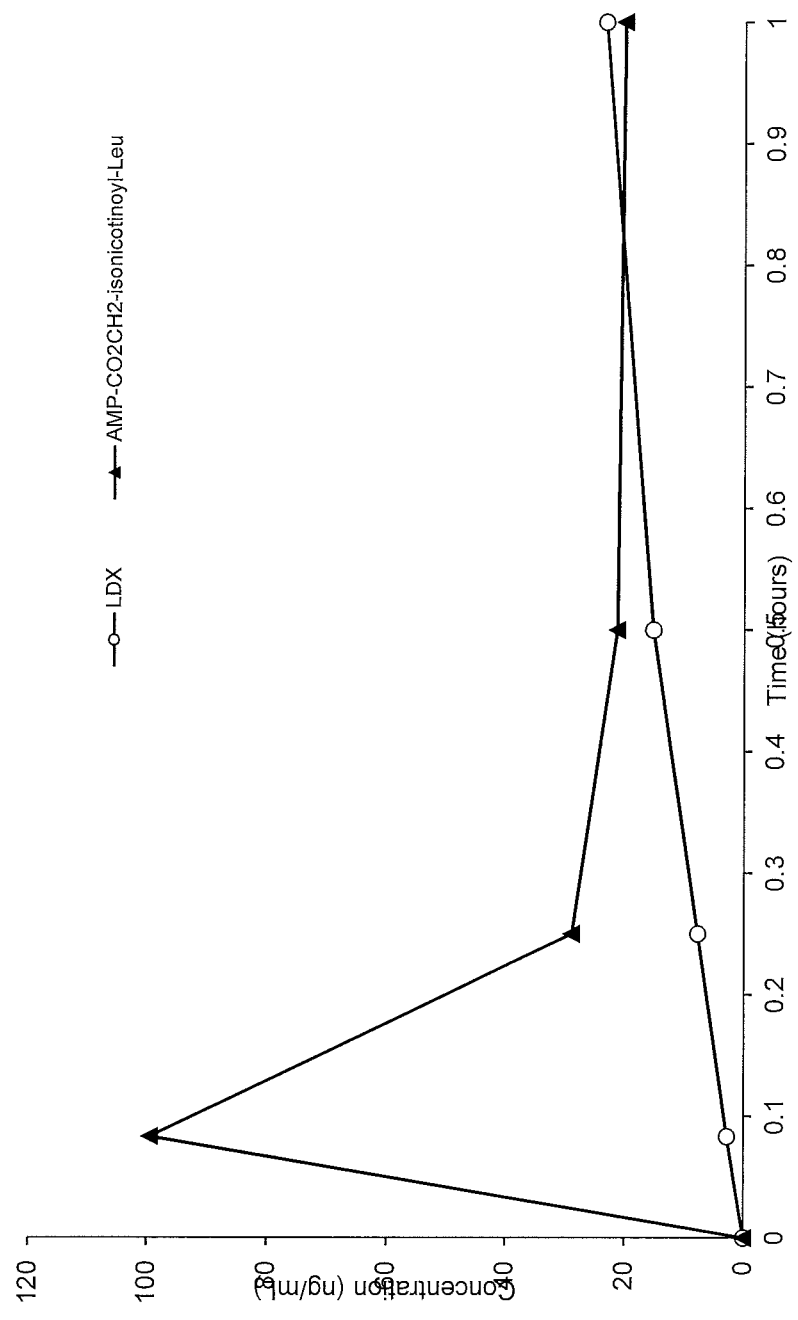
FIG. 27. Intranasal PK curves comparing lisdexamfetamine (LDX) and d-amphetamine-CO₂CH₂-isonicotinoyl-leucine (AMP-CO₂CH₂-isonicotinoyl-Leu).
Figure 28:
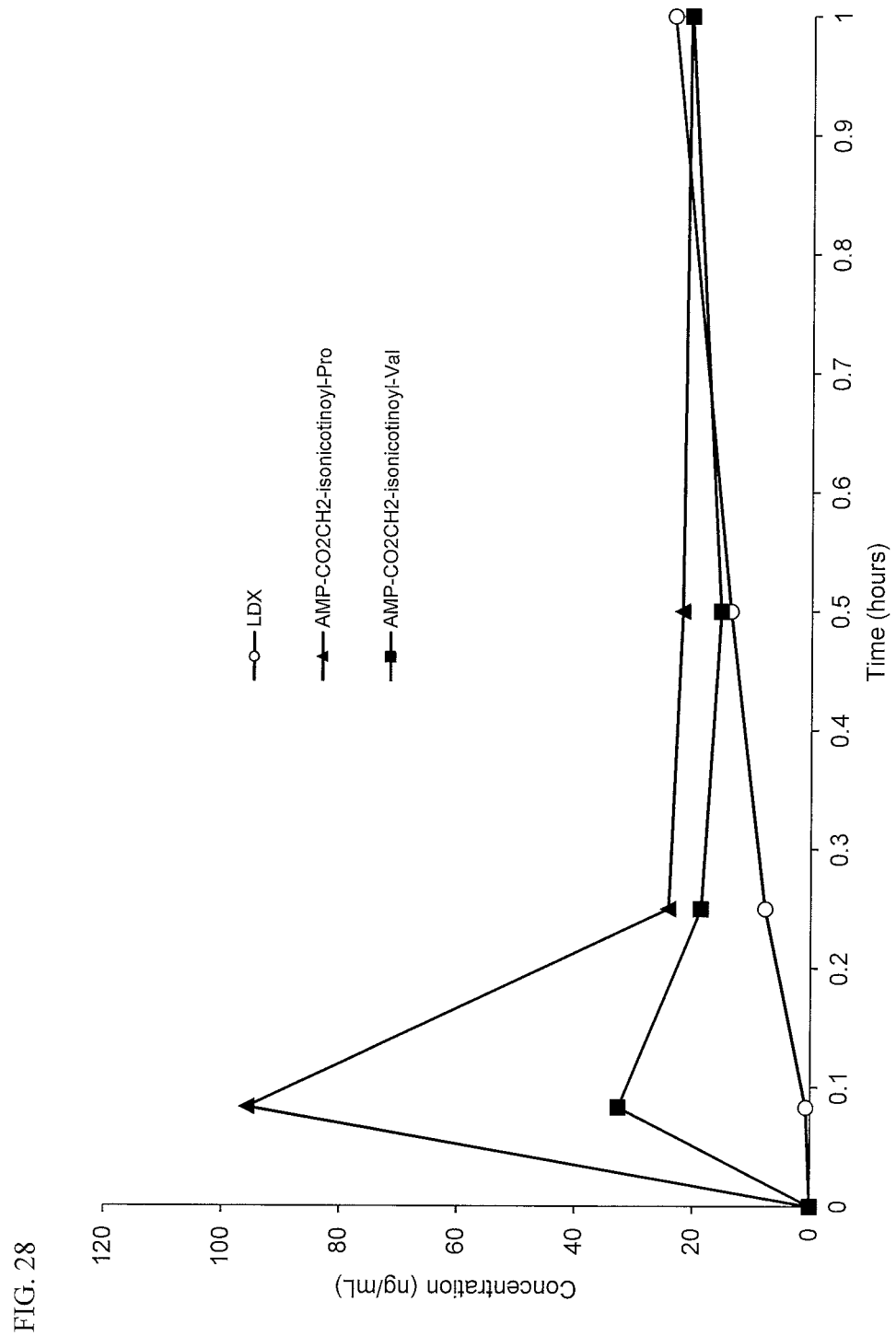
FIG. 28. Intranasal PK curves comparing lisdexamfetamine (LDX), d-amphetamine-CO₂CH₂-isonicotinoyl-proline (AMP-CO₂CH₂-isonicotinoyl-Pro), and d-amphetamine-CO₂CH₂-isonicotinoyl-valine (AMP-CO₂CH₂-isonicotinoyl-Val).
Figure 29:
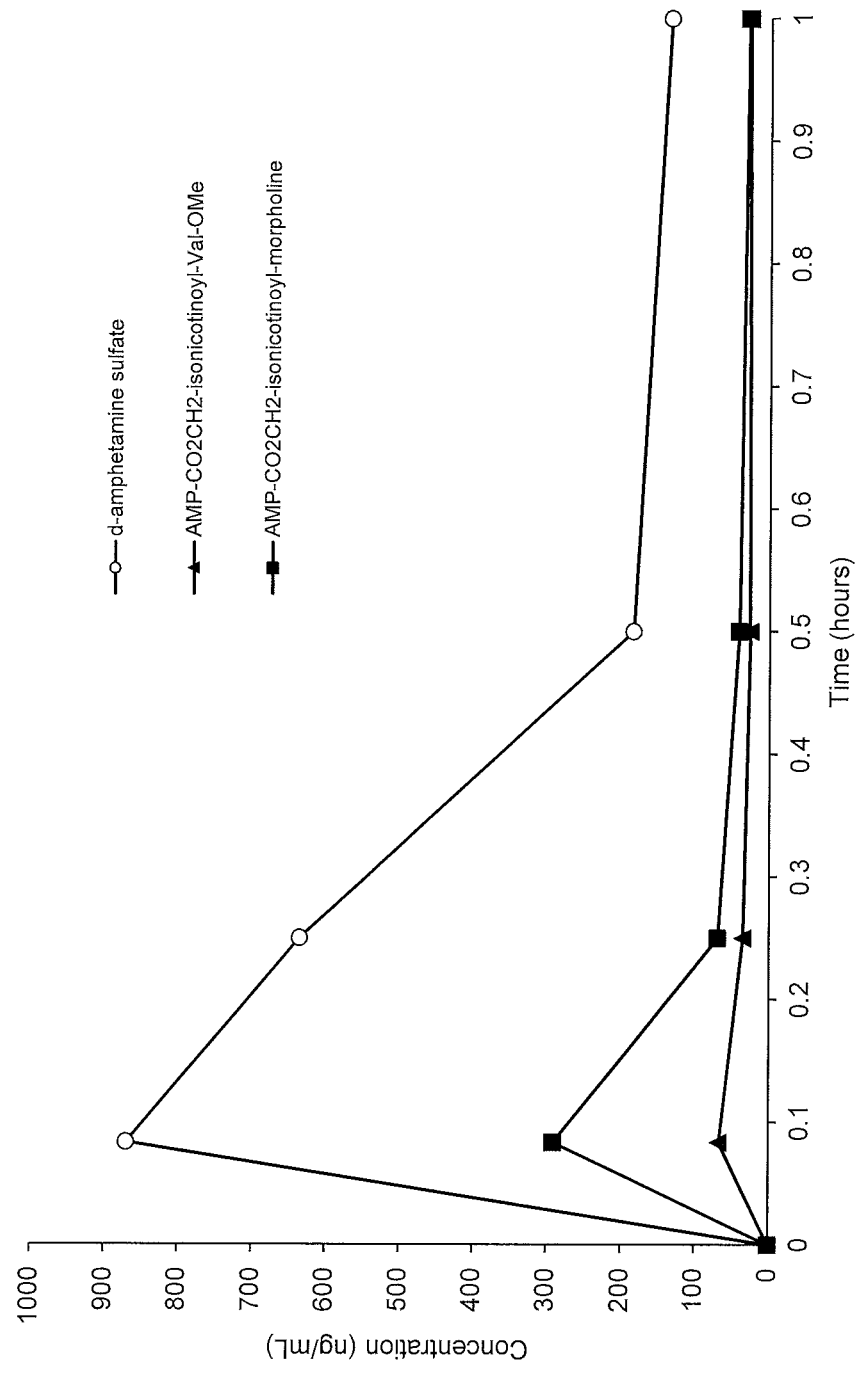
FIG. 29. Intranasal PK curves comparing d-amphetamine sulfate, d-amphetamine-CO₂CH₂-isonicotinoyl-valine methyl ester (AMP-CO₂CH₂-isonicotinoyl-Val-OMe), and d-amphetamine-CO₂CH₂-isonicotinoyl-morpholine (AMP-CO₂CH₂-isonicotinoyl-morpholine).

The present technology describes, in general, novel compounds, and compositions of the stimulant d-amphetamine, salts thereof, other derivatives thereof, and combinations thereof. Additionally, the presently described technology also relates generally to the methods of making and using these new compounds, and compositions.

As used herein, an "amino acid" refers to a natural, standard, non-standard, unusual, synthetic, and/or essential amino acid, and can be an L-amino acid or a D-amino acid, or a combination thereof.

As used herein, "d-amphetamine" shall mean any of the sympathomimetic phenethylamine derivatives which have central nervous system stimulant activity, including, but not limited to, d-amphetamine (alpha-methyl-phenethylamine), methamphetamine, p-methoxyamphetamine, methylenedioxyamphetamine, 2,5-dimethoxy-4-methylamphetamine, 2,4,5-trimethoxyamphetamine, 3,4-methylenedioxy-methamphetamine, and methylphenidate.

As used herein, "in a manner inconsistent with the manufacturer's instructions" or similar expression is meant to include, but is not limited to, consuming amounts greater than amounts described on the label or ordered by a licensed physician, and/or altering by any means (e.g., crushing, breaking, melting, separating, etc.) the dosage formulation such that the composition may be injected, inhaled or smoked.

As used herein, the phrases such as "decreased," "reduced," "diminished" or "lowered" is meant to include at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or increments therein.

As used herein, the term "substance use disorders", or "stimulant use disorder" or the acronym "SUD", can be characterized as a maladaptive, narrowing of behaviors toward procurement and use of the drug of abuse at the expense of other, more constructive behaviors maintained by non-drug reinforcers. Success of any intervention can be measured, in part, by the extent to which it promotes a reallocation of behavior away from the drug of abuse or toward non-drug reinforcers that are generally deemed to be healthier. Pharmacotherapy, in particular agonist-like medications, have a number of properties that can promote such a behavioral reallocation.

As used herein, the term "Agonist medications", or "agonist replacement therapies", are mechanistically similar to the abused drug in terms of receptor-mediated effects and pharmacodynamic effects but differ with respect to pharmacokinetic properties. Desirable attributes for an agonist replacement therapy include overlapping receptor pharmacology with the drug of abuse, oral bioavailability, slow onset of action, long duration of action.

In accordance with some aspects, the present technology provides amphetamine in a compound form. More specifically, the amphetamine comprises at least one organic compound covalently bonded or attached to amphetamine.

In some aspects, the compound has the structure of Formula A

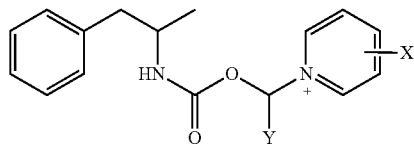

or a pharmaceutically acceptable salt thereof, where X is selected from the group consisting of an ester, carboxylic acid, amino acid, amino acid residue, amide group, and a derivative thereof, and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle.

In some aspects, the compound has the structure of Formula IA

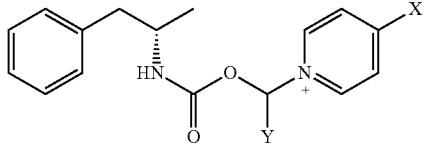

Formula IA where X is A-COO—R;

where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula IC

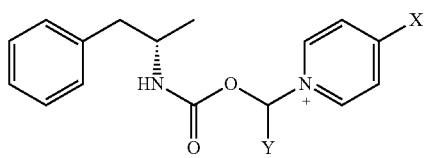

Formula IC where X is A-CO—NR$^1$R$^2$;

where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R$^1$ and R$^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula IIA:

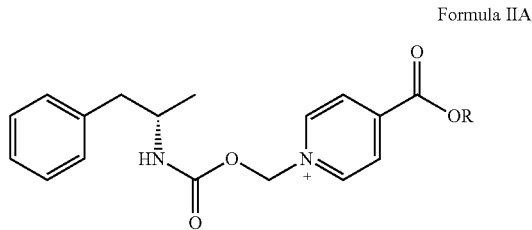

Formula IIA where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula IIC:

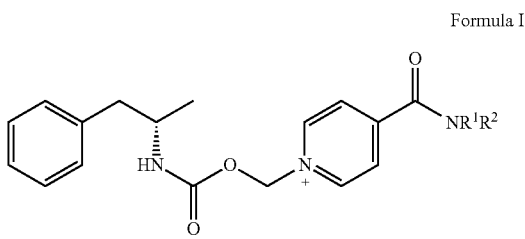

Formula IIC where Y is hydrogen, A is absent, and where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of IIE:
where R is independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula IIF:

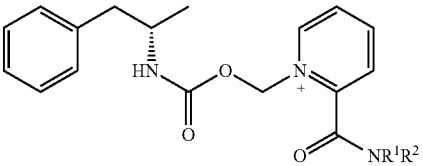

where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound has the structure of Formula I

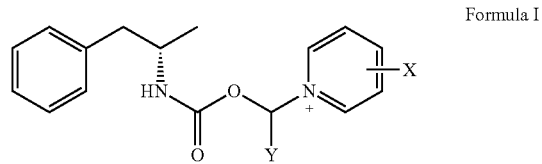

Formula I or a pharmaceutically acceptable salt thereof, where X is selected from the group consisting of an ester, carboxylic acid, amino acid, amino acid residue, amide group, and a derivative thereof, and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle.

In further aspects, one or more substituents X can be attached to the pyridine ring, wherein each X is independently selected from the group of A-COO—R and A-CO—$NR^1R^2$ In further aspects, two or more substituents X can be attached to the pyridine ring, wherein each X is independently selected from the group of A-COO—R and A-CO—$NR^1R^2$ In some aspects, the compound is AMP-$CO_2CH_2$-isonicotinate or salt thereof having the following structure:

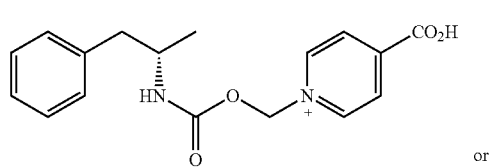

or

-continued

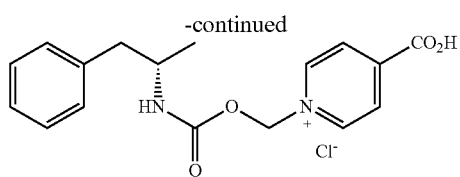

In some aspects, the compound is AMP-CO$_2$CH$_2$-isonicotinate(tBu) or a salt thereof having the following structure:

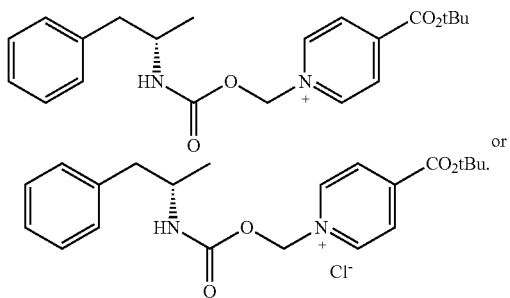

In some aspects, the compound is AMP-CO$_2$CH$_2$-isonicotinoyl-morpholine or a salt thereof having the following structure:

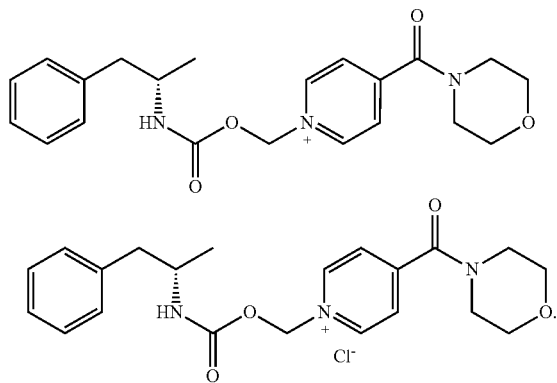

In some aspects, the compound is AMP-CO$_2$CH$_2$-isonicotinoyl-Val-NH$_2$ or a salt thereof having the following structure:

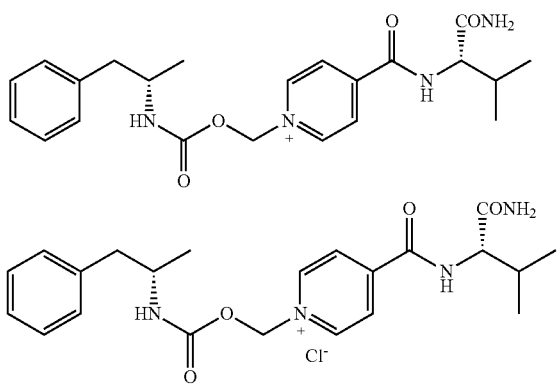

In some aspects, the compound is AMP-CO$_2$CH$_2$-isonicotinoyl-Ile or a salt thereof having the following structure:

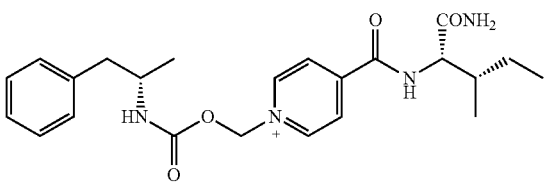

or

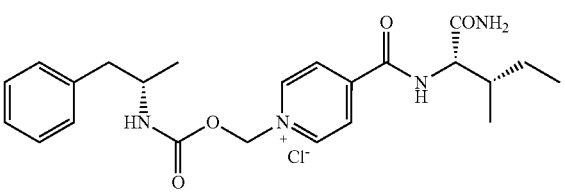

In some aspects, the compound is AMP-CO$_2$CH$_2$-isonicotinoyl-Thr or a salt thereof having the following structure:

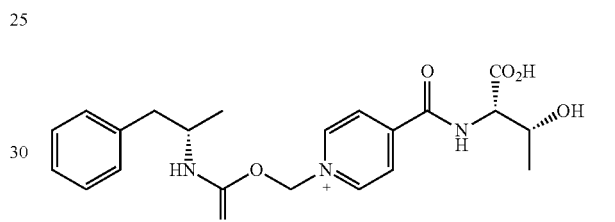

or

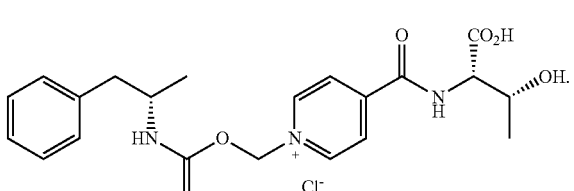

In some aspects, the compound is AMP-CO$_2$CH$_2$-isonicotinoyl-Gly or a salt thereof having the following structure:

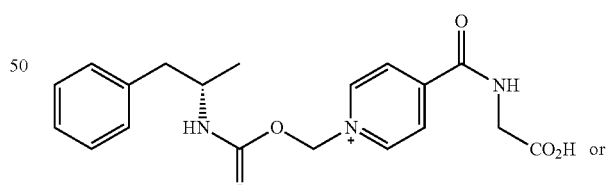

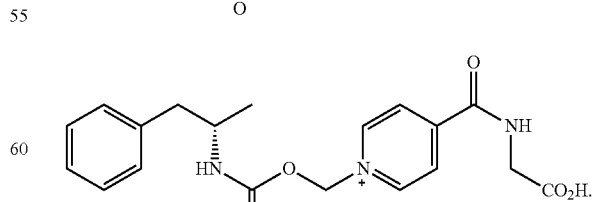

In some aspects, the compound is AMP-CO$_2$CH$_2$-isonicotinoyl-Sar or a salt thereof having the following structure:

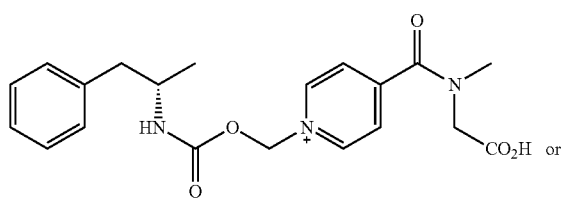

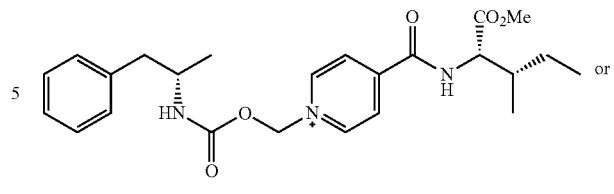

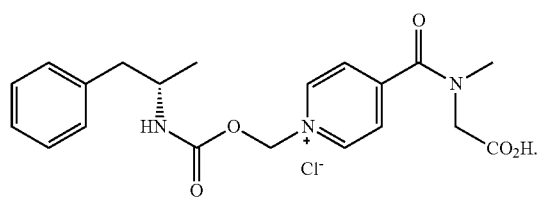

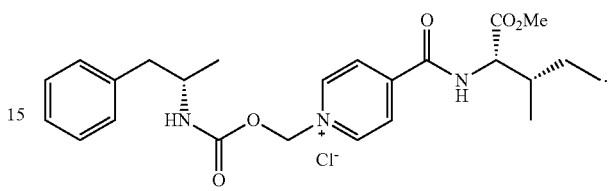

In some aspects, the compound is AMP-CO₂CH₂-isonicotinoyl-Leu or a salt thereof having the following structure:

In some aspects, the compound is AMP-CO₂CH₂-isonicotinoyl-Ala-OiPr or a salt thereof having the following structure:

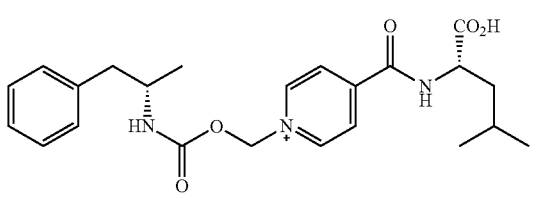

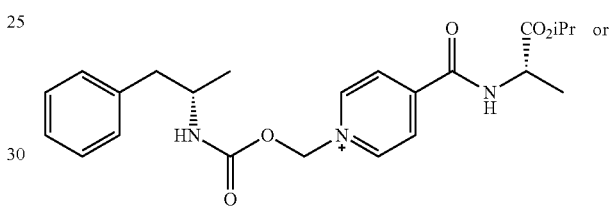

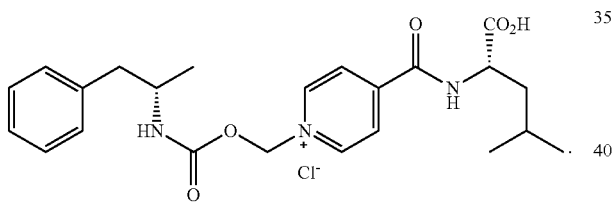

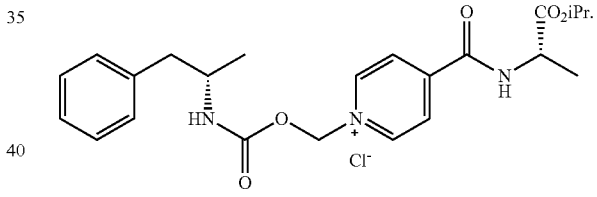

In some aspects, the compound is AMP-CO₂CH₂-isonicotinoyl-Pro or a salt thereof having the following structure:

In some aspects, the compound is AMP-CO₂CH₂-isonicotinoyl-Leu-NH₂ or a salt thereof having the following structure:

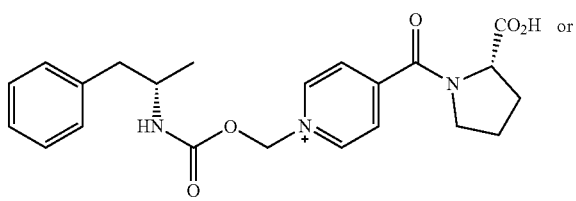

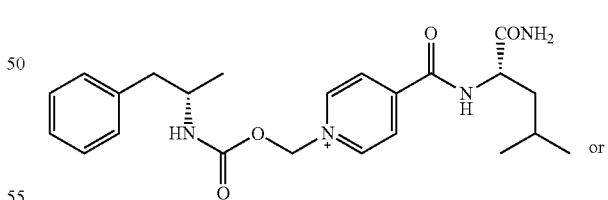

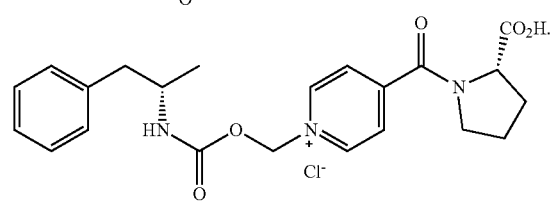

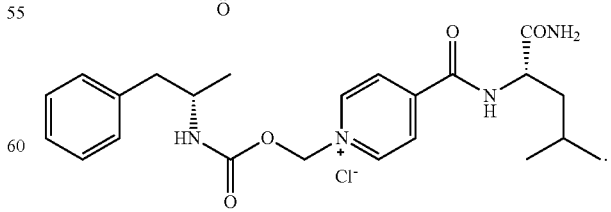

In some aspects, the compound is AMP-CO₂CH₂-isonicotinoyl-Ile-OMe or a salt thereof having the following structure:

In some aspects, the compound is AMP-CO₂CH₂-isonicotinoyl-Leu-OMe or a salt thereof having the following chemical structure:

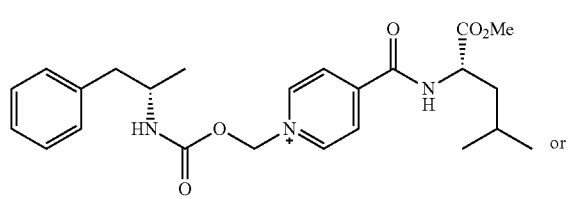

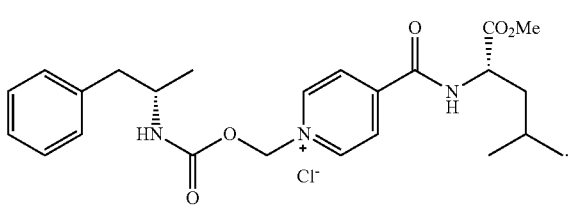

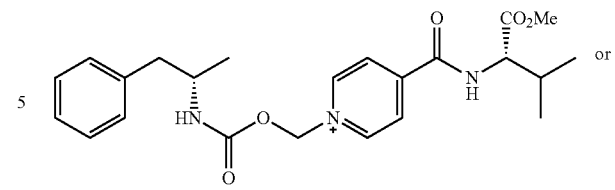

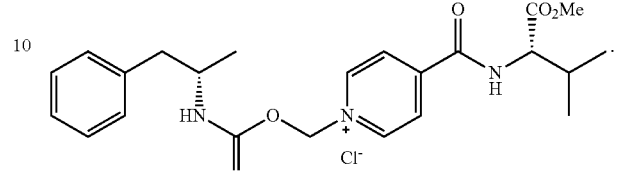

In some aspects, the compound is AMP-CO$_2$CH$_2$-isonicotinoyl-Asp or a salt thereof having the following structure:

In some aspects, the compound is AMP-CO$_2$CH$_2$-isonicotinoyl-Ala or a salt thereof having the following structure:

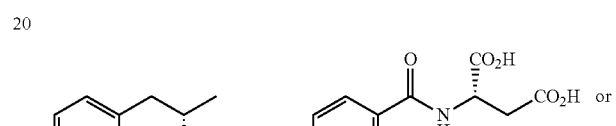

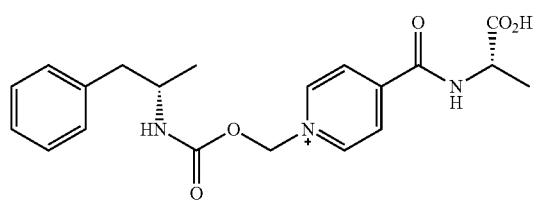

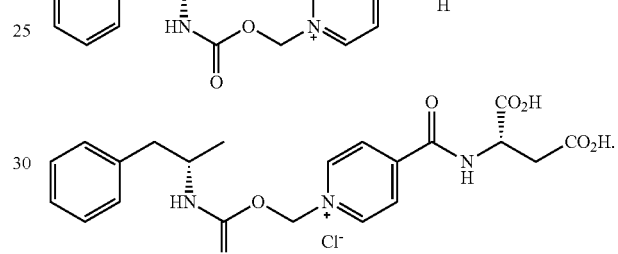

In some aspects, the compound is AMP-CO$_2$CH$_2$-isonicotinoyl-Ser or a salt thereof having the following structure:

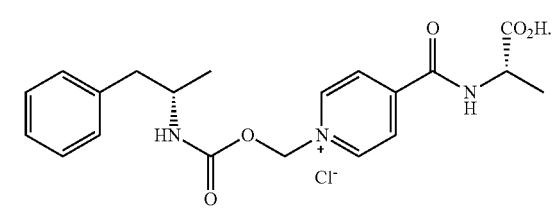

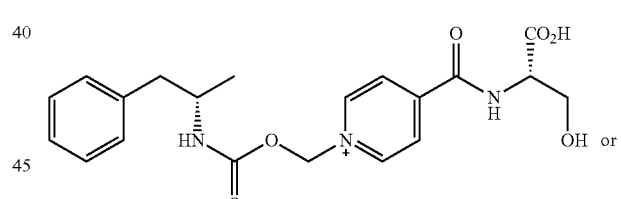

In some aspects, the compound is AMP-CO$_2$CH$_2$-isonicotinoyl-Orn or a salt thereof having the following structure:

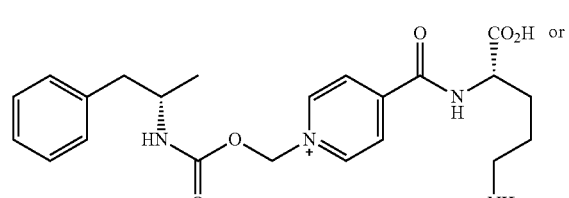

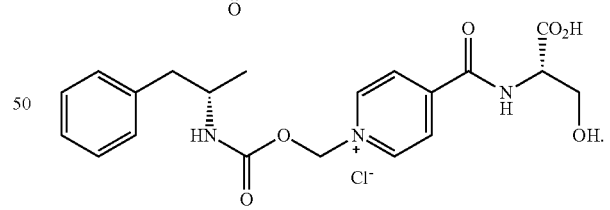

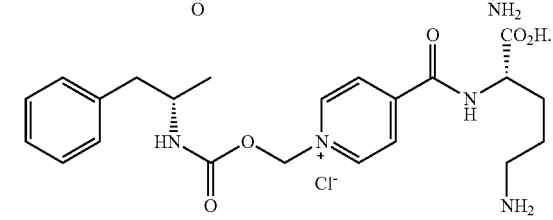

In some aspects, the compound is AMP-CO$_2$CH$_2$-isonicotinoyl-Val or a salt thereof having the following structure:

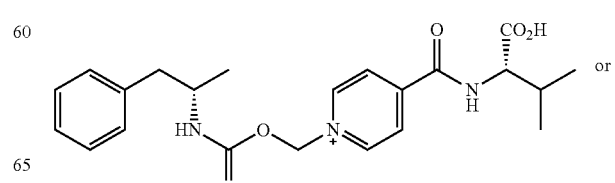

In some aspects, the compound is AMP-CO$_2$CH$_2$-isonicotinoyl-Val-OMe or a salt thereof having the following structure:

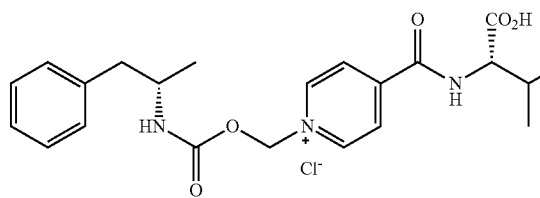

In some aspects, the compound is AMP-CO₂CH₂-isonicotinoyl-N-Me-Ala or a salt thereof having the following structure:

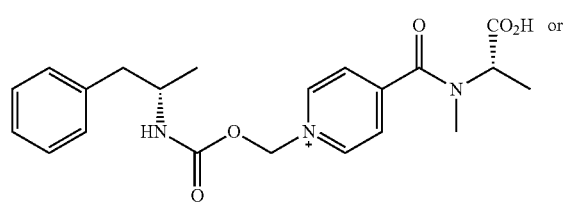

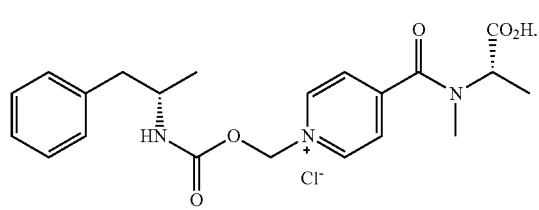

In some aspects, the compound is AMP-CO₂CH₂-isonicotinoyl-Glu or a salt thereof having the following structure:

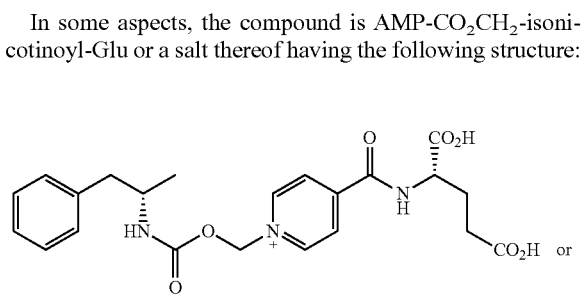

In some aspects, the compound is AMP-CO₂CH₂-isonicotinoyl-Gly-Ala or a salt thereof having the following structure:

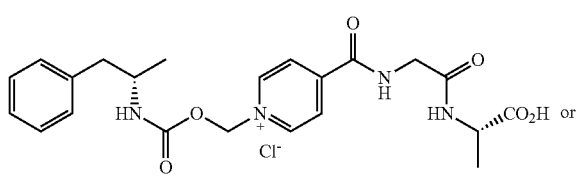

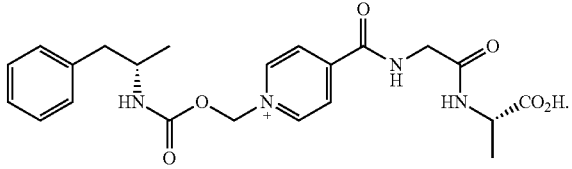

In some aspects, the compound is AMP-CO₂CH₂-isonicotinoyl-Phe or a salt thereof having the following structure:

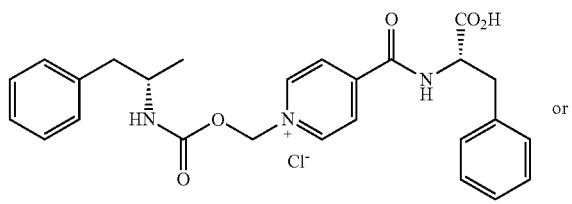

In some aspects, the compound is AMP-CO2CH2-picolinate(Me) or a salt thereof having the following structure:

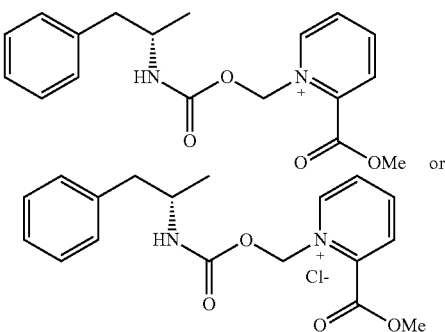

In some aspects, the pharmaceutically acceptable salt of the compound is a single salt or a mixed salt, where the one or more of the salts are selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

In some aspects, the compound is a conjugate of d-amphetamine and has the structure of Formula IA

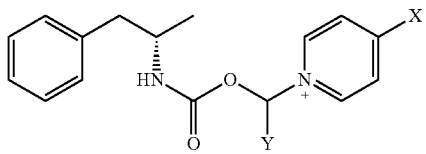

Formula IA where X is A-COO—R;

where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the compound is a conjugate of d-amphetamine and has the structure of Formula IC

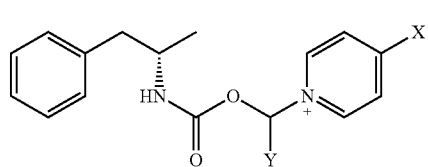

Formula IC where X is A-CO—NR$^1$R$^2$;

where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R$^1$ and R$^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the compound is a conjugate of d-amphetamine and has the structure of Formula IIA

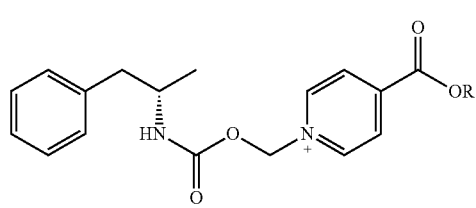

Formula IIA where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the compound is a conjugate of d-amphetamine and has the structure of Formula IIC:

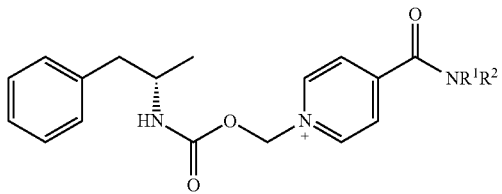

Formula IIC where Y is hydrogen, A is absent, and where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

In some aspects, the compound is a conjugate of d-amphetamine has the structure of IIE:

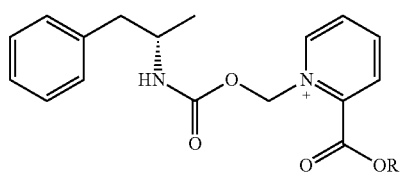

where R is independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound is a conjugate of d-amphetamine has the structure of Formula IIF:

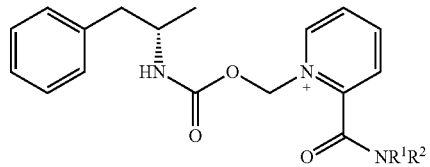

where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, polyethylene glycol, amino acid, and amino acid residue.

In some aspects, the compound is a conjugate of d-amphetamine and has the structure of Formula I

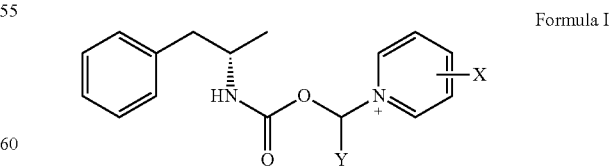

Formula I or a pharmaceutically acceptable salt thereof, where X is selected from the group consisting of an ester, carboxylic acid, amino acid, amino acid residue, amide group, and a derivative thereof, and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle.

In some aspects, the conjugate is AMP-CO$_2$CH$_2$-isonicotinate or salt thereof having the following structure:

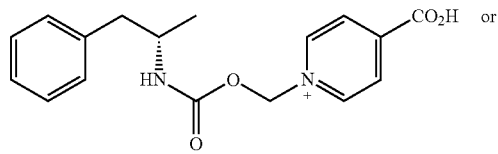

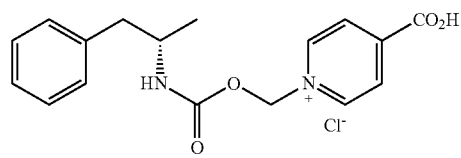

In some aspects, the conjugate is AMP-CO$_2$CH$_2$-isonicotinate(tBu) or a salt thereof having the following structure:

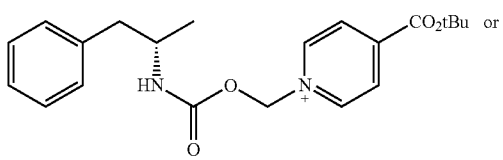

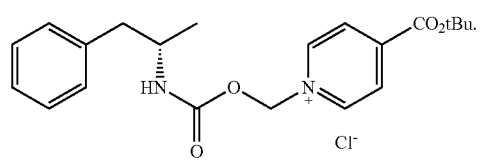

In some aspects, the conjugate is AMP-CO$_2$CH$_2$-isonicotinoyl-morpholine or a salt thereof having the following structure:

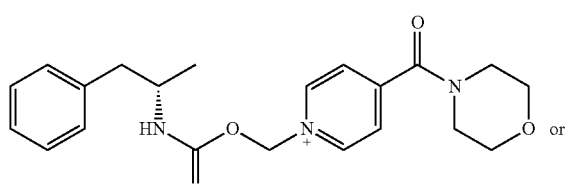

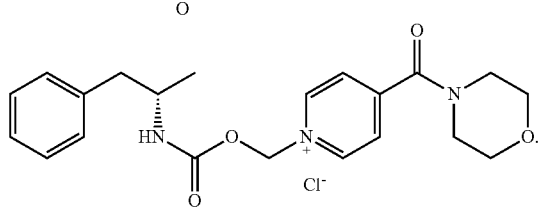

In some aspects, the conjugate is AMP-CO$_2$CH$_2$-isonicotinoyl-Val-NH$_2$ or a salt thereof having the following structure:

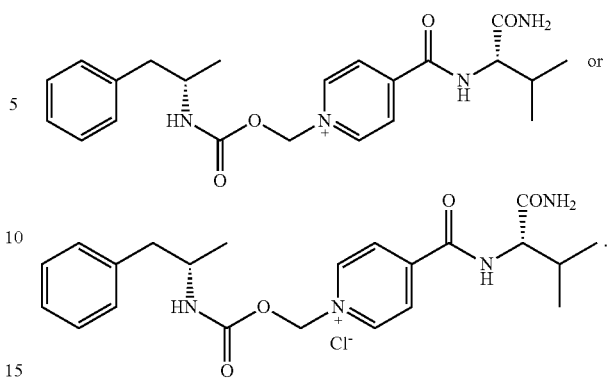

In some aspects, the conjugate is AMP-CO$_2$CH$_2$-isonicotinoyl-Ile or a salt thereof having the following structure:

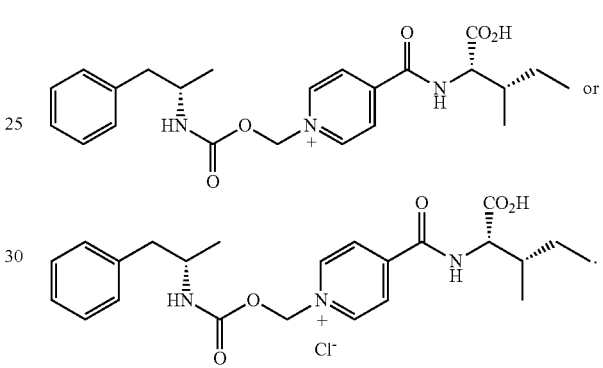

In some aspects, the conjugate is AMP-CO$_2$CH$_2$-isonicotinoyl-Thr or a salt thereof having the following structure:

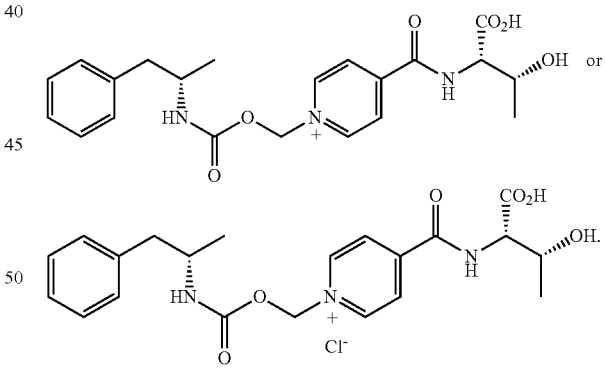

In some aspects, the conjugate is AMP-CO$_2$CH$_2$-isonicotinoyl-Gly or a salt thereof having the following structure:

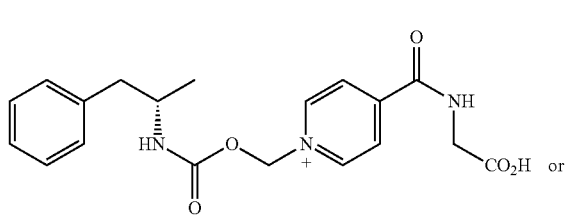

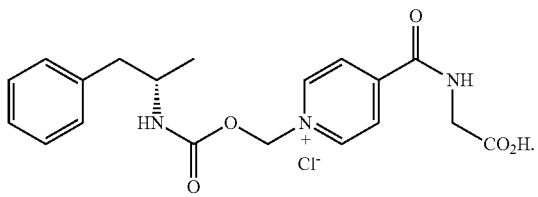

In some aspects, the conjugate is AMP-CO$_2$CH$_2$-isonicotinoyl-Sar or a salt thereof having the following structure:

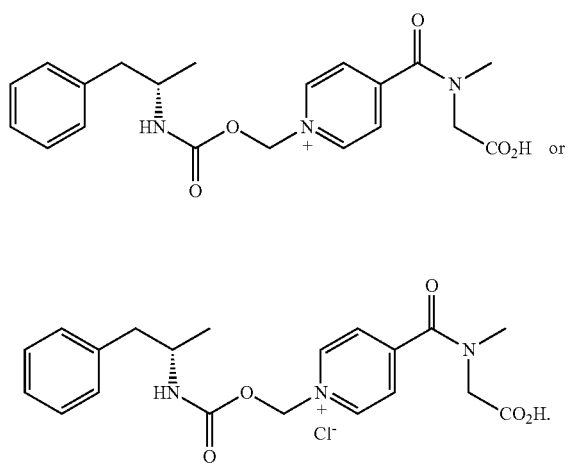

In some aspects, the conjugate is AMP-CO$_2$CH$_2$-isonicotinoyl-Leu or a salt thereof having the following structure:

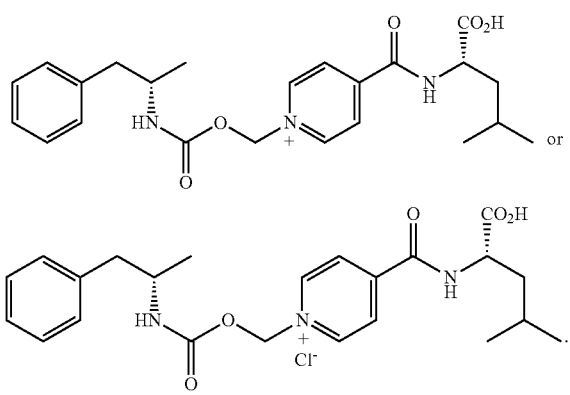

In some aspects, the conjugate is AMP-CO$_2$CH$_2$-isonicotinoyl-Pro or a salt thereof having the following structure:

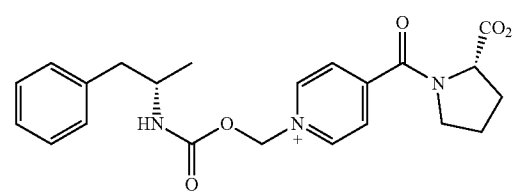

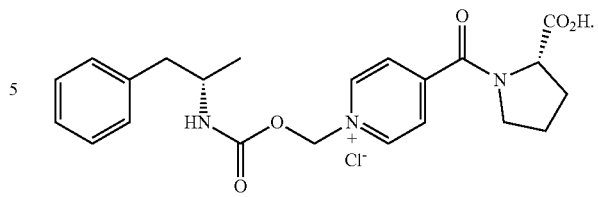

In some aspects, the conjugate is AMP-CO$_2$CH$_2$-isonicotinoyl-Ile-OMe or a salt thereof having the following structure:

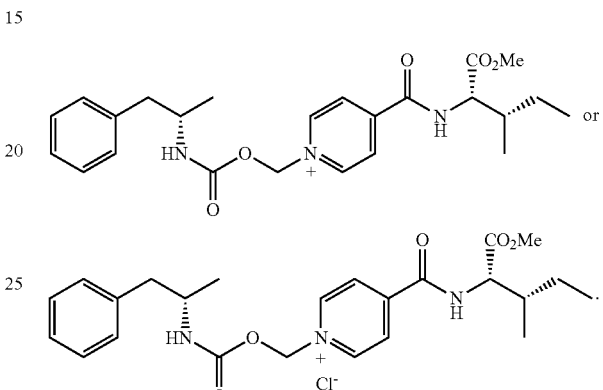

In some aspects, the conjugate is AMP-CO$_2$CH$_2$-isonicotinoyl-Ala-OiPr or a salt thereof having the following structure:

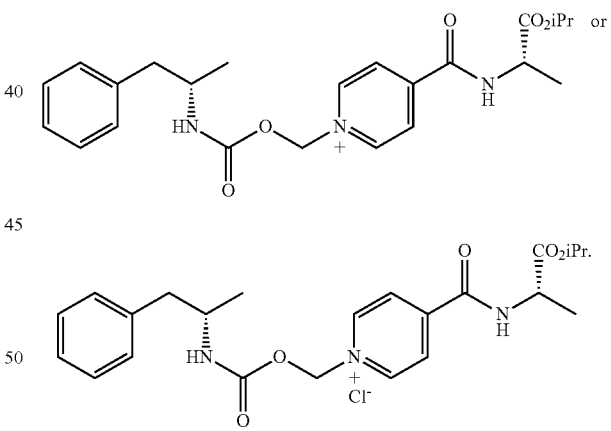

In some aspects, the conjugate is AMP-CO$_2$CH$_2$-isonicotinoyl-Leu-NH$_2$ or a salt thereof having the following structure:

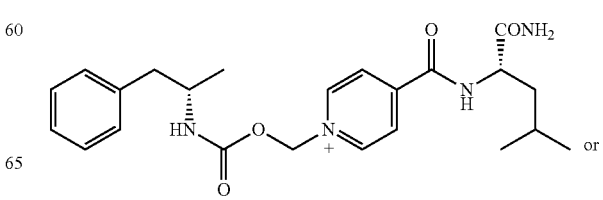

31
-continued

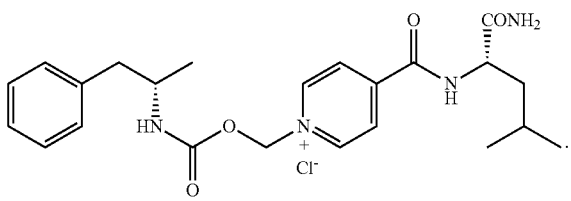

In some aspects, the conjugate is AMP-CO₂CH₂-isonicotinoyl-Leu-OMe or a salt thereof having the following chemical structure:

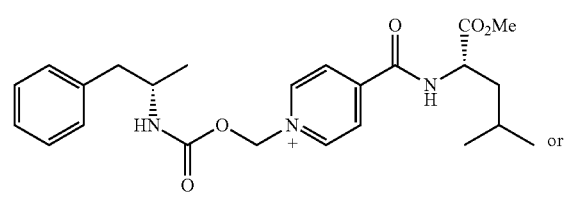

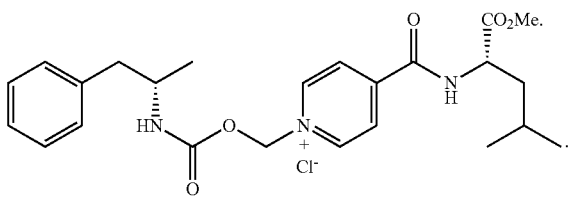

In some aspects, the conjugate is AMP-CO₂CH₂-isonicotinoyl-Ala or a salt thereof having the following structure:

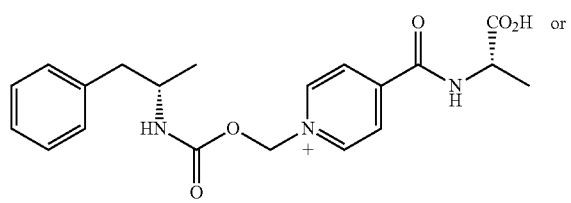

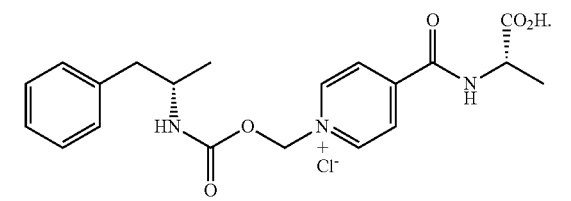

In some aspects, the conjugate is AMP-CO₂CH₂-isonicotinoyl-Orn or a salt thereof having the following structure:

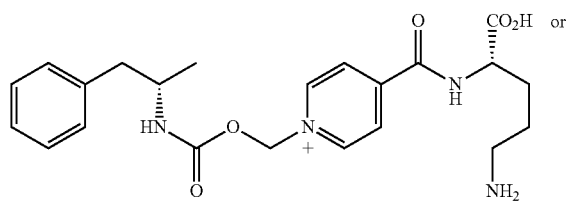

32
-continued

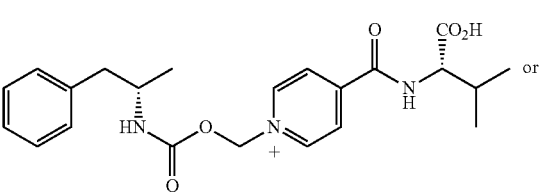

In some aspects, the conjugate is AMP-CO₂CH₂-isonicotinoyl-Val-OMe or a salt thereof having the following structure:

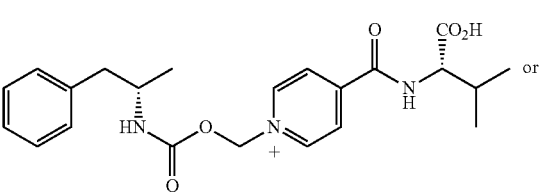

In some aspects, the conjugate is AMP-CO₂CH₂-isonicotinoyl-Asp or a salt thereof having the following structure:

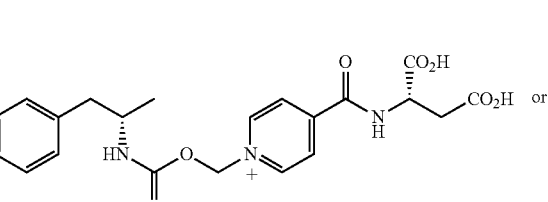

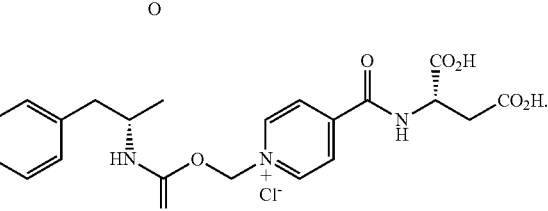

In some aspects, the conjugate is AMP-CO₂CH₂-isonicotinoyl-Ser or a salt thereof having the following structure:

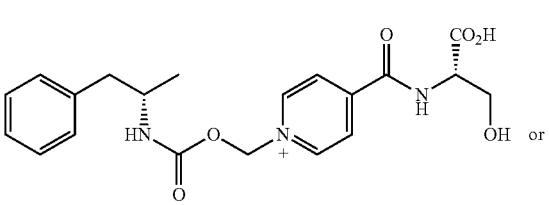

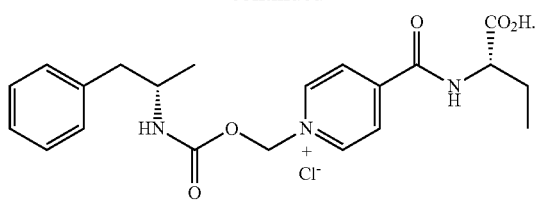

In some aspects, the conjugate is AMP-CO$_2$CH$_2$-isonicotinoyl-Val or a salt thereof having the following structure:

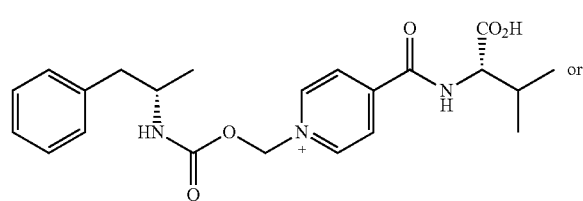

In some aspects, the conjugate is AMP-CO$_2$CH$_2$-isonicotinoyl-N-Me-Ala or a salt thereof having the following structure:

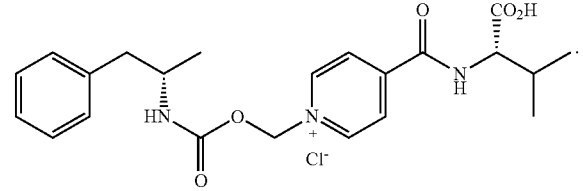

In some aspects, the conjugate is AMP-CO$_2$CH$_2$-isonicotinoyl-Glu or a salt thereof having the following structure:

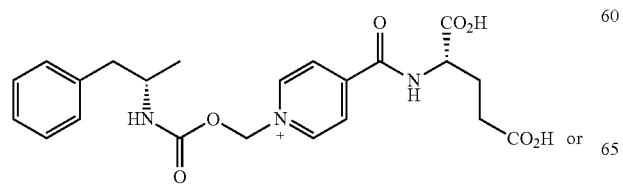

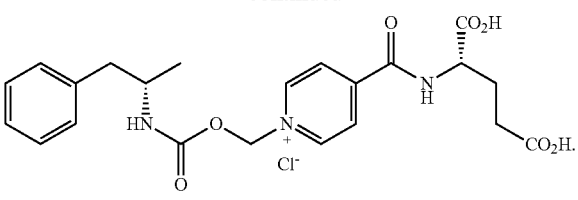

In some aspects, the conjugate is AMP-CO$_2$CH$_2$-isonicotinoyl-Gly-Ala or a salt thereof having the following structure:

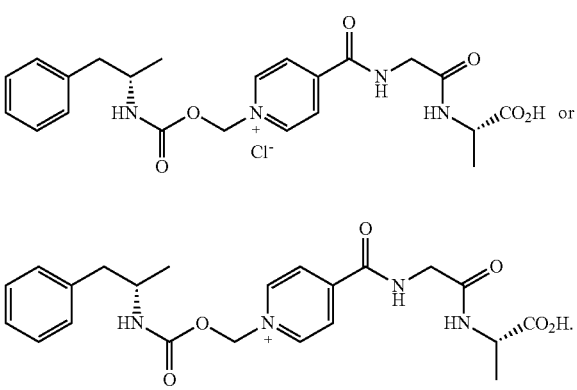

In some aspects, the conjugate is AMP-CO$_2$CH$_2$-isonicotinoyl-Phe or a salt thereof having the following structure:

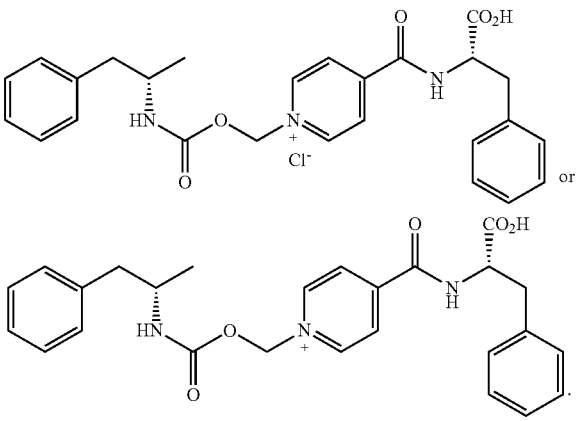

In some aspects, the conjugate is AMP-CO$_2$CH$_2$-picolinate(Me) or a salt thereof having the following structure:

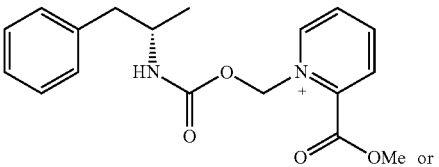

-continued

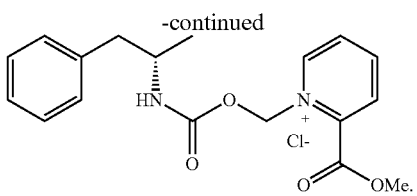

In some aspects, the pharmaceutically acceptable salt of the conjugate is a single salt or a mixed salt, where the one or more salts are selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

In some aspects, the amphetamine portion of the conjugate can be d-amphetamine or l-amphetamine. In other aspects, the compositions of the present technology comprise a mixture of conjugates of d-amphetamine and conjugates of l-amphetamine. In further aspects, the mixture of conjugates may be a racemic mixture. It should be appreciated that portions of the conjugates other than amphetamine can also have chiral centers that create additional stereoisomers. The compositions of this technology can comprise single stereoisomers or any mixture of stereoisomers.

In some aspects, the X of the compound or the conjugate is located at the C-2 or C-4 position of the pyridine ring. In further aspects, two or more independently selected X are attached to the pyridine ring at the C-2, C-3, C-4, C-5, and/or C-6 position. It should be appreciated that for symmetry reasons C-3 may be equivalent to C-5 and C-2 may be equivalent to C-6 for certain substitution patterns of X.

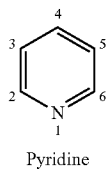

Pyridine

Some aspects are a composition comprising a conjugate of d-amphetamine. In some aspects, the composition is formulated for oral, suppository, powder for injection, intravenous, intranasal, or intrathecal administration. In yet another aspect, the composition formulated for oral administration is in a dosage form selected from the group consisting of solid form, a tablet, a capsule, a caplet, a soft gel, a suppository, a troche, a lozenge, an oral powder, a solution, a syrup, an oral film, a thin strip, a slurry, an emulsion, an elixir, and a suspension. In yet another aspect, the composition further comprises one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof. In yet a further aspect the binder is selected from the group consisting of hydroxypropylmethylcellulose, ethyl cellulose, povidone, acrylic and methacrylic acid co-polymers, pharmaceutical glaze, gums, gelatin, cellulose, cellulose derivatives, polyvinylpyrrolidone, starch, sucrose and polyethylene glycol, and milk derivatives.

In some aspects, the conjugate is present in an amount per unit dose of between about 0.1 mg and about 2000 mg per unit dose. In yet another aspect, the conjugate is present in an amount per unit dose of between about 0.1 mg and about 1000 mg per unit dose. In another aspect, the conjugate is present in an amount per unit dose of between about 0.5 mg and about 500 mg per unit dose. In a further aspect, the conjugate is present in an amount per unit dose of between about 1 mg and about 250 mg per unit dose. In yet another aspect, the conjugate is present in an amount per unit dose of between about 1.5 mg and about 100 mg per unit dose. In yet another aspect, the conjugate is present in an amount per unit dose of between about 0.5 mg and about 2000 mg per unit dose, alternatively about 1 mg and about 2000 mg per unit dose, alternatively about 2 mg and about 2000 mg per unit dose, alternatively about 5 mg and about 2000 mg per unit dose, alternatively about 10 mg and about 2000 mg per unit dose, alternatively about 20 mg and about 2000 mg per unit dose, alternatively about 40 mg and about 2000 mg per unit dose, alternatively about 80 mg and about 2000 mg per unit dose, alternatively about 160 mg and about 2000 mg per unit dose, alternatively about 320 mg and about 2000 mg per unit dose, alternatively about 640 mg and about 2000 mg per unit dose, alternatively about 1280 mg and about 2000 mg per unit dose, In yet another aspect, the conjugate is present in an amount per unit dose of between about 0.1 mg and 2000 mg per unit does, alternatively about 0.1 mg and about 1900 mg per unit dose, alternatively about 0.1 mg and about 1800 mg per unit dose, alternatively about 0.1 mg and about 1700 mg per unit dose, alternatively about 0.1 mg and about 1600 mg per unit dose, alternatively about 0.1 mg and about 1500 mg per unit dose, alternatively about 0.1 mg and about 1400 mg per unit dose, alternatively about 0.1 mg and about 1300 mg per unit dose, alternatively about 0.1 mg and about 1200 mg per unit dose, alternatively about 0.1 mg and about 1100 mg per unit dose, alternatively about 0.1 mg and about 1000 mg per unit dose, alternatively about 0.1 mg and about 900 mg per unit dose, alternatively about 0.1 mg and about 800 mg per unit dose, alternatively about 0.1 mg and about 700 mg per unit dose, alternatively about 0.1 mg and about 600 mg per unit dose, alternatively about 0.1 mg and about 500 mg per unit dose, alternatively about 0.1 mg and about 400 mg per unit dose, alternatively about 0.1 mg and about 300 mg per unit dose, alternatively about 0.1 mg and about 200 mg per unit dose, alternatively about 0.1 mg and about 100 mg per unit dose, alternatively about 0.1 mg and about 90 mg per unit dose, alternatively about 0.1 mg and about 80 mg per unit dose, alternatively about 0.1 mg and about 70 mg per unit dose, alternatively about 0.1 mg and about 60 mg per unit dose, alternatively about 0.1 mg and about 50 mg per unit dose, alternatively about 0.1 mg and about 40 mg per unit dose, alternatively about 0.1 mg and about 30 mg per unit dose, alternatively about 0.1 mg and about 20 mg per unit dose, alternatively about 0.1 mg and about 10 mg per unit dose, alternatively about 0.1 mg and about 5 mg per unit dose, and alternatively about 0.1 mg and about 1 mg per unit dose.

In some aspects the composition further comprises one or more additional pharmacological substance selected from the group consisting of stimulants, anti-depressants, combinations thereof and prodrugs thereof. In another aspect, the composition further comprises one of more of unconjugated amphetamine, unconjugated methylphenidate, aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, or ziprasidone. In another aspect, the composition furthers comprises unconjugated amphetamine, an isomer thereof, or an amphetamine conjugate. In yet a further aspect, the isomer of unconjugated amphetamine is unconjugated d-amphetamine. In another aspect, the composition further comprises unconjugated methylphenidate, an isomer thereof, or a methylphenidate conjugate. In yet a further aspect, the isomer of unconjugated methylphenidate is unconjugated d-methylphenidate. In a further aspect, the conjugate of methylphenidate is serdexmethylphenidate.

In some aspects, the conjugate is provided in an amount sufficient to provide a similar or decreased AUC when compared to unconjugated d-amphetamine when orally administered at equimolar doses. In some aspects, the conjugate is provided in an amount sufficient to provide a similar or decreased $C_{max}$ as compared to unconjugated d-amphetamine when administered orally at equimolar doses. In yet another aspect, the conjugate is provided in an amount sufficient to provide a decreased $C_{max}$ and a similar or decreased AUC as compared to unconjugated d-amphetamine when administered orally at equimolar doses. In yet another aspect, intranasal or intravenous administration of the at least one conjugate provides a lower AUC and/or Cmax when compared to an equivalent molar amount of unconjugated d-amphetamine. In another aspect, the composition comprising the conjugate is provided in an amount sufficient to provide a longer $T_{max}$ when compared to unconjugated d-amphetamine when administered orally at equimolar doses. In another aspect, the composition comprising the conjugate is provided in an amount sufficient to provide a similar $T_{max}$ when compared to unconjugated d-amphetamine when administered orally at equimolar doses.

In some aspects, the composition comprising the conjugate provides reduced abuse potential as compared to unconjugated d-amphetamine. In another aspect, the composition comprising the conjugate is provided in an amount sufficient to provide a longer $T_{max}$ when compared to unconjugated d-amphetamine when administered at equimolar doses. In another aspect, the composition comprising the conjugate is provided in an amount sufficient to provide a similar $T_{max}$ when compared to unconjugated d-amphetamine when administered at equimolar doses. In yet another aspect the composition comprising the conjugate has an improved safety profile when compared to unconjugated d-amphetamine. In some aspects, the composition comprising the conjugate produces reduced or insignificant pharmacological activity when administered by parenteral routes. In yet another aspect, the composition comprising the conjugate has a reduced plasma or blood concentration of released d-amphetamine when administered intranasally or intravenously as compared to unconjugated d-amphetamine when administered in equimolar amounts.

In some aspects, the composition comprising the conjugate provides a lower AUC and/or $C_{max}$ for d-amphetamine released from the conjugate when compared to an equivalent molar amount of unconjugated d-amphetamine following intravenous or intranasal administration of the composition to a subject. In another aspect, the composition comprising the conjugate provides a longer $T_{max}$ for d-amphetamine released from the conjugate when compared to an equivalent molar amount of unconjugated d-amphetamine following intravenous or intranasal administration of the composition to a subject. In some aspects, upon administration to a subject, the composition comprising the conjugate results in an extended release of d-amphetamine in the subject compared to the release of d-amphetamine upon administration of an equivalent molar amount of unconjugated d-amphetamine. In yet another aspect the composition comprising the conjugate exhibits less variability in inter-subject or intra-subject d-amphetamine plasma concentrations when compared to unconjugated d-amphetamine.

Another aspect of the present technology is a composition for treating a patient having a disorder or condition requiring stimulation of the central nervous system of the patient, wherein the composition has reduced abuse potential when administered compared to unconjugated d-amphetamine.

Another aspect of the present technology is a method of treating a patient having a disease, disorder or condition mediated by controlling, preventing, limiting, or inhibiting neurotransmitter uptake, the method comprising administering to a patient in need thereof a pharmaceutically effective amount of the composition comprising a conjugate of the current invention.

Another aspect of the present technology is a method of treating a patient having a disease, disorder or condition mediated by increasing neurotransmitter concentrations in the synapse, the method comprising administering to a patient in need thereof a pharmaceutically effective amount of the composition comprising a conjugate of the current invention.

Another aspect of the present technology is a method of treating a patient having a disorder or condition requiring stimulation of the central nervous system of the patient, the method comprising orally administering to a patient in need thereof a pharmaceutically effective amount of the composition comprising a conjugate of the current invention. In some aspects, the disease or condition is attention-deficit hyperactivity disorder, attention deficit disorder, autistic spectrum disorder, autism, Asperger's disorder, pervasive developmental disorder, sleep disorder, obesity, depression, bipolar disorder, eating disorder, binge eating, chronic fatigue syndrome, excessive daytime sleepiness, insomnia, schizophrenia, major depressive disorder, narcolepsy, postural orthostatic tachycardia syndrome, Tourette syndrome, nervous tics, substance use disorder, lethargy, depression, neural insult or obesity. In yet another aspect, the disease or condition is attention-deficit hyperactivity disorder. In yet another aspect, the disease or condition is Tourette syndrome or nervous tics.

As a person of ordinary skill in the art will understand, drug products are considered pharmaceutical equivalents if they contain the same active ingredient(s), are of the same dosage form, route of administration, and are identical in strength or concentration. Pharmaceutically equivalent drug products are formulated to contain the same amount of active ingredient in the same dosage form and to meet the same or compendial or other applicable standards (i.e., strength, quality, purity, and identity), but they may differ in characteristics such as shape, scoring configuration, release mechanisms, packaging, excipients (including colors, flavors, preservatives), expiration time, and, with certain limits, labeling. Drug products are considered to be therapeutic equivalents only if they are pharmaceutical equivalents and if they can be expected to have the same clinical effect and safety profile when administered to patients under the conditions specified in the labeling. The term "bioequivalent," on the other hand, describes pharmaceutical equivalent or pharmaceutical alternative products that display comparable bioavailability when studied under similar experimental conditions.

In accordance with the presently described technology, release of d-amphetamine after oral administration of the compounds of the presently described technology would occur under desired physiological conditions. Preferably, other routes of administration (e.g., intranasal or intravenous) do not break the compound down to any appreciable extent. In some aspects, reduction in d-amphetamine exposure following intranasal and/or intravenous administration is 50%, 30%, 20%, <10%, etc. of the exposure following intranasal and/or intravenous administration of an equimolar dose of unconjugated d-amphetamine. Also, preferably certain compounds or aspects of the present invention will resist release of amphetamine via external means (chemical, enzymatic, or other). The breakdown ratio of the compound that can be achieved through external means is preferably less than about 50%, alternatively less than about 25%, alternatively less than about 20%, alternatively less than about 10%.

Embodiments of the compounds, compositions, and methods of the presently described technology are also believed to provide reduced potential for rebound, reduced potential for abuse or addiction, and/or improve d-amphetamine's stimulant related toxicities.

The d-amphetamine compounds of the presently described technology could be used for any condition requiring the stimulation of the central nervous system (CNS). These conditions include, for example, attention deficit hyperactivity disorder (ADHD), attention deficit disorder (ADD), obesity, narcolepsy, appetite suppressant, depression, anxiety, and wakefulness. D-amphetamine stimulants have also demonstrated usefulness in treating stimulant (e.g., cocaine, methamphetamine) abuse and addiction. D-amphetamine stimulants have also been used extensively to improve battlefield alertness and to combat fatigue.

Therefore, in accordance with some aspects, the presently described technology provides d-amphetamine compositions comprising at least one d-amphetamine compound of the present technology.

One aspect is a composition that can prevent behavioral deterioration caused by d-amphetamine dosing, comprising the d-amphetamine compound of the present technology.

Another aspect is a composition that allows for lower doses of an active pharmaceutical ingredient comprising the d-amphetamine compound of the present technology.

Other formulations according to one or more aspects of the present technology may further comprise pharmaceutical additives including, but not limited to, lubricants such as magnesium stearate, calcium stearate, zinc stearate, powdered stearic acid, hydrogenated vegetable oils, talc, polyethylene glycol, and mineral oil; colorants such as Emerald Green Lake, FD&C Red No. 40, FD&C Yellow No. 6, D&C Yellow No. 10, or FD&C Blue No. 1 and other various certified color additives (See 21 CFR, Part 74); binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quaternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art.

The d-amphetamine compositions of the present technology may be manufactured according to any appropriate method known to those of skill in the art of pharmaceutical manufacture.

It should be noted that the above additives are not required for the d-amphetamine composition of the present technology to have sustained release in vivo properties. The d-amphetamine compounds of the present technology are chemically stable to prevent tampering or removing the d-amphetamine prior to oral ingestion. Also, the controlled release of d-amphetamine through oral administration of the d-amphetamine compound of the present technology is a designed property of the molecule and not related to the formulation. Therefore, the compound of the present technology can be easily formulated to different dosage forms. In one or more aspects of the present technology, no further sustained release additives are required to achieve a blunted or reduced pharmacokinetic curve (e.g., reduced euphoric effect) while achieving therapeutically effective amounts of d-amphetamine release when taken orally.

The compounds and compositions of the presently described technology can be formulated into and administered by a variety of dosage forms through any oral routes of delivery. Once administered, the compound will release d-amphetamine under digestive conditions. Any biologically-acceptable dosage form known to persons of ordinary skill in the art, and combinations thereof, are contemplated. Examples of preferred dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, oral films (e.g., fast dissolving thin strips), and combinations thereof.

Formulations of the present technology suitable for oral administration can be presented as discrete units, such as capsules, caplets, tablets, or oral films. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow.

If the capsule form is chosen, for example, excipients used in the capsule formulation could be broken up into four separate groups: bulk agent/binder, disintegrant, lubricant, and carrier. Soft gel or soft gelatin capsules may be prepared, for example, by dispersing the formulation of the present technology in an appropriate vehicle (vegetable oils are commonly used) to form a high viscosity mixture. This mixture can then be encapsulated with a gelatin-based film using technology and machinery known to those in the soft gel industry. The industrial units so formed are then dried to constant weight.

Chewable tablets, for example, may be prepared by mixing the formulations of the present technology with excipients designed to form a relatively soft, flavored, tablet dosage form that is intended to be chewed rather than swallowed. Conventional tablet machinery and procedures that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film-coated tablets, for example, may be prepared by coating tablets using techniques such as rotating pan coating methods or air suspension methods to deposit a contiguous film layer on a tablet.

Compressed tablets, for example, may be prepared by mixing the formulation of the present technology with excipients intended to add binding qualities to disintegration qualities. The mixture can be either directly compressed or granulated then compressed using methods and machinery known to those in the industry. The resultant compressed tablet dosage units are then packaged according to market need, i.e., unit dose, rolls, bulk bottles, blister packs, etc.

Methods and other ingredients needed to make oral films or thin strips are known in the art. Potential film forming agents include pullulan, hydroxypropylmethyl cellulose, hydroxypropyl cellulose, polyvinyl pyrrolidone, polyvinyl alcohol, sodium alginate, polyethylene glycol, xanthan gum, tragacanth gum, guar gum, acacia gum, Arabic gum, polyacrylic acid, amylase, starch, dextrin, pectin, chitin, chitosan, levan, elsinan, collagen, gelatin, zein, gluten, soy protein isolate, whey protein isolate, casein, and mixtures thereof.

Also, saliva stimulating agents, plasticizing agents, cooling agents, surfactants, emulsifying agents, thickening agents, binding agents sweeteners, flavoring, coloring agents, preservatives, or taste masking resins may be employed in the oral films or thin strips. Preferred agents include pullulan, triethanol amine stearate, methyl cellulose, starch, triacetin, Polysorbate 80, xanthan gum, maltitol, sorbitol, and glycerol.

The presently described technology also contemplates the use of biologically-acceptable carriers which may be prepared from a wide range of materials. Without being limited thereto, such materials include diluents, binders, and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate, and castor oil are used to delay the release of water-soluble vitamins, such as vitamin $B_6$ and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of the present technology can include other suitable agents such as flavoring agents, preservatives and antioxidants. Such antioxidants would be food acceptable and could include, for example, vitamin E, carotene, BHT or other antioxidants known to those of skill in the art.

Other compounds which may be included are, for example, medically inert ingredients, e.g., solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. The suspensions and the emulsions may contain a carrier, for example, a natural gum, agar, sodium alginate, pectin, methylcellulose, carboxymethylcellulose or polyvinyl alcohol.

The dose range for adult human beings will depend on a number of factors including the age, weight, and condition of the patient. Suitable oral dosages of the compositions of the presently described technology can be the equivalents of those typically found in d-amphetamine treatments. Typical dosages for d-amphetamine salts can range from about 1 mg to about 500 mg, alternatively from about 1 mg to about 400 mg, alternatively from about 1 mg to about 300 mg, alternatively from about 1 mg to about 200 mg, alternatively from about 1 mg to about 100 mg, although higher dosages may be approved at later dates.

Tablets, capsules, oral films, and other forms of presentation provided in discrete units conveniently contain a daily dose, or an appropriate fraction thereof, of one or more of the compounds of the invention.

It is also possible for the dosage form of the present technology to combine any forms of release known to persons of ordinary skill in the art. These conventional release forms include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof are known in the art.

Compositions of the present technology may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the present technology may be provided in a blister pack or other such pharmaceutical package. Further, the compositions of the present technology may further include or be accompanied by indicia allowing individuals to identify the compositions as products for a prescribed treatment. The indicia may additionally include an indication of the above specified time periods for administering the compositions. For example, the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the present technology can be demonstrated using standard pharmacological models that are known in the art. Furthermore, it will be appreciated that the compositions of the present technology can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

In one or more aspects of the present technology, the solubility and dissolution rate of the composition can be substantially changed under different physiological conditions encountered, for example, in the intestine, at mucosal surfaces, or in the bloodstream. In one or more aspects of the present technology, the solubility and dissolution rate of the composition can substantially decrease the bioavailability of the d-amphetamine, particularly at doses above those intended for therapy. In one aspect of the present technology, the decrease in bioavailability occurs upon intranasal administration. In another aspect, the decrease in bioavailability occurs upon intravenous administration.

The presently described technology further provides methods for altering and/or delivering amphetamines in a manner that can decrease their potential for abuse.

One aspect provides a method for preventing behavioral deterioration or the rebound effect by administering to a patient in need of a d-amphetamine composition of the present technology.

Another aspect of the present technology is a method for reducing or preventing abuse of d-amphetamine comprising providing, administering, consuming, or prescribing a composition to a patient in need thereof, wherein said composition comprises a d-amphetamine compound of the present invention such that the pharmacological activity of d-amphetamine is decreased when the composition is used in a manner inconsistent with the manufacturer's instructions.

Another aspect of the present technology is a method of preventing behavioral deterioration or the rebound effect of d-amphetamine or stimulant treatment comprising providing, administering, consuming, or prescribing an d-amphetamine composition of the presently described technology to a patient in need thereof, wherein said composition comprises a d-amphetamine compound of the present invention that can decrease the potential of behavioral deterioration or the rebound effect from d-amphetamine or stimulant treatment.

Another aspect of the present technology is any of the preceding methods wherein the d-amphetamine composition used is adapted for oral administration, and wherein the d-amphetamine is resistant to release d-amphetamine from the organic acid moiety when the composition is administered parenterally, such as intranasally or intravenously.

Another aspect of the present technology provides methods of treating various diseases or conditions requiring the stimulation of the central nervous system (CNS) comprising administering compounds or compositions of the present technology which, optionally, further comprise commonly prescribed active agents for the respective illness or disease.

In one aspect, the composition comprising a d-amphetamine compound, a salt thereof, or a combination thereof provides immediate and extended release PK profiles when compared to unconjugated d-amphetamine.

A further aspect of the present technology is a kit comprising individual doses of a therapeutically effective amount of a composition comprising a d-amphetamine compound, conjugate, a salt thereof, or a combination thereof. In some aspects, the kit is in a unit dose pack.

In one aspect of the present invention, the amphetamine conjugates, compounds, and/or compositions have increased d-amphetamine plasma concentration compared to lisdexamfetamine dimesylate (or alternatively amphetamine sulfate) following oral administration for at least 1 hour, or at least 2 hours, or at least 4 or at least 6 hours. In other aspects of present invention, the amphetamine conjugates, compounds, and/or composition have decreased d-amphetamine plasma concentrations compared to d-amphetamine sulfate and similar d-amphetamine plasma concentrations compared to lisdexamfetamine dimesylate following oral administration for at least 1 hour, or at least 2 hours, or at least 4 hours, or at least 6 hours. In another aspect of the present invention, the amphetamine conjugates, compounds, and/or compositions thereof the present invention have decreased d-amphetamine plasma concentrations following intravenous or intranasal administration compared to lisdexamfetamine dimesylate or amphetamine sulfate for at least 1 hour, or at least 2 hours, or at least 4 hours, or at least 6 hours.

The presently described technology and its advantages will be better understood by reference to the following examples and/or schemes. These examples and/or schemes are provided to describe specific aspects of the present technology. By providing these specific examples and/or schemes, the applicants do not limit the scope and spirit of the present technology.

General Synthetic Procedure:

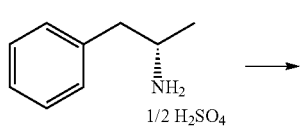

1

-continued

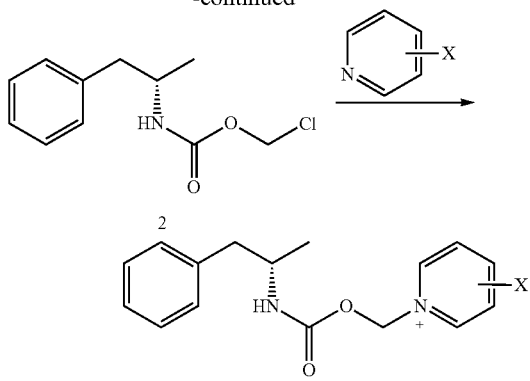

Amphetamine hemisulfate 1 was converted to chloromethyl carbamate 2 by adding chloromethyl chloroformate. The chloromethyl carbamate of amphetamine 2 and the respective pyridine derivative were heated in acetone or acetonitrile with or without NaI to give the amphetamine conjugate. A subsequent deprotection may be required if applicable.

Specific Procedures:

1. Synthesis of AMP-CO₂CH₂-isonicotinate 3a-e

TABLE 1

Structures of conjugates 3a-e

| Comp. | Structure |
|---|---|
| 3a | (structure with CO₂tBu) |
| 3b | (structure with CO₂Et) |
| 3c | (structure with CO₂Me) |
| 3d | (structure with CO₂i-Pr) |
| 3e | (structure with CO₂H) |

Scheme 1

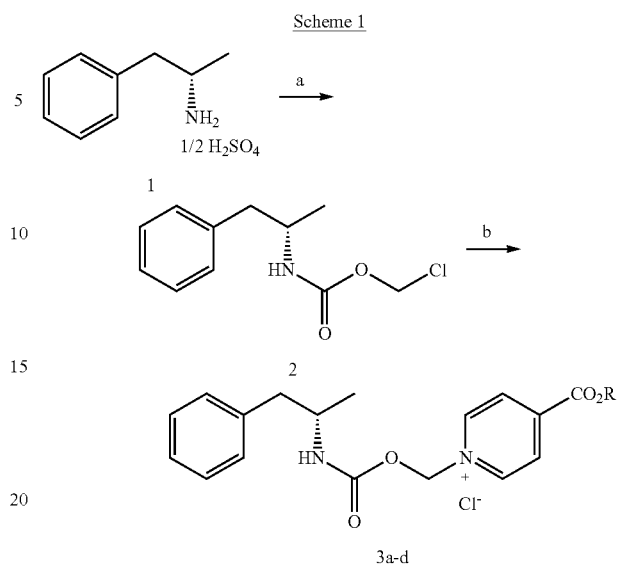

(a) ClCH₂COCl, DIPEA, DCM;
(b) isonicotinate, acetonitrile, 80-85° C.

a) Synthesis of AMP-CO₂—CH₂-isonicotinate(tBu) 3a and AMP-CO₂—CH₂-isonicotinate 3e

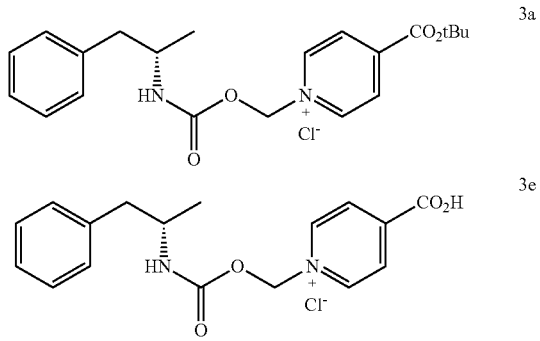

Step 1: Chloromethyl Carbamate of Amphetamine, ClCH₂OCO-AMP 2

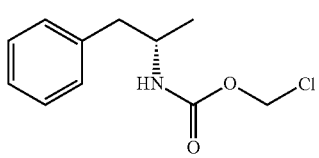

D-Amphetamine hemisulfate (4.640 g, 25.18 mmol) in DCM (80 mL) was cooled in ice-water bath. DIPEA (8.136 g, 62.95 mmol) was added. Then chloromethyl chloroformate (4.221 g, 32.74 mmol) in DCM (20 mL) was added over 15 min. The reaction was warmed up to room temperature over 30 min, then stirred for another 1.5 hr. Then, 5% of aq. NH₄Cl (40 mL) was added to quench the reaction. The DCM layer was separated and dried over sodium sulfate. The solvent was evaporated. The residue was purified by silica gel column chromatography (hexanes:ethyl acetate, 4:1) to give 4.9 g of 2 as syrup, which solidified when stored in the freezer. The yield was 85.5%.

Step 2: AMP-CO$_2$CH$_2$-isonicotinate(tBu) 3a:

The chloromethyl carbamate of amphetamine 2 (0.342 g, 1.5 mmol) and t-butyl isonicotinate (0.806 g, 4.5 mmol) in acetonitrile (10 mL) were heated at 80-85° C. for 8 hr. The solvent was evaporated. The residue was dissolved in DCM (1.5 mL) and TBME (60 mL) was added. The upper layer was decanted. The remaining syrup was treated using the above procedure twice, then was dried over vacuum to give 0.462 g of an amorphous solid. The yield was 76%.

Step 3: AMP-CO$_2$—CH$_2$-isonicotinic Acid 3e

Scheme 2

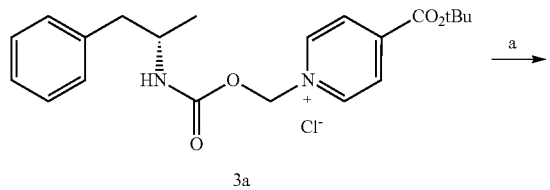

3a

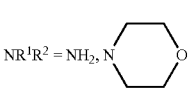

(a) 4M HCl/dioxane 3a (0.300 g, 0.74 mmol) in 4 M HCl/dioxane (8 mL) was stirred for 21 hr. The solvent was evaporated to give a solid which was subsequently co-evaporated with DCM (15 mL×2) and dried over vacuum. The resulting solid was dissolved in ethanol (5.5 mL) and TBME (15 mL) was added. The precipitate that formed was collected after 4 hr. washed with TBME/ethanol (4:1, 1 mL×3), and dried over vacuum. 0.146 g of solid was obtained and the yield was 56%.

b) Conjugates 3b-d were Made by the Similar Synthetic Methods as 3a

2. Synthesis of AMP-CO$_2$CH$_2$-isonicotinamide 4a and 4b

Scheme 3

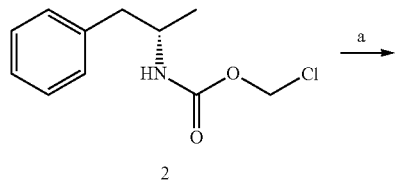

2

-continued 4a-b

NR$^1$R$^2$ = NH$_2$, N-morpholine (a) nicotinamide, NaI, acetone, then Dowex 1 × 8 a) Synthesis of AMP-CO$_2$CH$_2$-isonicotinoylmorpholine 4b

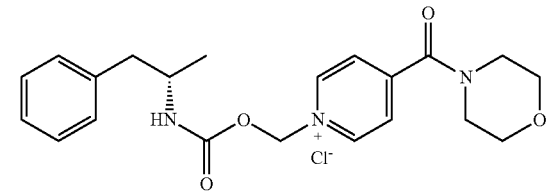

N-Isonicotinoylmorpholine (0.135 g, 0.7 mmol), ClCH$_2$OCO-AMP 2 (0.188 g, 0.826 mmol) and NaI (0.113 g, 0.756 mmol) in acetone (8 mL) were refluxed for 1 hr. The solid was filtered off. The filtrate was concentrated to dryness and then dissolved in EtOH (6 mL). The solution was treated with Dowex 1×8 twice (200-400, Cl form, 1 g and 0.5 g). The filtrate after resin treatment was concentrated and dried over vacuum to give 0.278 g of 4b as an amorphous solid. The yield was 94%.

b) Conjugate 4a was Made by the Similar Synthetic Methods as 4b and the Yield was 84%

3. Synthesis of Conjugates AMP-CO$_2$CH$_2$-isonicotinoyl-amino Acid or AMP-CO$_2$CH$_2$-isonicotinoyl-peptide 5a-y 5a-y

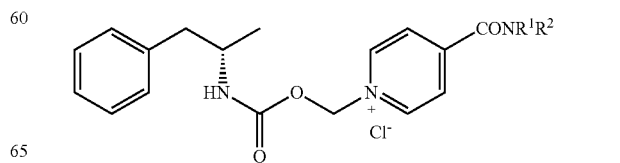

TABLE 2

Structures of conjugates 5a-5y

| Comp. | Structure |
|---|---|
| 5a | 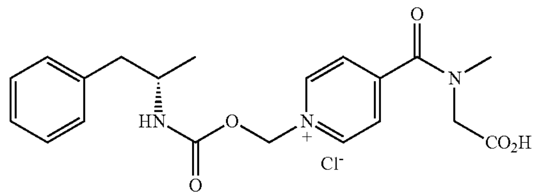 |
| 5b | 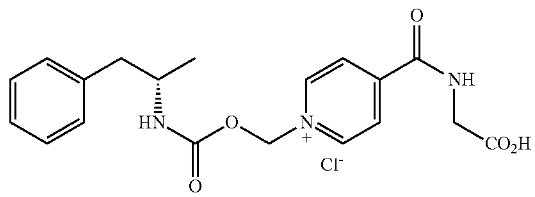 |
| 5c | 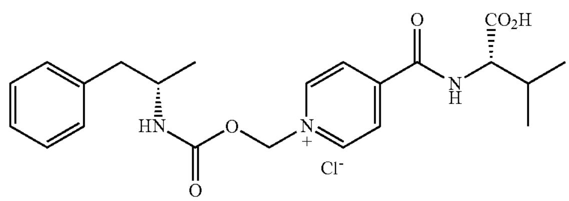 |
| 5d | 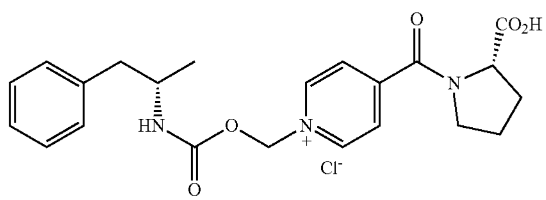 |
| 5e | 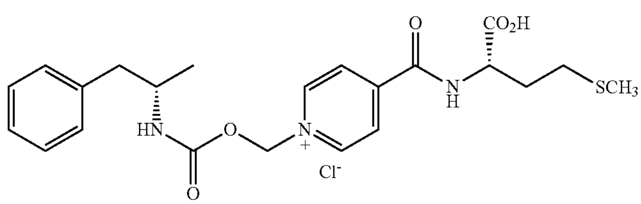 |
| 5f | 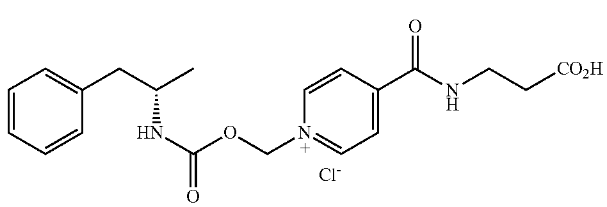 |
| 5g | 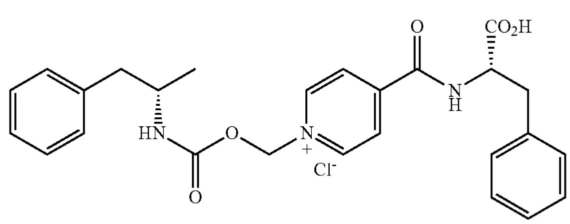 |

TABLE 2-continued
Structures of conjugates 5a-5y
| Comp. | Structure |
|---|---|
| 5h | 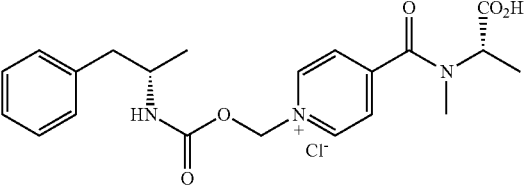 |
| 5i | 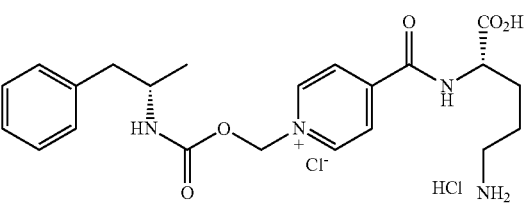 |
| 5j | 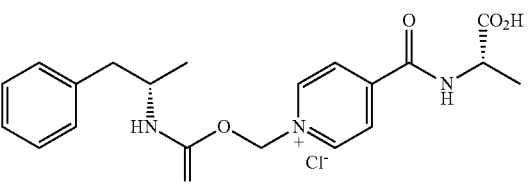 |
| 5k | 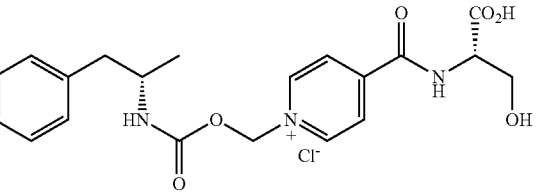 |
| 5l | 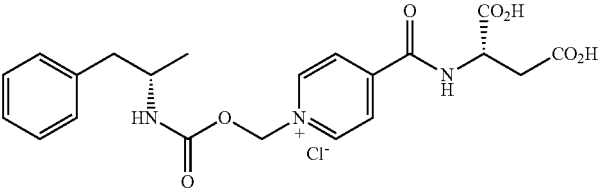 |
| 5m | 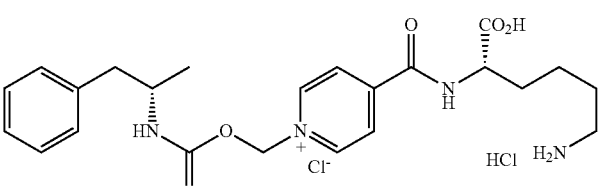 |
| 5n | 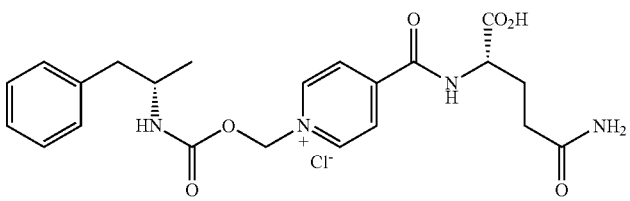 |

TABLE 2-continued

Structures of conjugates 5a-5y

| Comp. | Structure |
|---|---|
| 5o | 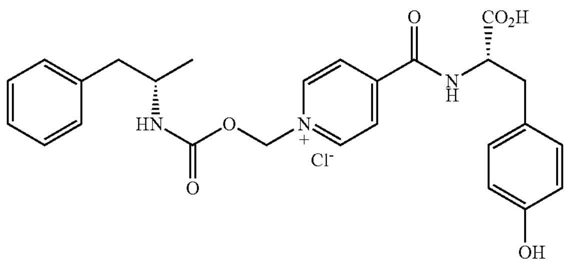 |
| 5p | 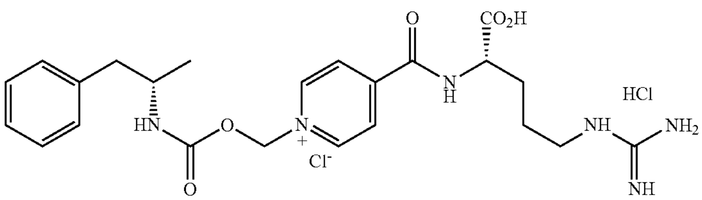 |
| 5q | 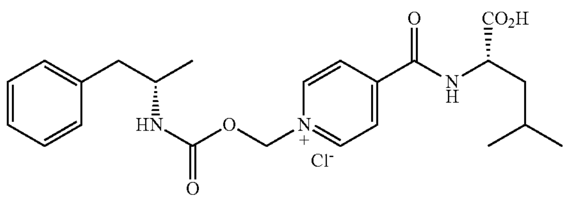 |
| 5r | 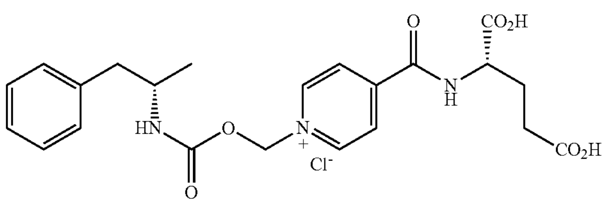 |
| 5s | 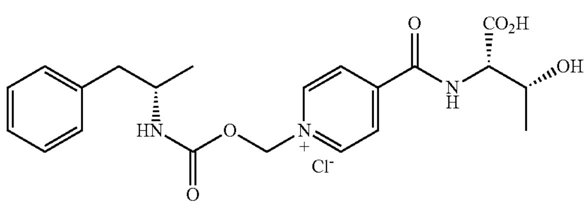 |
| 5t | 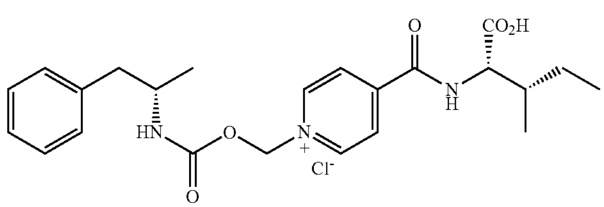 |
| 5u | 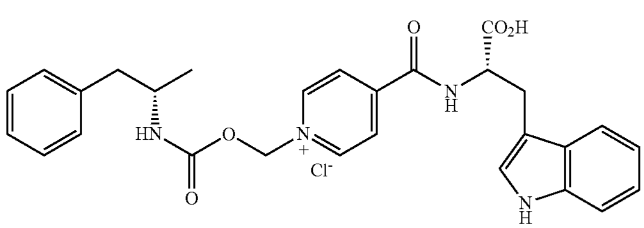 |

TABLE 2-continued

Structures of conjugates 5a-5y

| Comp. | Structure |
|---|---|
| 5v | 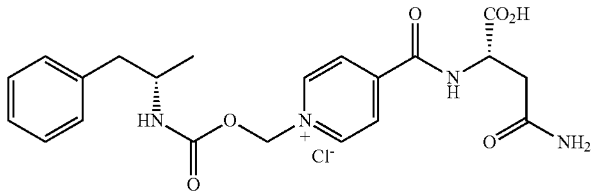 |
| 5w | 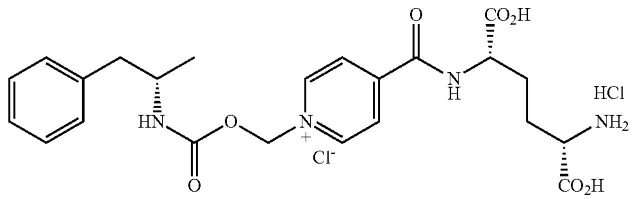 |
| 5x | 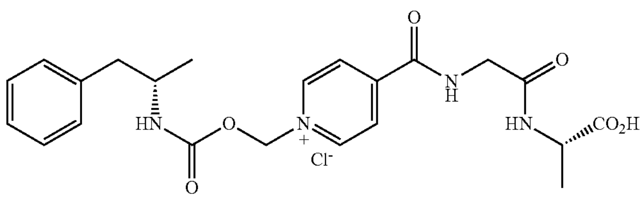 |
| 5y | | a) Synthesis of AMP-CO$_2$CH$_2$-isonicotinoyl-Thr 5s

(a) TEA/DCM;
(b) 7s, NaI, acetone;
(c) 4M HCl/dioxane, then Dowex 1 × 8, prep HPLC Step 1: Isonicotinoyl-Thr(tBu)—OtBu 7s To O-t-Butyl-threonine t-butyl ester (H-Thr(tBu)—OtBu, 0.694 g, 3 mmol) in DCM (50 mL) was added Et$_3$N (1.062 g, 10.5 mmol). Isonicotinoyl chloride hydrochloride (0.801 g, 4.5 mmol) was added in 4 portions over 15 min in a water bath (room temperature). The reaction was stirred for 2 hr. Subsequently, 5% of aq. NH$_4$Cl (20 mL) was added to quench the reaction. The DCM layer was dried over Na$_2$SO$_4$. The product was purified by silica gel column chromatography (4% MeOH/DCM). 0.894 g of 7s was obtained as syrup. The yield was 88.6%.

Step 2: AMP-CO$_2$CH$_2$-isonicotinoyl-Thr 5s

Isonicotinoyl-Thr(tBu)—OtBu 7s (0.269 g, 0.8 mmol), ClCH$_2$OCO-AMP 2 (0.219 g, 0.96 mmol) and NaI (0.138 g, 0.92 mmol) in acetone (10 mL) were refluxed for 1.5 hr. The solid was filtered off. The filtrate was concentrated and purified by silica gel column chromatography (EtOAc then 8% MeOH/DCM) to give an amorphous solid. To this solid was added 4 M HCl/dioxane (10 mL) and the mixture was stirred at room temperature for 4 hr. Solvent was evaporated to dryness and dried over vacuum for 1 hr. The resulting residue was dissolved in 8 mL of ethanol and treated with Dowex 1×8 (200-400, Cl form, 1.2 g). The filtrate, after resin treatment, was concentrated and further purified by prep HPLC to give 0.133 g of 5s as amorphous solid. The yield was 37%.

b) Synthesis of AMP-CO$_2$CH$_2$-isonicotinoyl-Ile 5t

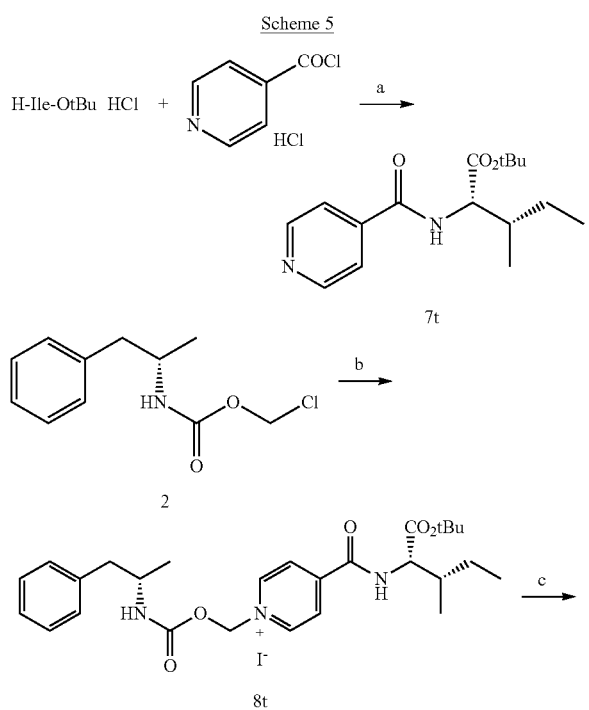

Scheme 5

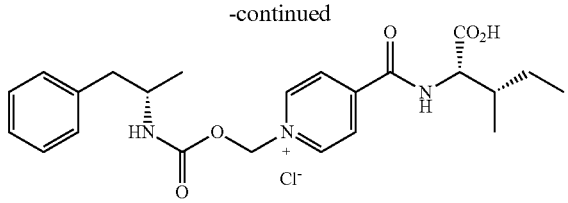

5t (a) TEA/DCM;
(b) 7t, NaI, acetone;
(c) 4M HCl/dioxane, then Dowex 1 × 8

Step 1: Isonicotinoyl-Ile-OtBu 7t

To isoleucine tert-butyl ester HCl (H-Ile-OtBu HCl, 0.671 g, 3 mmol) in DCM (50 mL) was added Et$_3$N (1.821 g, 18 mmol). Isonicotinoyl chloride hydrochloride (0.961 g, 5.4 mmol) was added in 4 portions over 15 min in a water bath (room temperature). The reaction was stirred for 2 hr. Subsequently, 5% of aq. NH$_4$Cl (20 mL) was added to quench the reaction. The DCM layer was dried over Na$_2$SO$_4$. The product was purified by silica gel column chromatography (4-5% MeOH/DCM). 0.780 g of 7t was obtained as syrup. The yield was 90%.

Step 2: AMP-CO$_2$CH$_2$-isonicotinoyl-Ile 5t

Isonicotinoyl-Ile-OtBu 7t (0.234 g, 0.8 mmol), ClCH$_2$OCO-AMP 2 (0.219 g, 0.96 mmol) and NaI (0.138 g, 0.92 mmol) in acetone (10 mL) were refluxed for 1.5 hr. The solid was filtered off. The filtrate was concentrated to give a solid. To the solid 15 mL of EtOAc/hexanes (2:1) was added. The solid was collected and washed with EtOAc/hexanes (2:1, 2 mL×2), and dried over vacuum. The solid in 4 M HCl/dioxane (8 mL) was stirred at room temperature for 4 hr. Solvent was evaporated to dryness and dried over vacuum to give an amorphous solid, which was dissolved in 6 mL of ethanol and treated with Dowex 1×8 twice (200-400, Cl form, 1 g and 0.5 g). The filtrate, after resin treatment, was concentrated and dried over vacuum to give 0.337 g of 5t as an amorphous solid. The yield was 86%.

c) Conjugates 5a-5r, 5u-5y were Synthesized by Similar Procedures as 5s and 5t

4. Synthesis of Conjugates AMP-CO$_2$CH$_2$-isonicotinoyl-amino Acid Esters 9a-9h

TABLE 3

Structures of conjugates 9a-9h

| Comp. | Structure |
|---|---|
| 9a | 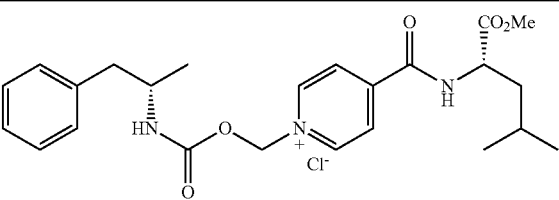 |

TABLE 3-continued
Structures of conjugates 9a-9h
| Comp. | Structure |
|---|---|
| 9b | 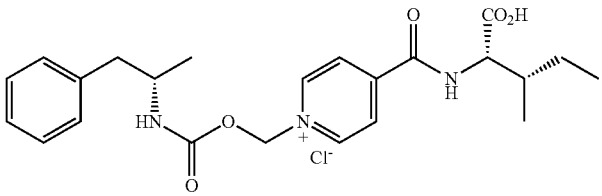 |
| 9c | 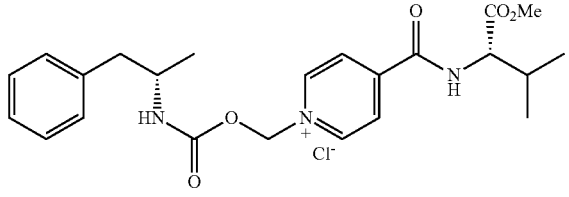 |
| 9d | 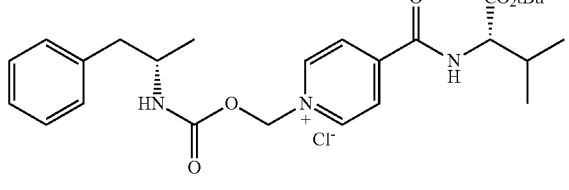 |
| 9e | 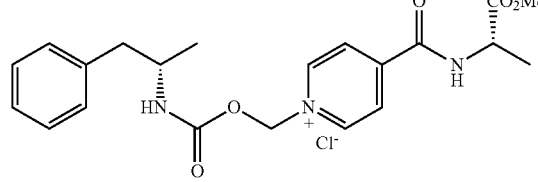 |
| 9f | 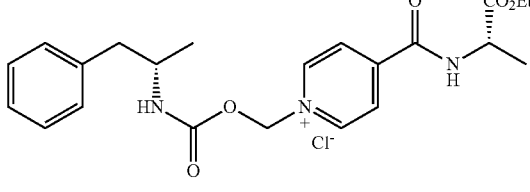 |
| 9g | 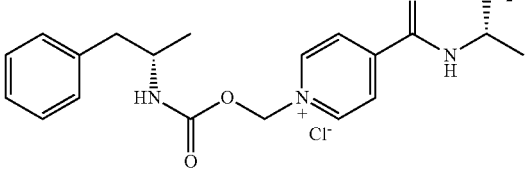 |
| 9h | 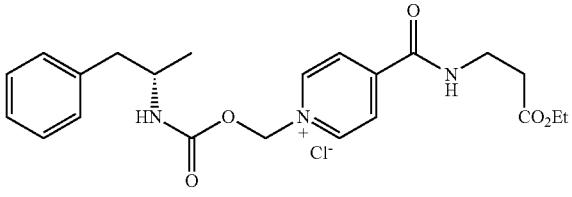 |

Scheme 6

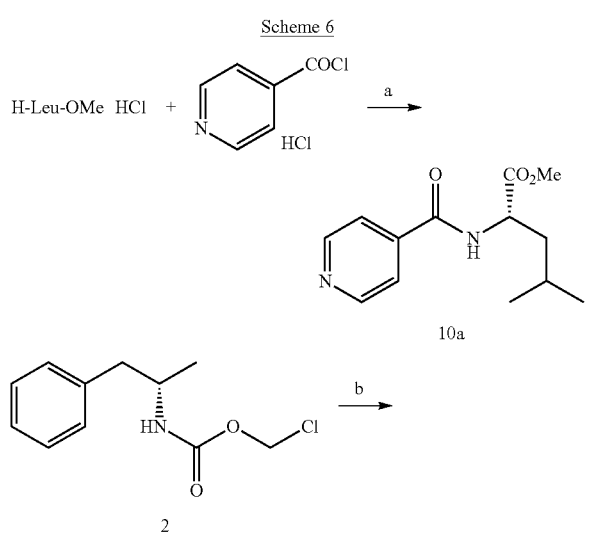

(a) TEA/DCM;
(b) 10a, NaI, acetone, then Dowex 1 × 8

Step 1: Isonicotinoyl-Leu-OMe 10a 10a was made by the similar procedure as 7t and was purified by silica gel chromatography column (7% MeOH/DCM) to give 0.212 g of syrup (1 mmol scale). The yield was 84.7%.

Step 2: AMP-CO$_2$—CH$_2$-isonicotinoyl-Leu-OMe 9a

Isonicotinoyl-Leu-OMe 10a (0.212 g, 0.85 mmol), ClCH$_2$OCO-AMP 2 (0.232 g, 1.02 mmol) and NaI (0.147 g, 0.98 mmol) in acetone (10 mL) were refluxed for 1.5 hr. The solid was filtered off. The filtrate was concentrated to dryness and then dissolved in 7 mL of methanol and treated with Dowex 1×8 twice (200-400, Cl form, 1 g and 0.5 g). The filtrate, after resin treatment, was concentrated and dried over vacuum to give 0.381 g of 9a as an amorphous solid. The yield was 94%.

b) Conjugates 9b-9h were Synthesized by Procedures Similar to 9a

5. Synthesis of Conjugates AMP-CO$_2$CH$_2$-Isonicotinoyl-Amino Acid Amides and AMP-CO$_2$CH$_2$-Nicotinoyl-Amino Acid Amide 11a and 11b

TABLE 4

Structures of conjugates 11a and 11b

| Comp. | Structure |
|---|---|
| 11a | 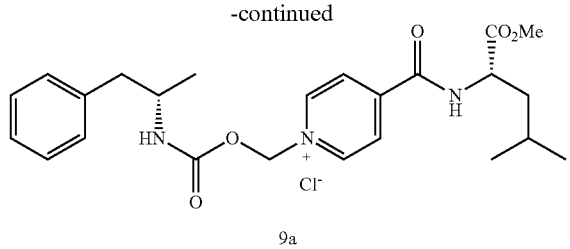 |
| 11b | | a) Synthesis of AMP-CO$_2$CH$_2$-isonicotinoyl-Val-NH$_2$ 1a

Scheme 7

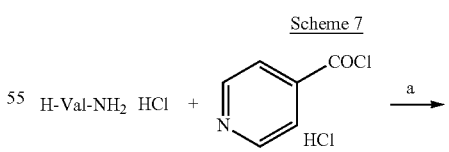

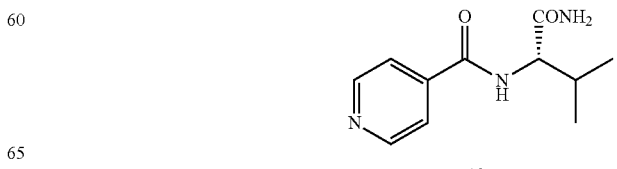

12a

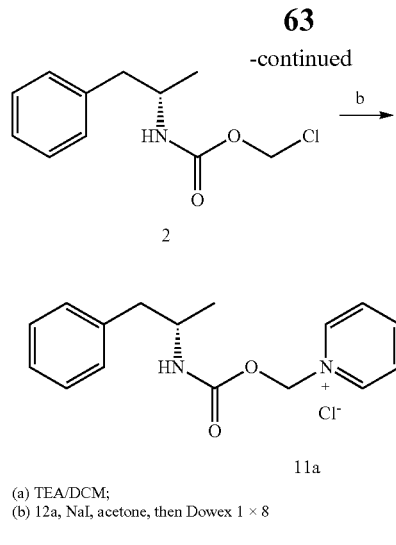

(a) TEA/DCM;
(b) 12a, NaI, acetone, then Dowex 1 × 8

Step 1: Isonicotinoyl-Val-NH₂ 12a

To valine amide HCl (H-Val-NH₂ HCl, 0.763 g, 5 mmol) in DCM (60 mL) was added Et₃N (3.036 g, 30 mmol). Isonicotinoyl chloride hydrochloride (1.602 g, 9 mmol) was added in 5 portions over 20 min in a water bath (room temperature). The reaction was stirred for 1 hr. Subsequently, 5% of aq. NH₄Cl (20 mL) was added to quench the reaction and the mixture was stirred for 10 min. DCM was evaporated to leave a solid in aqueous solution. The solid was collected by filtration and washed with water (5 mL×2) and EtOAc (3 mL), dried over vacuum. 0.514 g of 12a was obtained. The yield was 46%.

Step 2: AMP-CO₂CH₂-isonicotinoyl-Val-NH₂ 11a

Isonicotinoyl-Val-NH₂ 12a (0.155 g, 0.7 mmol), ClCH₂OCO-AMP 2 (0.191 g, 0.84 mmol) and NaI (0.121 g, 0.805 mmol) in acetone (8 mL) were refluxed for 2 hr. The solid was filtered off. The filtrate was concentrated to give a solid. To the solid 5 mL of EtOAc was added. The solid was collected and washed with EtOAc (1 mL×2) and dried over vacuum. The solid was dissolved in 6 mL of methanol and treated with Dowex 1×8 twice (200-400, Cl form, 1 g and 0.5 g). The filtrate, after resin treatment, was concentrated and dried over vacuum to give 0.247 g of 11a as an amorphous solid. The yield was 78.6%.

6. Synthesis of Amphetamine Double Conjugates 13a

13a

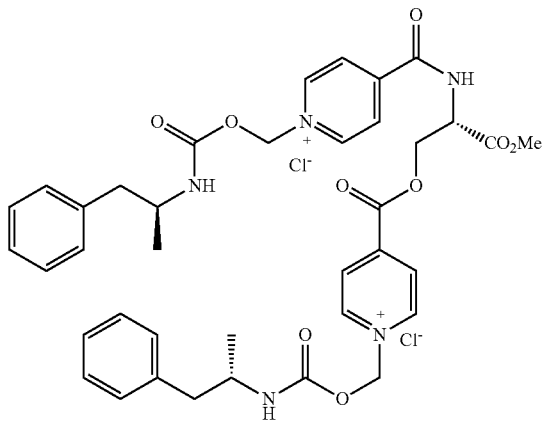

a) Synthesis of (AMP-CO₂CH₂-isonicotinoyl)₂-Ser-OMe 13a

Scheme 9

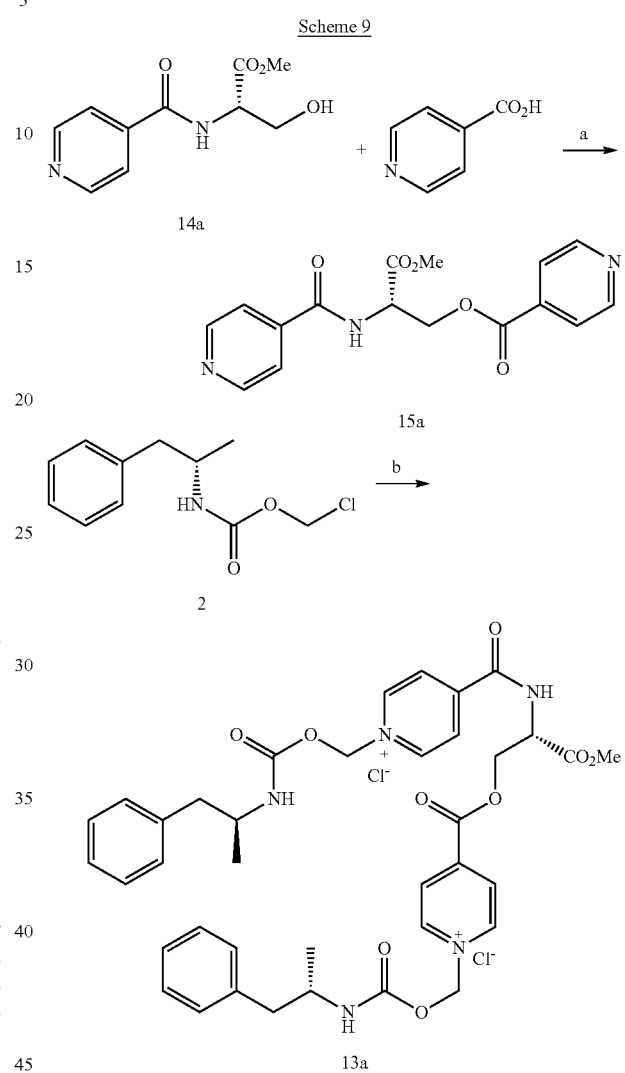

(a) EDCI/DMAP/DCM;
(b) 15a, NaI, acetone, then Dowex 1 × 8

Step 1: (Isonicotinoyl)₂-Ser-OMe 15a

To N-Isonicotinoyl-Serine methyl ester 14a (0.318 g, 1.42 mmol), isonicotinic acid (0.175 g, 1.42 mmol) and DMAP (0.035 g, 0.284 mmol) in DCM (25 mL) was added EDCI (0.327 g, 1.704 mmol) in a water bath (room temperature). The reaction was stirred for 24 hr. Subsequently, 5% of aq. NH₄Cl (10 mL) was added to quench the reaction. The DCM layer was dried over Na₂SO₄. The product was purified by silica gel column chromatography (3-7% MeOH/DCM). 0.342 g of 15a was obtained as an amorphous solid. The yield was 73%.

Step 2: (AMP-CO₂CH₂-isonicotinoyl)₂-Ser-OMe 13a (Isonicotinoyl)₂-Ser-OMe 15a (0.165 g, 0.5 mmol), ClCH₂OCO-AMP 2 (0.273 g, 1.2 mmol) and NaI (0.172 g, 1.15 mmol) in acetone (12 mL) were refluxed for 1.5 hr. The solid was filtered off. The filtrate was concentrated to give a syrup. To the syrup was added 20 mL of EtOAc. The liquid was decanted after the flask was shaken for a couple of minutes. The remaining semi-solid was dissolved in 8 mL of methanol and treated with Dowex 1×8 (200-400, Cl form, 2 g). The filtrate, after resin treatment, was concentrated and dried over vacuum to give 0.325 g of 13a as an amorphous solid. The yield was 82.8%.

Conjugates could be different salt forms other than chloride salt.

| Structure |
| --- |

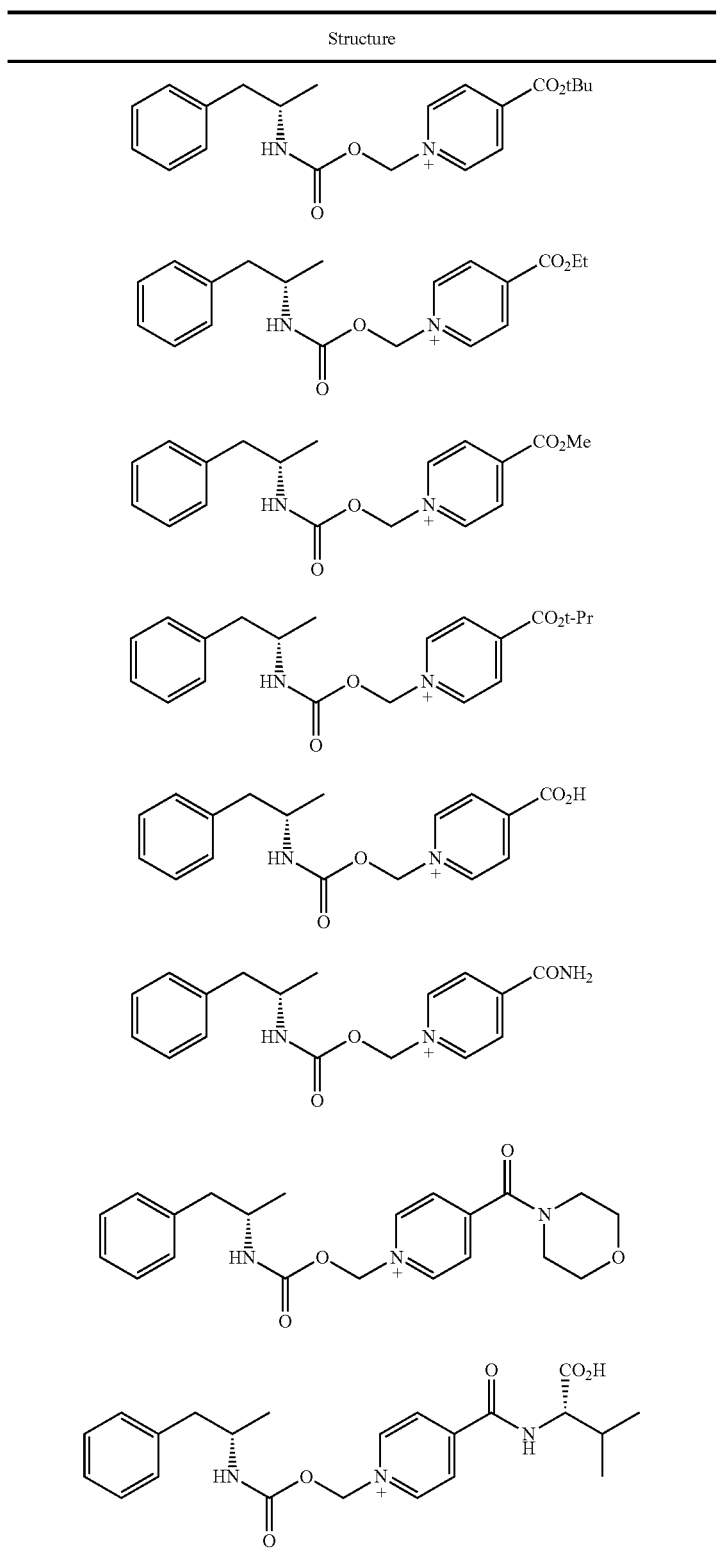

-continued
| Structure |
|---|
| 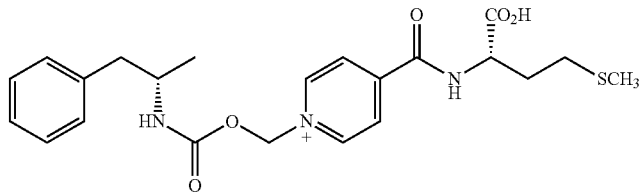 |
| 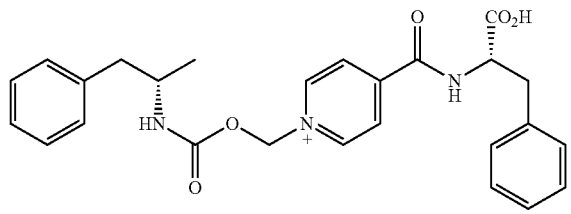 |
| 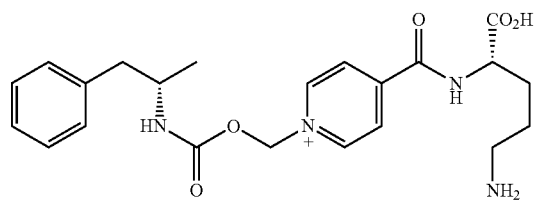 |
| 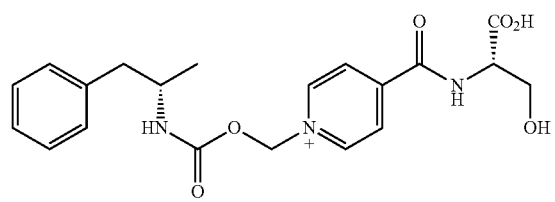 |
| 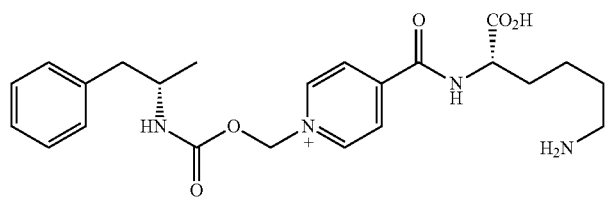 |
| 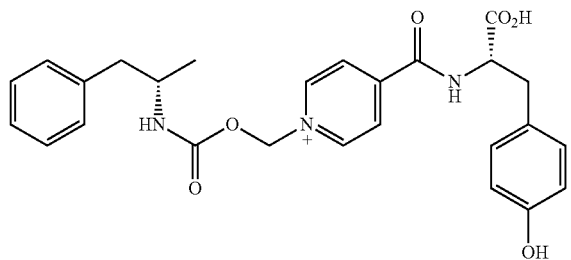 |
| 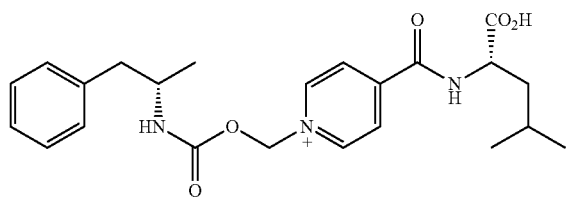 |

| Structure |
|---|
| 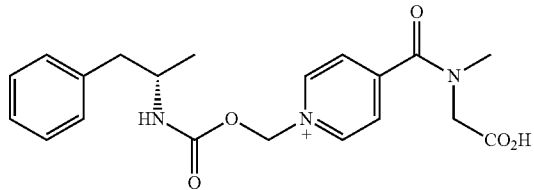 |
| 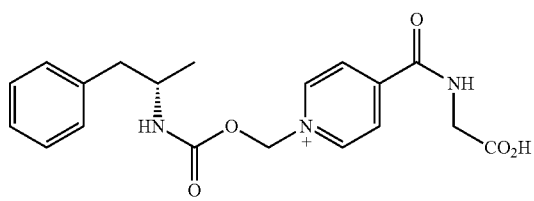 |
| 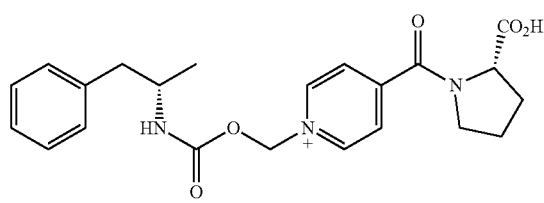 |
| 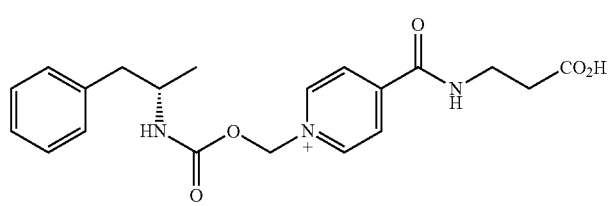 |
| 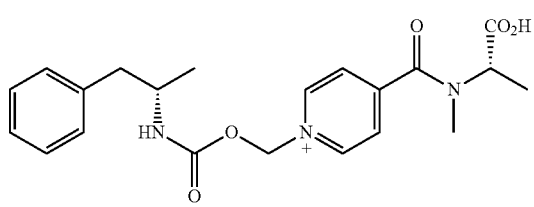 |
| 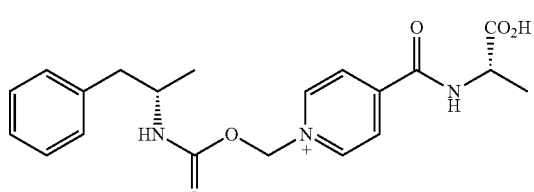 |
| 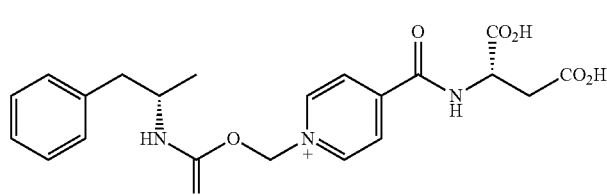 |

| Structure |
| --- |
| 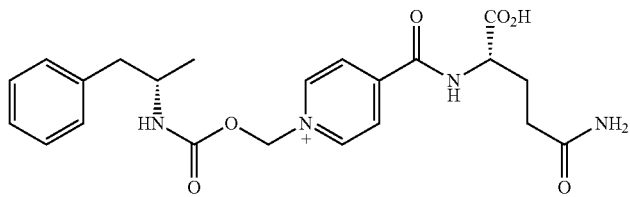 |
| 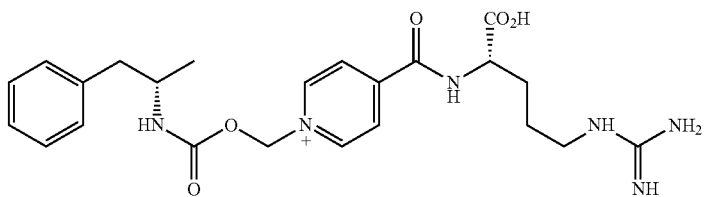 |
| 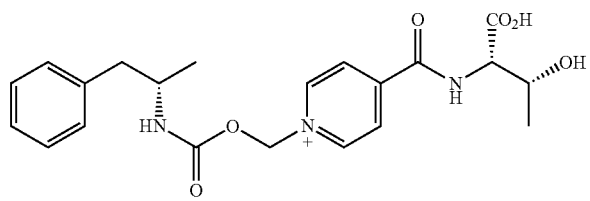 |
| 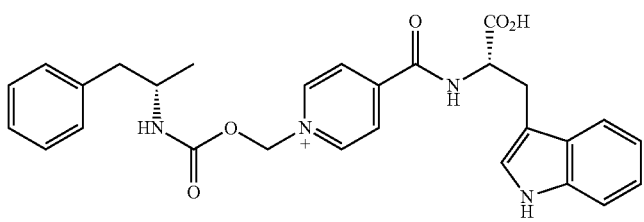 |
| 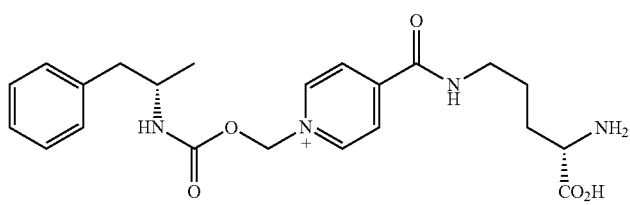 |
| 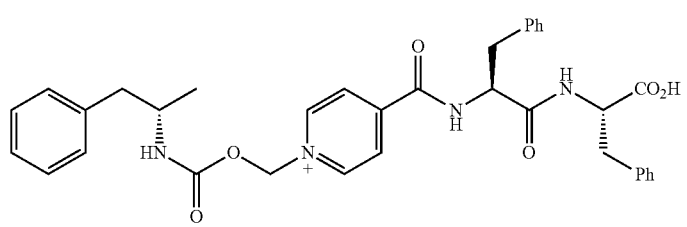 |
| 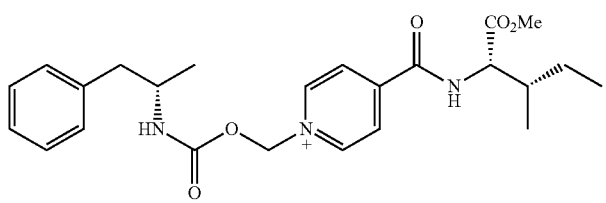 |

| Structure |
|---|
| 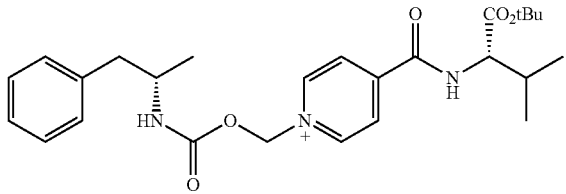 |
| 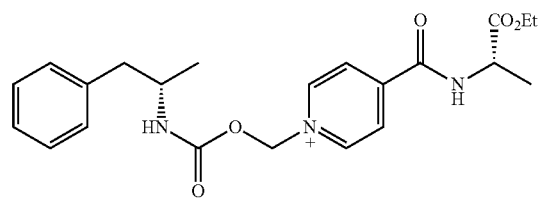 |
| 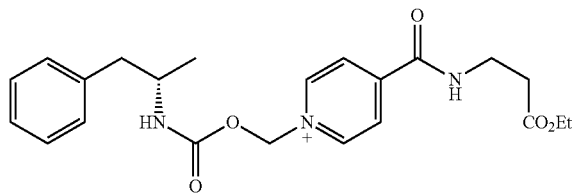 |
| 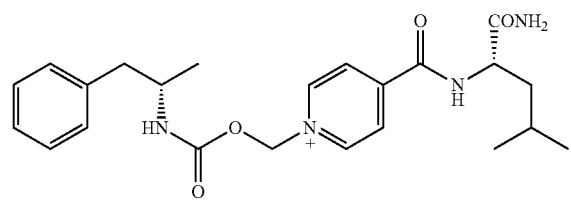 |
| 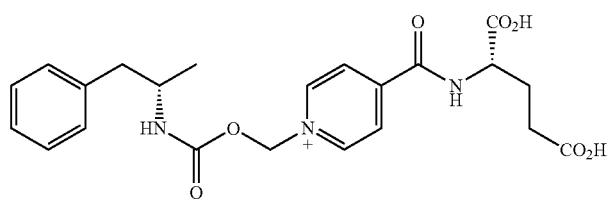 |
| 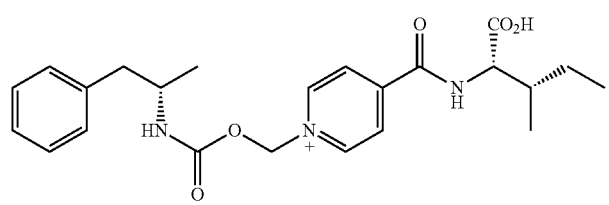 |
| 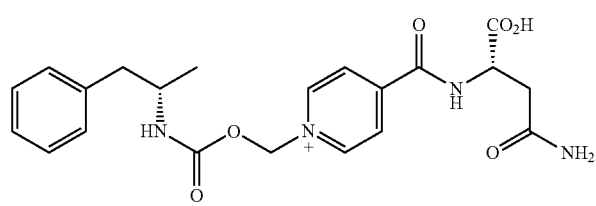 |

-continued
| Structure |
|---|
| 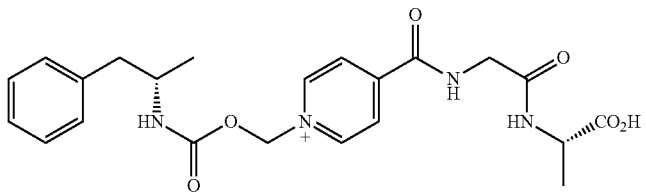 |
| 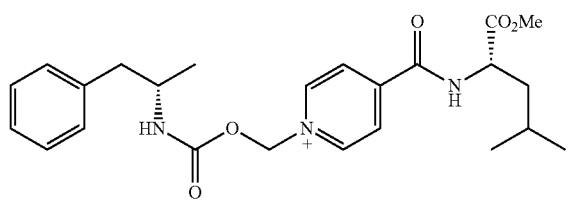 |
| 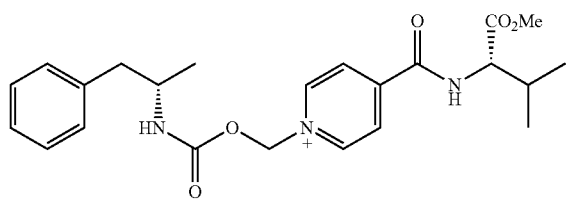 |
| 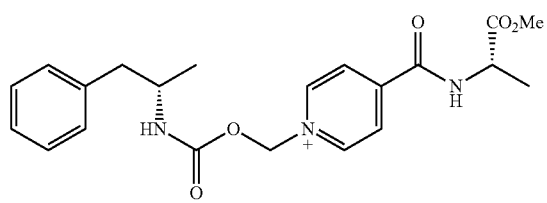 |
| 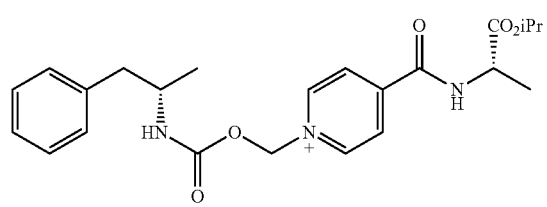 |
| 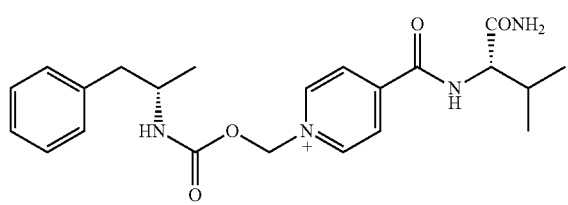 |

-continued

| Structure |
|---|
| 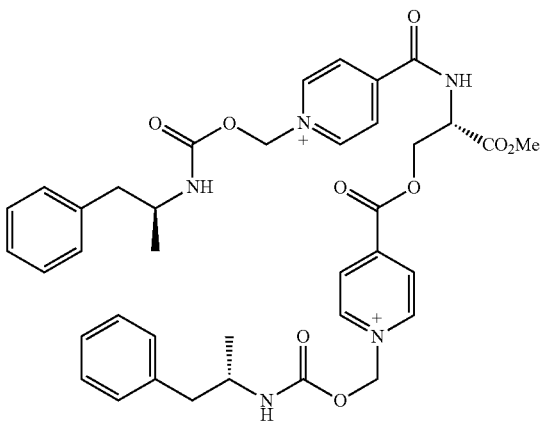 |

For the following aspects of the invention, $^1$H-NMR and $^{13}$C-NMR were recorded on a Bruker Advance II 500 spectrometer with DMSO-$d_6$ as solvent (no internal standard). Low resolution ESI mass spectra were recorded on an Agilent 1290 HPLC and Agilent 6420 QQQ Triple Mass Spectrometer, run in a positive ion mode, using 0.1% formic acid-water/0.1% formic acid-acetonitrile as mobile base. HPLC was run on an Agilent 1200 Series instrument with a YMC ODS-AQ (C-18, 4.6×250 mm, 5 μm, 120 Å) column and 0.1% TFA-water/0.1% TFA-acetonitrile as mobile phase.

| Structure | MW | Purity (%) | NMR | m.p. (° C.) |
|---|---|---|---|---|
| AMP-CO$_2$CH$_2$-isonicotinate(Et) | 378.85 | 98 | $^1$H, $^{13}$C | NA |
| AMP-CO$_2$CH$_2$-isonicotinic acid | 350.80 | 96 | $^1$H, $^{13}$C | 168-170 |
| AMP-CO$_2$CH$_2$-isonicotinoyl-Thr | 451.90 | 93 | $^1$H, $^{13}$C | NA |
| AMP-CO$_2$CH$_2$-isonicotinoyl-Ile | 463.96 | 97 | $^1$H, $^{13}$C | NA |
| AMP-CO$_2$CH$_2$-isonicotinoyl-Val-NH$_2$ | 448.95 | 97 | $^1$H, $^{13}$C | NA |

NA: compounds were amorphous and melting point could not be determined

Example 1: Oral Pharmacokinetic Study

Conjugates of d-amphetamine, and d-amphetamine sulfate or lisdexamfetamine dimesylate comparator compound were dissolved in an appropriate vehicle and administered in rats via oral gavage at doses of 5.6 μmol/kg. Whole blood samples were collected via retro-orbital bleeding at 0.25, 0.5, 1, 2, 4, and optionally at 3 and 6 hours postdose. Blood samples were centrifuged and the resulting plasma samples were collected for analysis of amphetamine concentrations by LC-MS/MS.

The oral pharmacokinetic plasma concentration-time profiles are shown in FIGS. 1-17. A summary of the oral pharmacokinetic parameters is provided in Table 5 and Table 6.

TABLE 5

Oral PK Parameters for d-Amphetamine Conjugates Administered in Rat Using a 4-hour Time Course

| Conjugate | $C_{max}$ (ng/mL) | $AUC_{0\text{-}4\,hr}$ (hr*ng/mL) | $T_{max}$ (hours) |
|---|---|---|---|
| AMP-CO$_2$CH$_2$-isonicotinate(tBu) | 22.8 | 60.1 | 2.8 |
| AMP-CO$_2$CH$_2$-isonicotinoyl-Ala | 66.5 | 167.5 | 1.9 |
| AMP-CO$_2$CH$_2$-isonicotinoyl-N-Me-Ala | 50.9 | 123.7 | 2.0 |
| AMP-CO$_2$CH$_2$-isonicotinoyl-Asp | 29.8 | 72.3 | 2.0 |
| AMP-CO$_2$CH$_2$-isonicotinoyl-Gly | 36.7 | 105.5 | 2.4 |
| AMP-CO$_2$CH$_2$-isonicotinoyl-Gly-Ala | 60.5 | 139.6 | 2.0 |
| AMP-CO$_2$CH$_2$-isonicotinoyl-morpholine | 34.1 | 92.5 | 1.5 |
| AMP-CO$_2$CH$_2$-isonicotinoyl-Orn | 56.2 | 130.9 | 1.3 |
| AMP-CO$_2$CH$_2$-isonicotinoyl-Pro | 23.0 | 62.6 | 1.8 |
| AMP-CO$_2$CH$_2$-isonicotinoyl-Sar | 43.7 | 112.9 | 1.9 |
| AMP-CO$_2$CH$_2$-isonicotinoyl-Ser | 44.2 | 110.7 | 1.8 |
| AMP-CO$_2$CH$_2$-isonicotinoyl-Thr | 32.1 | 85.3 | 2.4 |
| AMP-CO$_2$CH$_2$-isonicotinoyl-Val | 27.4 | 74.0 | 2.6 |
| AMP-CO$_2$CH$_2$-isonicotinoyl-Phe | 20.2 | 53.0 | 2.6 |
| AMP-CO$_2$CH$_2$-isonicotinoyl-Val-OMe | 35.4 | 100.6 | 2.2 |

TABLE 6

Oral PK Parameters for d-Amphetamine Conjugates Administered in Rat Using a 6-hour Time Course

| Conjugate | $C_{max}$ (ng/mL) | $AUC_{0\text{-}4\,hr}$ (hr*ng/mL) | $AUC_{0\text{-}6\,hr}$ (hr*ng/mL) | $T_{max}$ (hours) |
|---|---|---|---|---|
| AMP-CO$_2$CH$_2$-isonicotinoyl-Ala-OEt | 28.5 | 72.8 | 105.7 | 2.0 |
| AMP-CO$_2$CH$_2$-isonicotinoyl-Ala-OiPr | 24.3 | 69.4 | 101.2 | 1.8 |
| AMP-CO$_2$CH$_2$-isonicotinoyl-β-Ala-OEt | 39.8 | 103.2 | 148.7 | 2.1 |
| AMP-CO$_2$CH$_2$-isonicotinoyl-Glu | 27.4 | 71.9 | 103.1 | 2.6 |
| AMP-CO$_2$CH$_2$-isonicotinoyl-Ile | 31.5 | 85.9 | 125.8 | 2.3 |
| AMP-CO$_2$CH$_2$-isonicotinoyl-ILe-OMe | 37.1 | 104.9 | 143.7 | 1.4 |
| AMP-CO$_2$CH$_2$-isonicotinoyl-Leu | 26.3 | 68.2 | 95.8 | 1.6 |
| AMP-CO$_2$CH$_2$-isonicotinoyl-Leu-NH$_2$ | 27.8 | 86.9 | 123.7 | 2.0 |
| AMP-CO$_2$CH$_2$-isonicotinoyl-Leu-OMe | 23.1 | 63.8 | 101.9 | 3.2 |
| AMP-CO$_2$CH$_2$-isonicotinoyl-Val-NH$_2$ | 28.7 | 82.3 | 117.0 | 2.0 |
| AMP-CO$_2$CH$_2$-isonicotinate | 17.5 | 47.1 | 72.7 | 3.20 |
| AMP-CO$_2$CH$_2$-isonicotinate(Et) | 26.0 | 75.4 | 106.6 | 1.50 |

TABLE 7

Oral PK Parameters for d-Amphetamine Conjugates Administered in Rat Using an 8-hour Time Course

| Conjugate | $C_{max}$ (ng/mL) | $AUC_{0\text{-}4\,hr}$ (hr*ng/mL) | $AUC_{0\text{-}6\,hr}$ (hr*ng/mL) | $AUC_{0\text{-}8\,hr}$ (hr*ng/mL) | $T_{max}$ (hours) |
|---|---|---|---|---|---|
| AMP-CO$_2$CH$_2$-isonicotinate | 28.2 | 65.9 | 99.1 | 82.3 | 2.38 |

Example 2: Intravenous Pharmacokinetic Study

Conjugates of d-amphetamine, and d-amphetamine sulfate or lisdexamfetamine dimesylate comparator compound were dissolved in an appropriate vehicle and administered in rats at doses of 5.6 μmol/kg by injecting the solution into the tail vein. Whole blood samples were collected via retro-orbital bleeding at 5 minutes and at 0.25, 0.5, 1 and 2 hours postdose. Blood samples were centrifuged and the resulting plasma samples were collected for analysis of levorphanol concentrations by LC-MS/MS.

The intravenous pharmacokinetic d-amphetamine plasma concentration-time profiles are shown in FIGS. 18-26. A summary of the intravenous pharmacokinetic parameters of d-amphetamine is provided in Table 8.

TABLE 8

Intravenous PK Parameters for d-Amphetamine Conjugates Administered in Rat

| Conjugate | $C_{max}$ (ng/mL) | $AUC_{0\text{-}2\,hr}$ (hr*ng/mL) | $T_{max}$ (hours) |
|---|---|---|---|
| AMP-CO$_2$CH$_2$-isonicotinate(tBu) | 7.8 | 11.3 | 0.72 |
| AMP-CO$_2$CH$_2$-isonicotinoyl-Ala-OEt | 24.7 | 32.4 | 0.52 |
| AMP-CO$_2$CH$_2$-isonicotinoyl-Gly | 25.1 | 27.3 | 0.08 |
| AMP-CO$_2$CH$_2$-isonicotinoyl-Ile | 17.7 | 23.6 | 1.20 |
| AMP-CO$_2$CH$_2$-isonicotinoyl-Leu | 32.0 | 48.8 | 1.60 |
| AMP-CO$_2$CH$_2$-isonicotinoyl-morpholine | 55.7 | 71.4 | 0.33 |
| AMP-CO$_2$CH$_2$-isonicotinoyl-Phe | 17.2 | 26.5 | 1.00 |
| AMP-CO$_2$CH$_2$-isonicotinoyl-Pro | 29.6 | 48.0 | 0.20 |
| AMP-CO$_2$CH$_2$-isonicotinoyl-Sar | 27.1 | 30.6 | 0.18 |
| AMP-CO$_2$CH$_2$-isonicotinoyl-Thr | 6.1 | 8.1 | 0.20 |
| AMP-CO$_2$CH$_2$-isonicotinoyl-Val | 20.0 | 35.8 | 0.90 |
| AMP-CO$_2$CH$_2$-isonicotinoyl-Val-NH$_2$ | 8.1 | 12.4 | 1.00 |
| AMP-CO$_2$CH$_2$-isonicotinoyl-Val-OMe | 53.7 | 69.0 | 1.00 |
| AMP-CO$_2$CH$_2$-isonicotinate(Et) | 18.8 | 26.5 | 0.72 |
| AMP-CO$_2$CH$_2$-isonicotinate | 4.1 | 6.1 | 1.00 |

Example 3: Intranasal Pharmacokinetic Study

Conjugates of d-amphetamine, and d-amphetamine sulfate or lisdexamfetamine dimesylate comparator compound were dissolved in an appropriate vehicle and administered in rats at doses of 5.6 μmol/kg by slowly adding the respective dosing solution drop-wise and alternating into the nasal openings. Whole blood samples were collected via retro-orbital bleeding at 5 minutes and at 0.25, 0.5, and 1 hours postdose. Blood samples were centrifuged and the resulting plasma samples were collected for analysis of amphetamine concentrations by LC-MS/MS.

The intranasal pharmacokinetic plasma concentration-time profiles are shown in FIGS. 27-35. A summary of the intranasal pharmacokinetic parameters is provided in Table 9.

TABLE 9

Intranasal PK Parameters for d-Amphetamine Conjugates Administered in Rat Using a 1-hour Time Course

| Conjugate | $C_{max}$ (ng/mL) | $AUC_{0-1\ hr}$ (hr*ng/mL) | $T_{max}$ (hours) |
|---|---|---|---|
| AMP-CO$_2$CH$_2$-isonicotinate(tBu) | 51.8 | 19.9 | 0.08 |
| AMP-CO$_2$CH$_2$-isonicotinoyl-Gly | 69.0 | 20.5 | 0.08 |
| AMP-CO$_2$CH$_2$-isonicotinoyl-Ile | 17.3 | 10.6 | 1.00 |
| AMP-CO$_2$CH$_2$-isonicotinoyl-Leu | 99.5 | 31.5 | 0.08 |
| AMP-CO$_2$CH$_2$-isonicohnoyl-morpholine | 290.7 | 73.0 | 0.08 |
| AMP-CO$_2$CH$_2$-isonicotinoyl-Phe | 101.1 | 46.2 | 0.08 |
| AMP-CO$_2$CH$_2$-isonicotinoyl-Pro | 95.6 | 30.5 | 0.08 |
| AMP-CO$_2$CH$_2$-isonicotinoyl-Sar | 72.8 | 22.9 | 0.08 |
| AMP-CO$_2$CH$_2$-isonicotinoyl-Thr | 13.1 | 7.3 | 0.35 |
| AMP-CO$_2$CH$_2$-isonicotinoyl-Val | 33.6 | 18.9 | 0.39 |
| AMP-CO$_2$CH$_2$-isonicotinoyl-Val-NH$_2$ | 9.1 | 13.3 | 1.30 |
| AMP-CO$_2$CH$_2$-isonicotinoyl-Val-OMe | 66.4 | 32.2 | 0.08 |

TABLE 10

Intranasal PK Parameters for d-Amphetamine Conjugates Administered in Rat Using a 4-hour Time Course

| Conjugate | $C_{max}$ (ng/mL) | $AUC_{0-1\ hr}$ (hr*ng/mL) | $AUC_{0-4\ hr}$ (hr*ng/mL) | $T_{max}$ (hours) |
|---|---|---|---|---|
| AMP-CO$_2$CH$_2$-isonicotinate (Et) | 11.1 | 8.6 | 32.6 | 0.63 |
| AMP-CO$_2$CH$_2$-isonicotinate | 7.3 | 5.0 | 21.5 | 2.18 |

Figure 30:
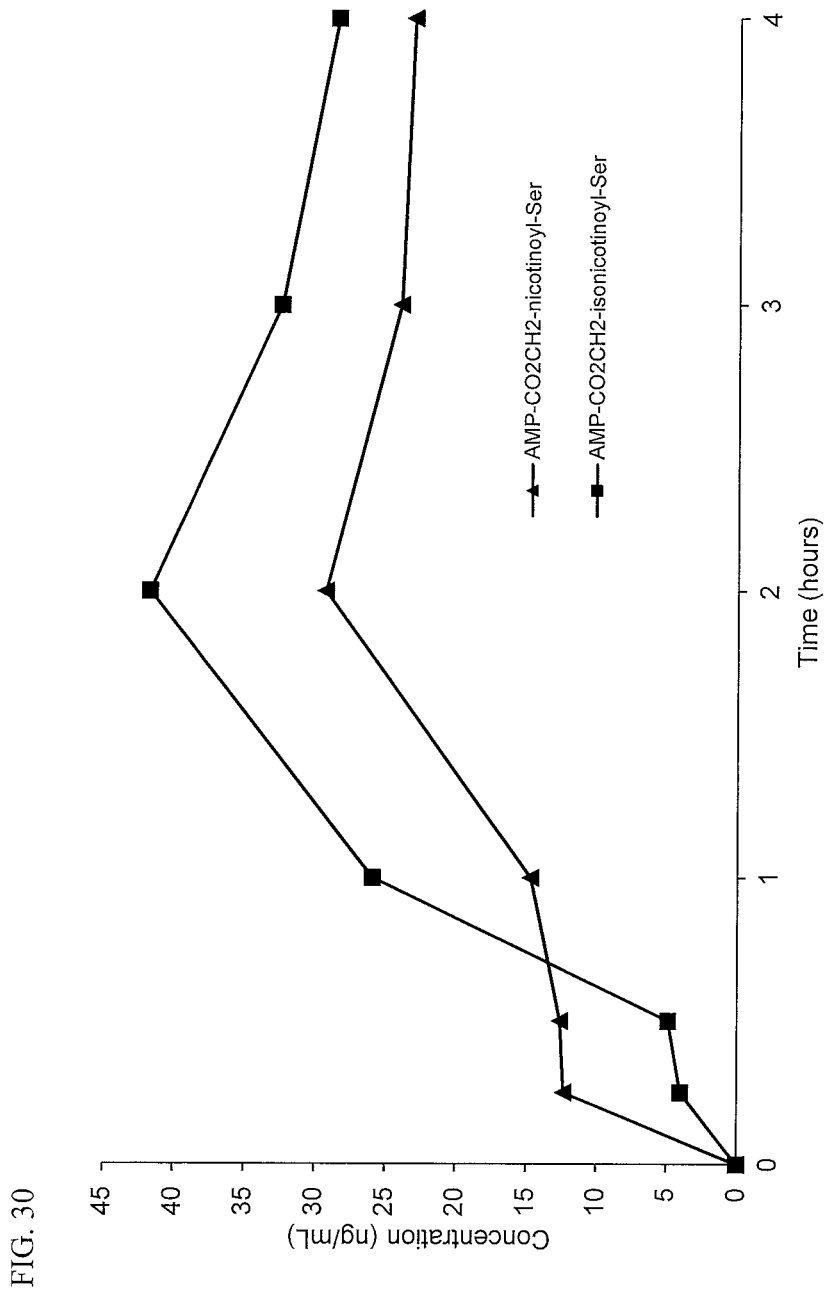
FIG. 30. Oral PK curves comparing d-amphetamine-CO₂CH₂-nicotinoyl-serine (AMP-CO₂CH₂-nicotinoyl-Ser) and d-amphetamine-CO₂CH₂-isonicotinoyl-serine (AMP-CO₂CH₂-isonicotinoyl-serine).
Figure 31:
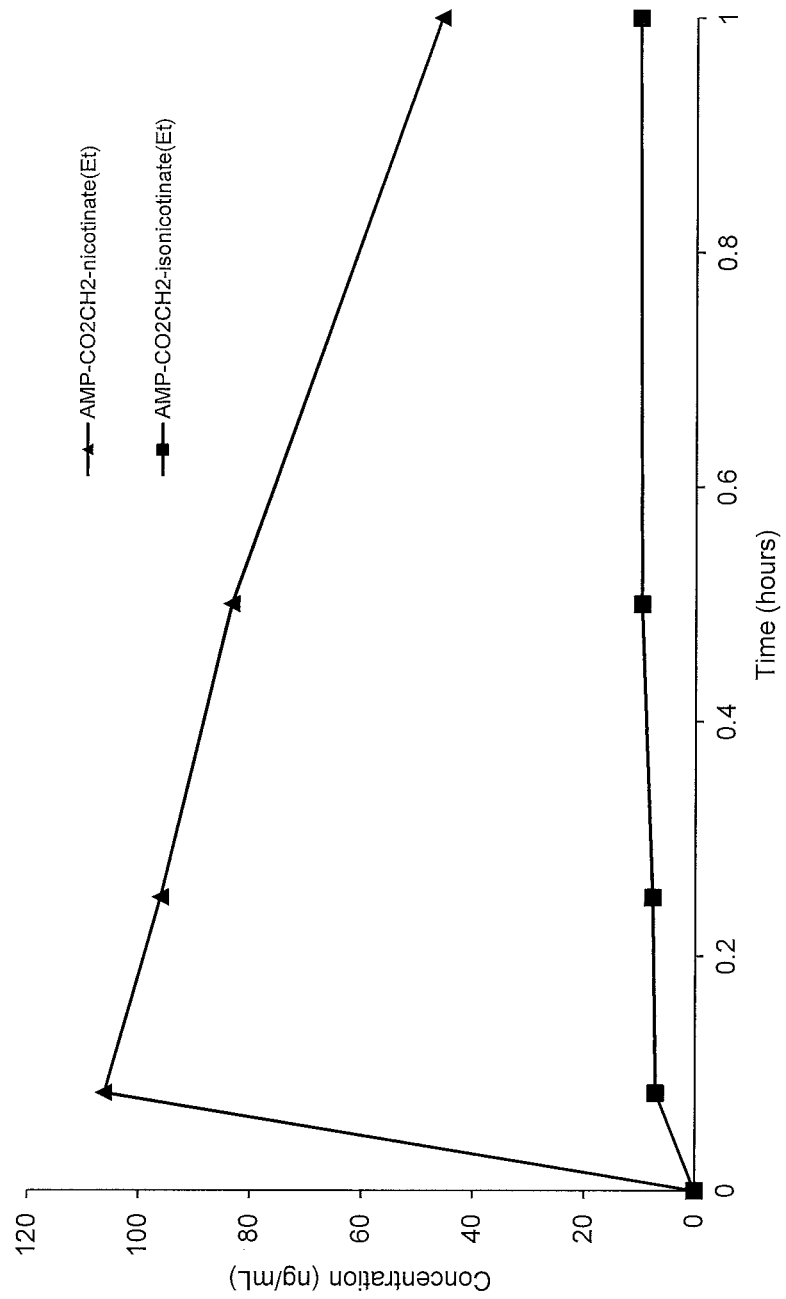
FIG. 31 Intranasal PK curves comparing d-amphetamine-CO₂CH₂-nicotinate ethyl ester (AMP-CO₂CH₂-nicotinate (Et)) and d-amphetamine-CO₂CH₂-isonicotinate ethyl ester (AMP-CO₂CH₂-isonicotinate(Et)).
Figure 32:
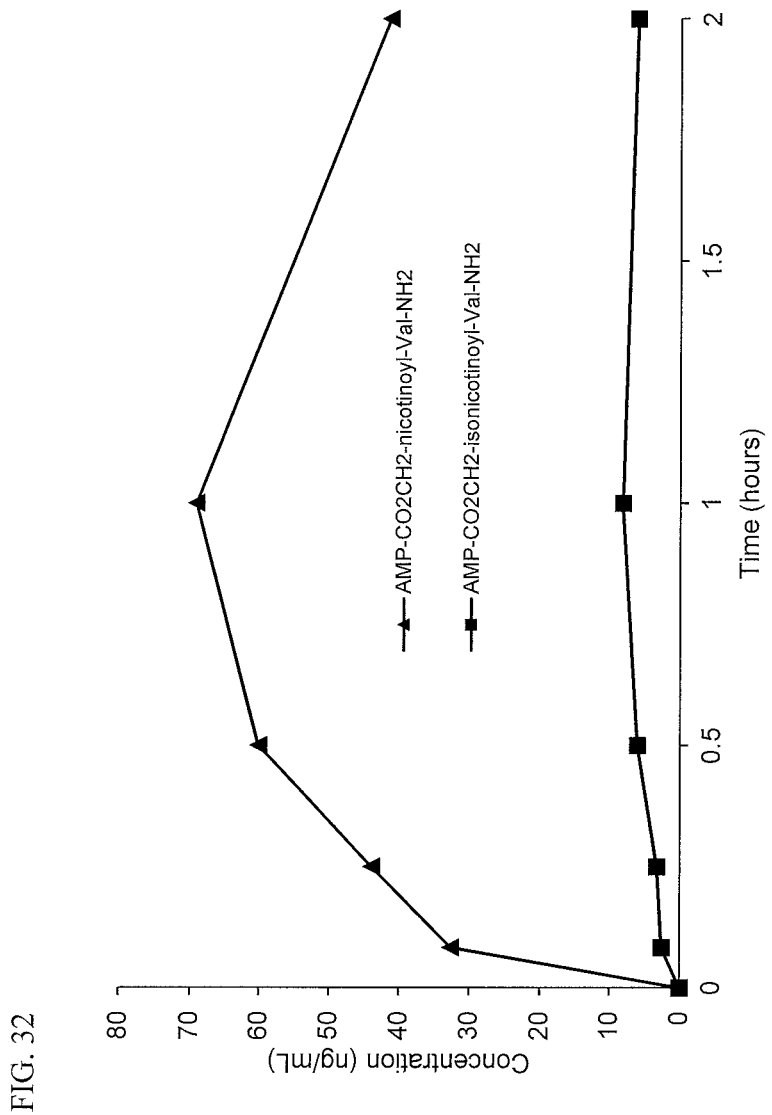
FIG. 32 Intravenous PK curves comparing d-amphetamine-CO₂CH₂-nicotinoyl-valinamide (AMP-CO₂CH₂-nicotinoyl-Val-NH₂) and d-amphetamine-CO₂CH₂-isonicotinoyl-valinamide (AMP-CO₂CH₂-isonicotinoyl-Val-NH₂).
Figure 33:
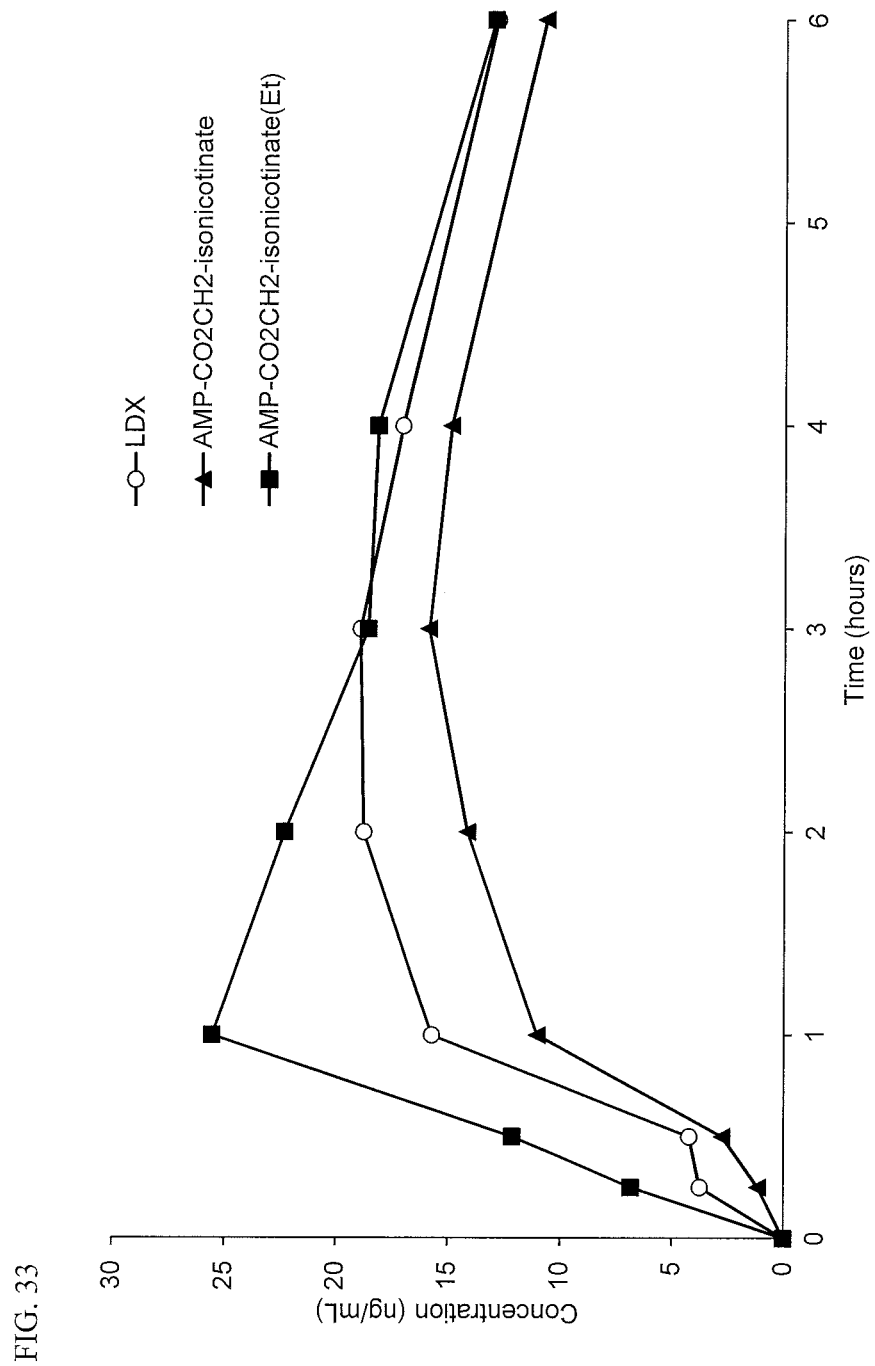
FIG. 33 Oral PK curves comparing PK curves comparing lisdexamfetamine (LDX), d-amphetamine-CO₂CH₂-isonicotinate (AMP-CO₂CH₂-isonicotinate), and d-amphetamine-CO₂CH₂-isonicotinate ethyl ester (AMP-CO₂CH₂-isonicotinate(Et)).
Figure 34:
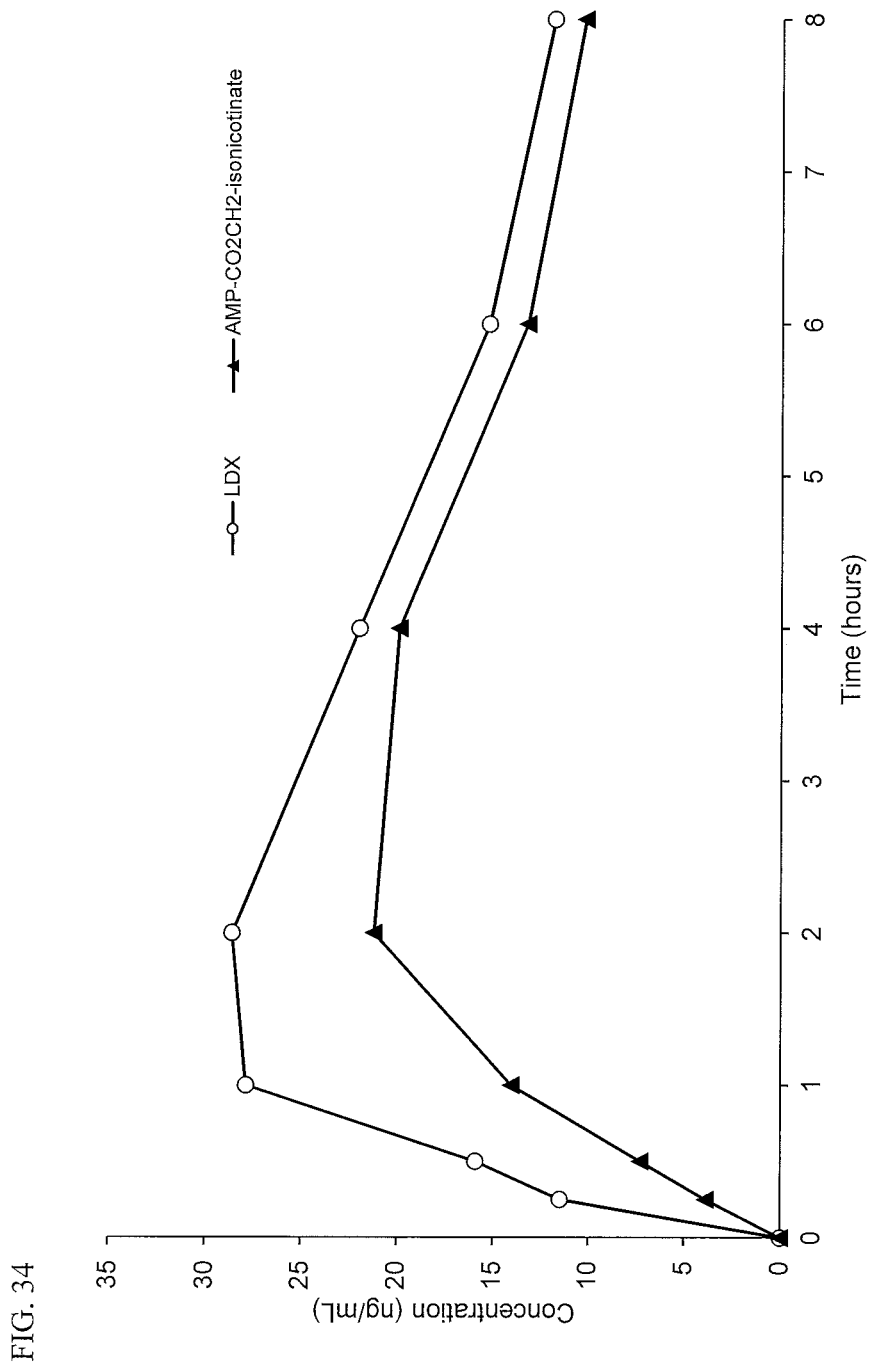
FIG. 34 Oral PK curves comparing PK curves comparing lisdexamfetamine (LDX) and d-amphetamine-CO₂CH₂-isonicotinate (AMP-CO₂CH₂-isonicotinate).
Figure 35:
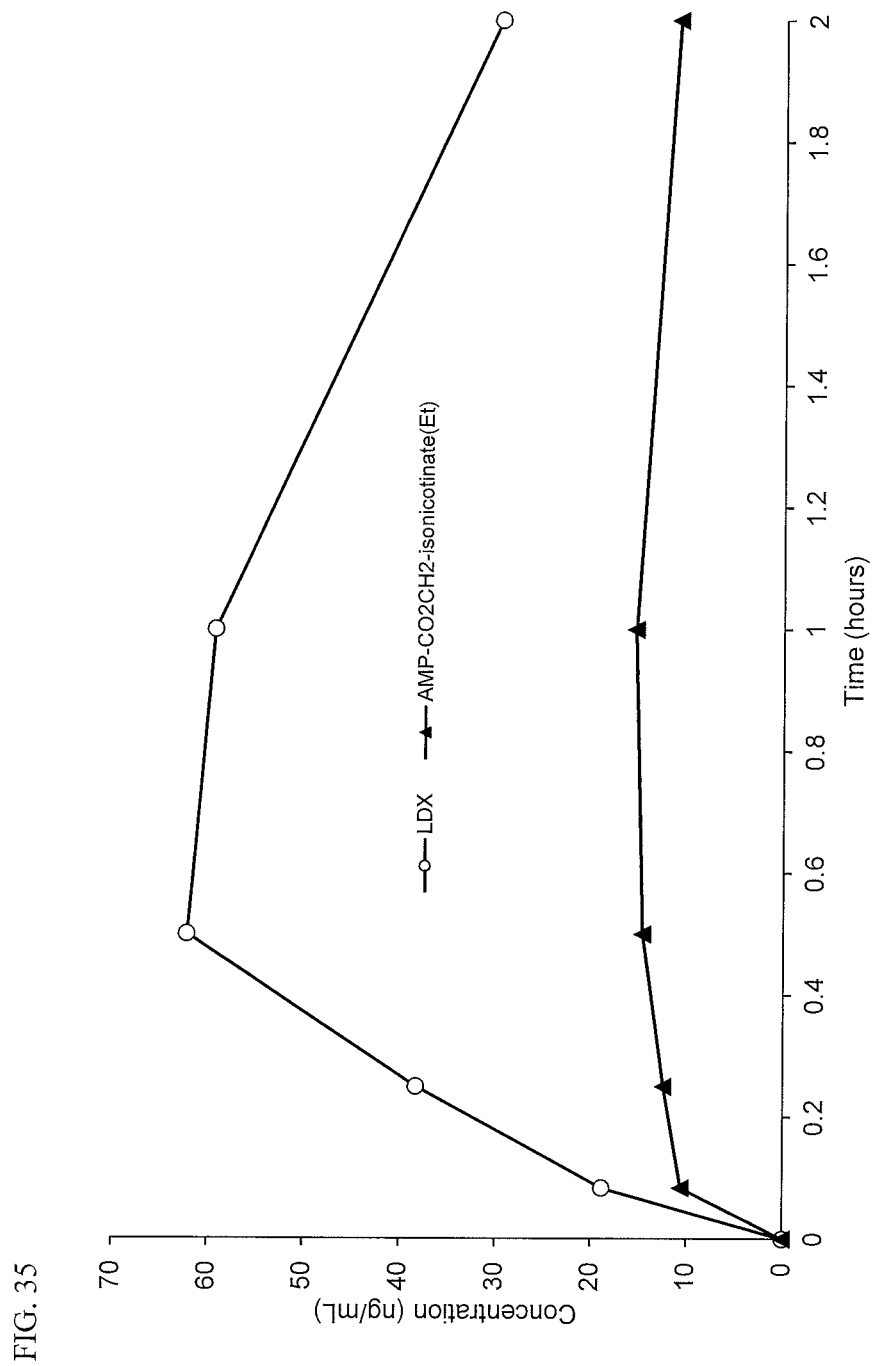
FIG. 35 Intravenous PK curves comparing lisdexamfetamine (LDX) and d-amphetamine-CO₂CH₂-isonicotinate ethyl ester (AMP-CO₂CH₂-isonicotinate(Et)).
Figure 36:
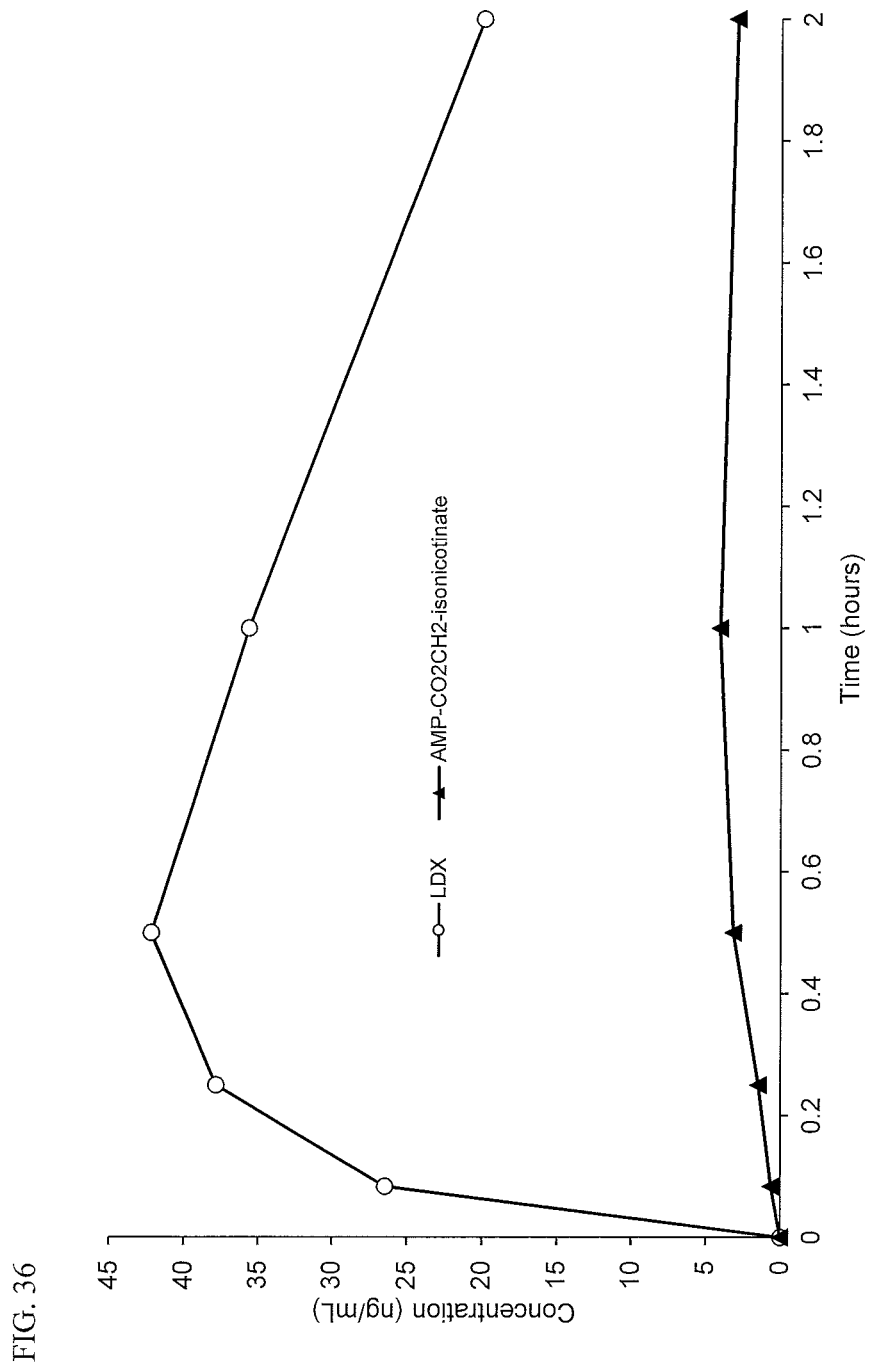
FIG. 36 Intravenous PK curves comparing lisdexamfetamine (LDX) and d-amphetamine-CO₂CH₂-isonicotinate (AMP-CO₂CH₂-isonicotinate).
Figure 37:
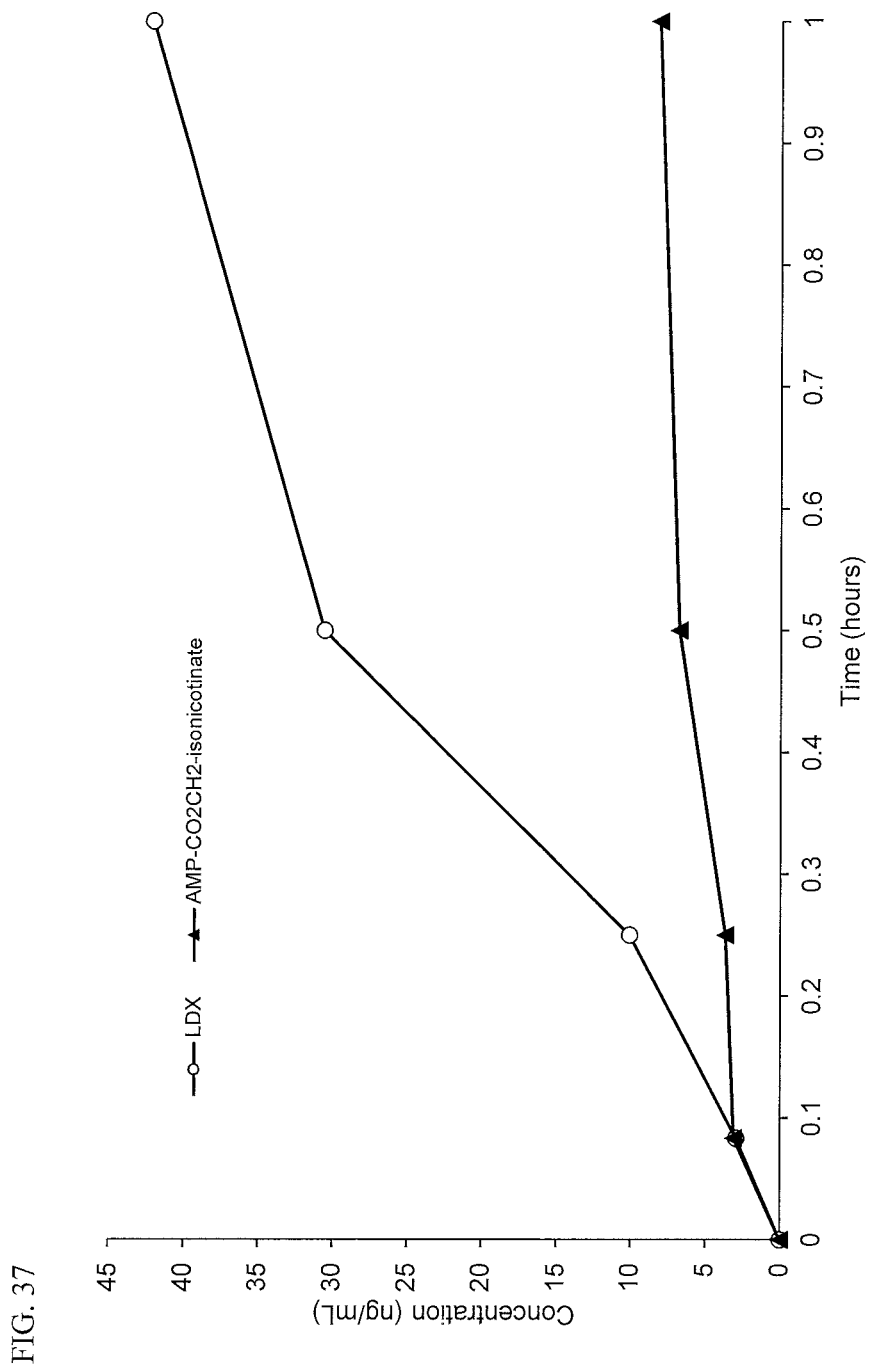
FIG. 37 Intranasal PK curves comparing lisdexamfetamine (LDX) and d-amphetamine-CO₂CH₂-isonicotinate (AMP-CO₂CH₂-isonicotinate).
Figure 38:
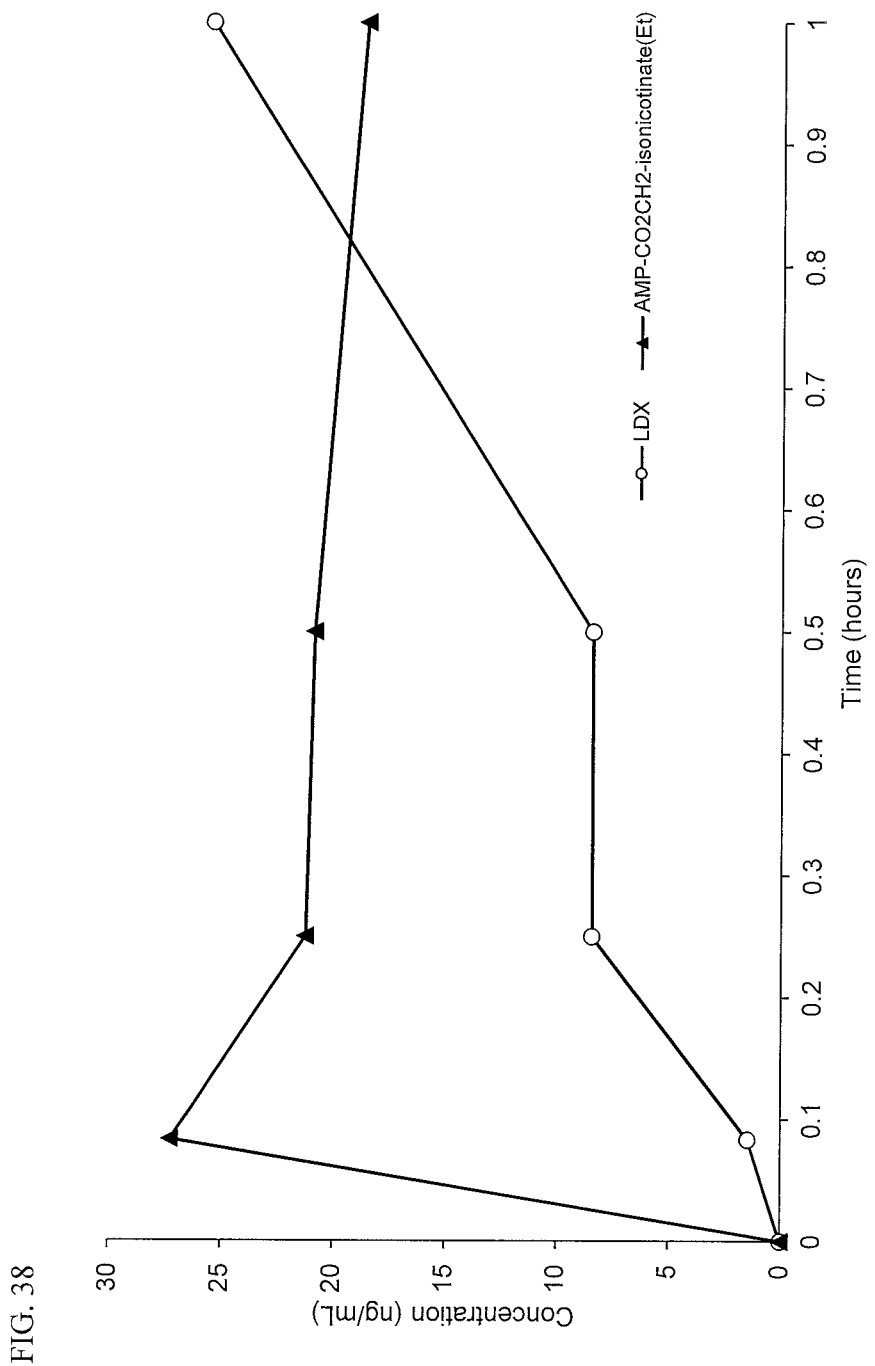
FIG. 38 Intranasal PK curves comparing and d-amphetamine-CO₂CH₂-isonicotinate ethyl ester (AMP-CO₂CH₂-isonicotinate(Et)).
Figure 39:
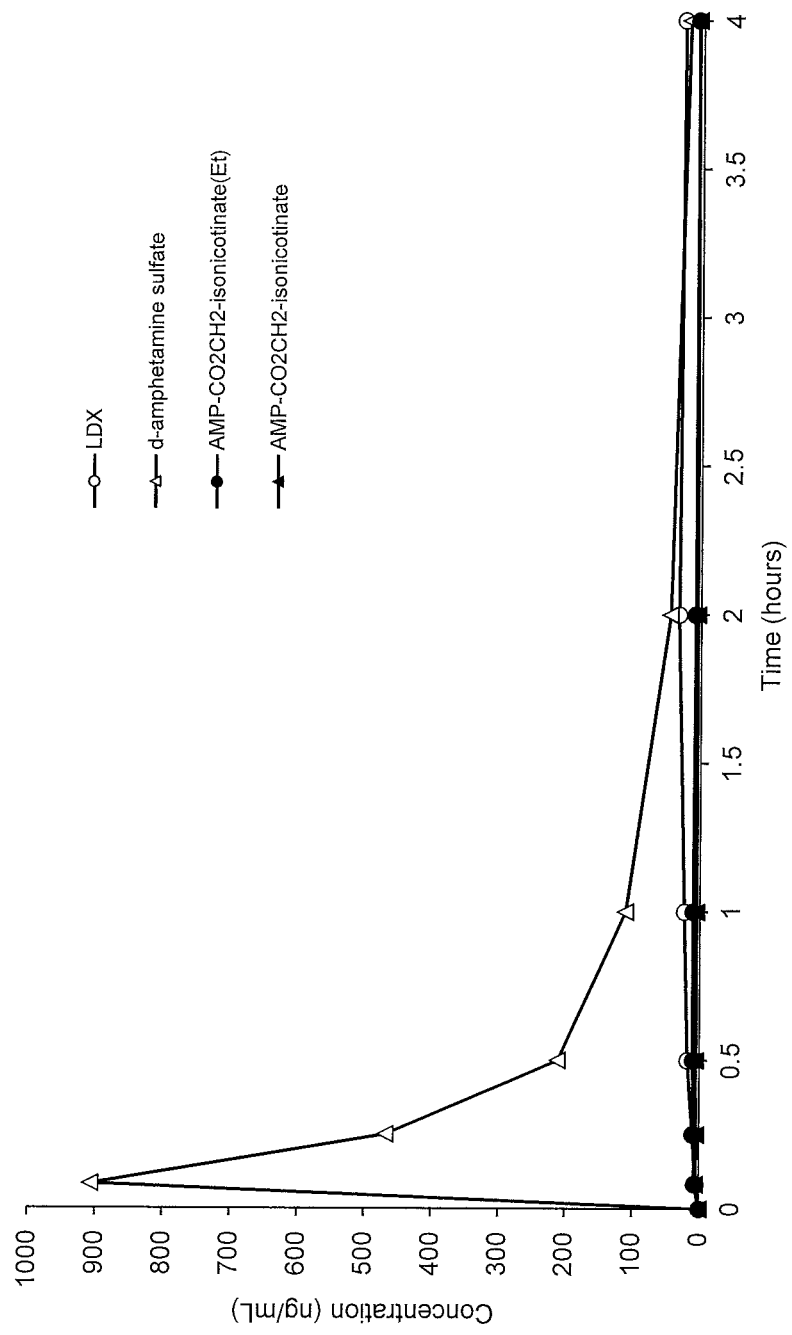
FIG. 39 Intranasal PK curves comparing lisdexamfetamine (LDX), d-amphetamine sulfate, d-amphetamine-CO₂CH₂-isonicotinate ethyl ester (AMP-CO₂CH₂-isonicotinate(Et)), and d-amphetamine-CO₂CH₂-isonicotinate (AMP-CO₂CH₂-isonicotinate).
Figure 40:
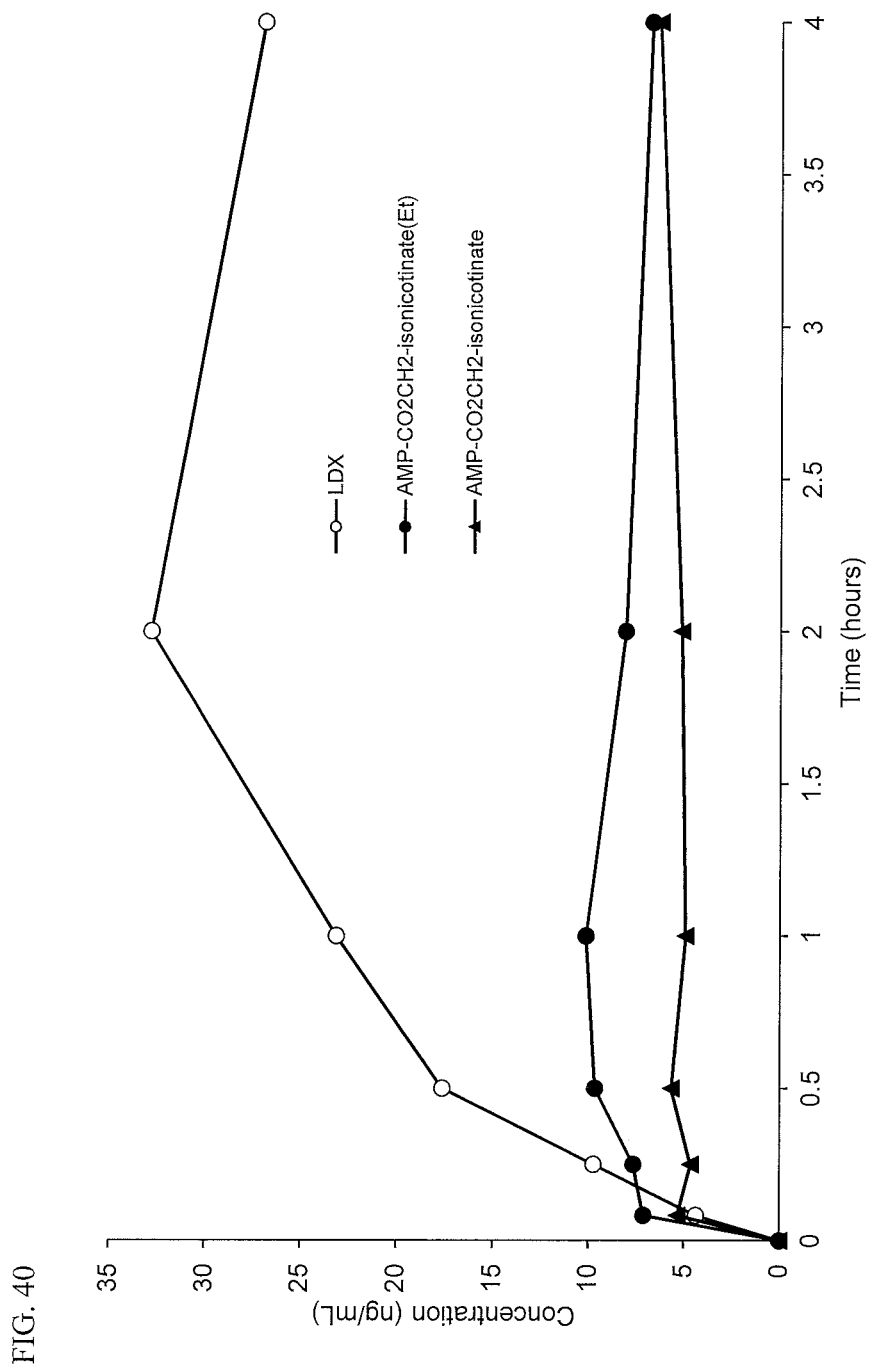
FIG. 40 Intranasal PK curves comparing lisdexamfetamine (LDX), d-amphetamine-CO₂CH₂-isonicotinate ethyl ester (AMP-CO₂CH₂-isonicotinate(Et)), and d-amphetamine-CO₂CH₂-isonicotinate (AMP-CO₂CH₂-isonicotinate).

FIG. 30-32 illustrate that some compounds of the present invention containing an isonicotinoyl moiety unexpectedly and non-obviously result in different and/or improved d-amphetamine exposure following oral, intranasal, and/or intravenous administration in a subject when compared to a compound of the same structure but with the isonicotinoyl replaced by a nicotinoyl moiety. For example, FIG. 30 illustrates that d-amphetamine-CO$_2$CH$_2$-isonicotinoyl-Ser provides increased oral bioavailability of d-amphetamine compared to d-amphetamine-CO$_2$CH$_2$-nicotinoyl-Ser. FIG. 31 illustrates that AMP-CO$_2$CH$_2$-isonicotinate(Et) decreases exposure to d-amphetamine after intranasal administration when compared to AMP-CO$_2$CH$_2$-nicotinate (Et). FIG. 32 illustrates that AMP-CO$_2$CH$_2$-isonicotinoyl-Val-NH$_2$ decreases exposure to d-amphetamine after intravenous administration when compared to AMP-CO$_2$CH$_2$-nicotinoyl-Val-NH$_2$.

Further aspects and embodiments of the present technology are described in the following paragraphs.

Some aspects of the present invention include a compound having the structure of Formula I:

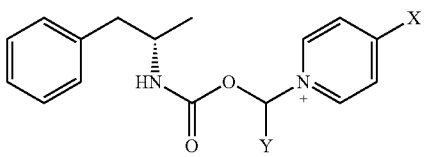

or a pharmaceutically acceptable salt of said compound, where X is selected from the group consisting of esters, carboxylic acids, amino acids, amino acid residues, amides, and derivatives thereof, and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle. In another aspect is a composition comprising said compound or pharmaceutically acceptable salt of the compound.

Another aspect includes a compound having the structure of Formula IA or the pharmaceutically acceptable salt of said compound:

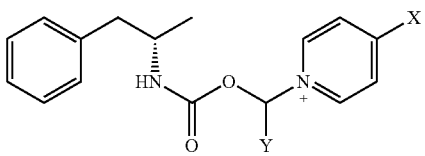

where X is A-COO—R; where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. In another aspect is a composition comprising said compound or pharmaceutically acceptable salt of the compound.

Another aspect is a compound having the structure of Formula IC or the pharmaceutically acceptable salt of said compound:

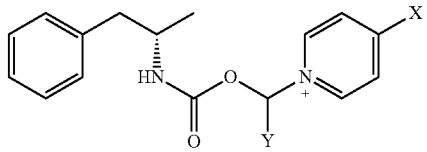

where X is A-CO—NR$^1$R$^2$; where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R$^1$ and R$^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. In another aspect is a composition comprising said compound or pharmaceutically acceptable salt of the compound.

Another aspect is a compound or the pharmaceutically acceptable salt of said compound, wherein A is absent, Y is hydrogen, and the compound has the structure of formula IIA:

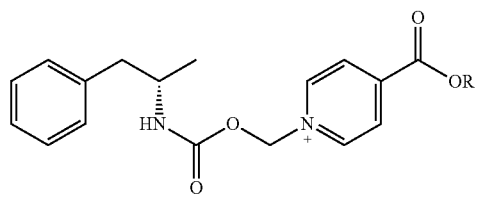

where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. In another aspect is a composition comprising said compound or pharmaceutically acceptable salt of the compound.

Another aspect is a compound the pharmaceutically acceptable salt of said compound, wherein A is absent, Y is hydrogen, and the compound has the structure of Formula IIC:

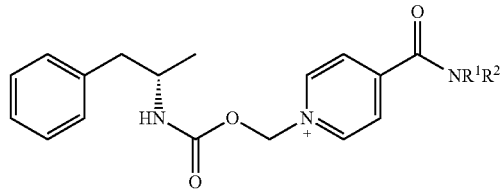

where R$^1$ and R$^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. In another aspect is a composition comprising said compound or pharmaceutically acceptable salt of the compound.

In one aspect, the compound has a structure selected from the group consisting of:
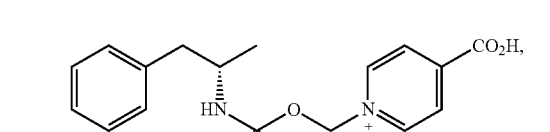
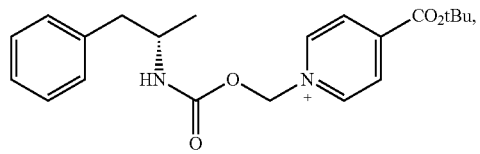
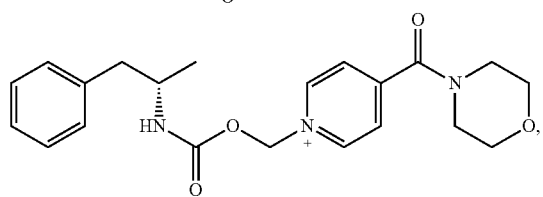
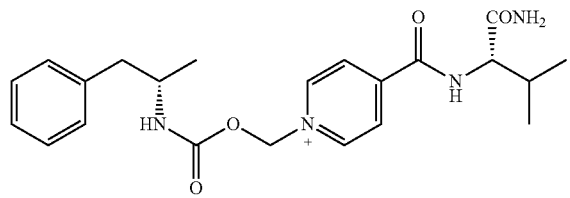
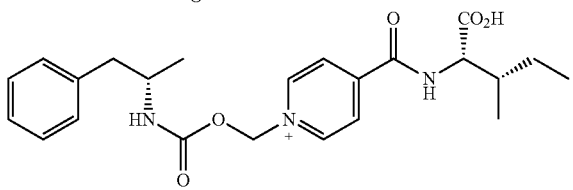
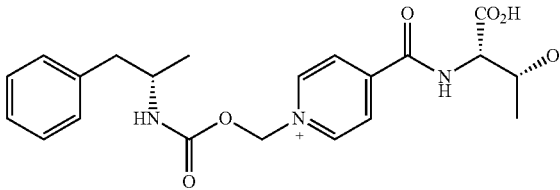
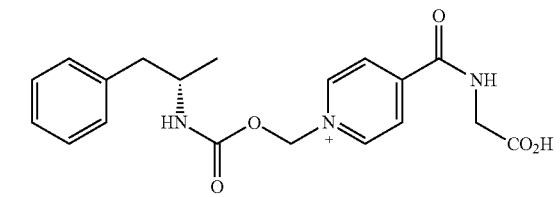
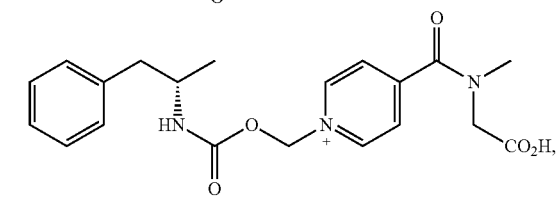
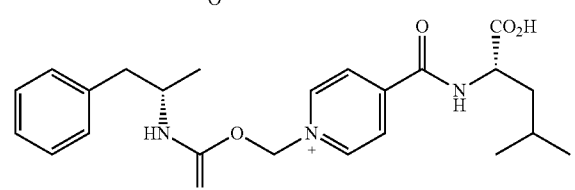
-continued
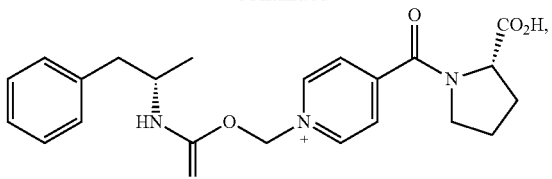
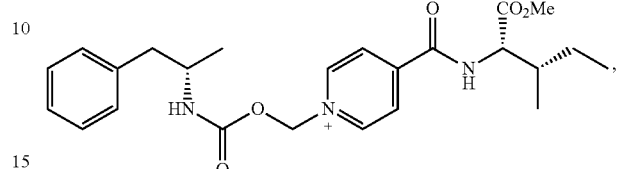
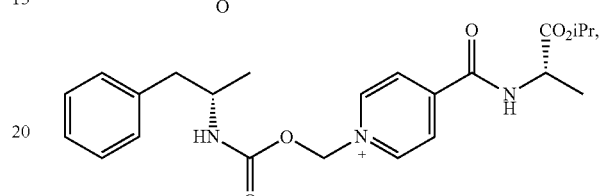
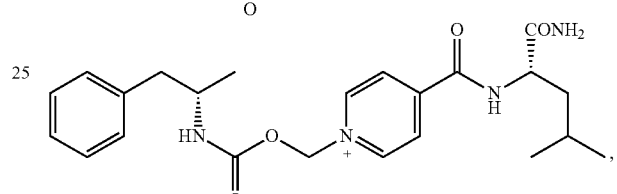
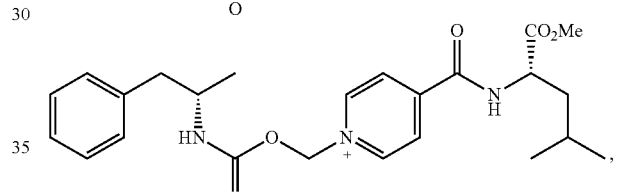
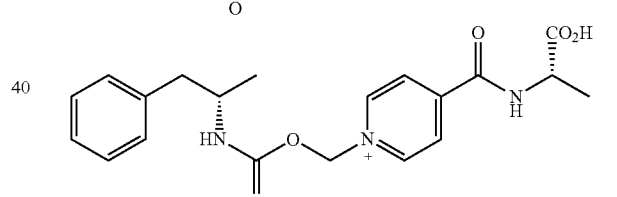
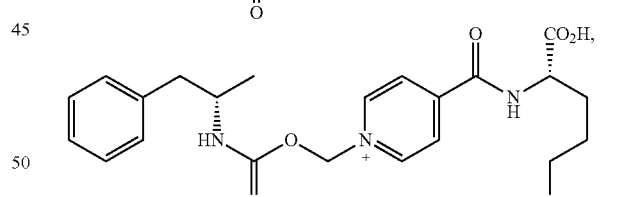
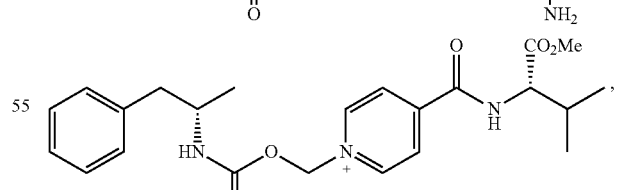
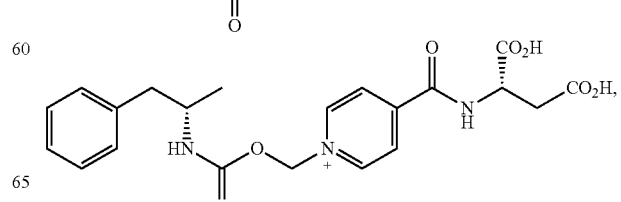

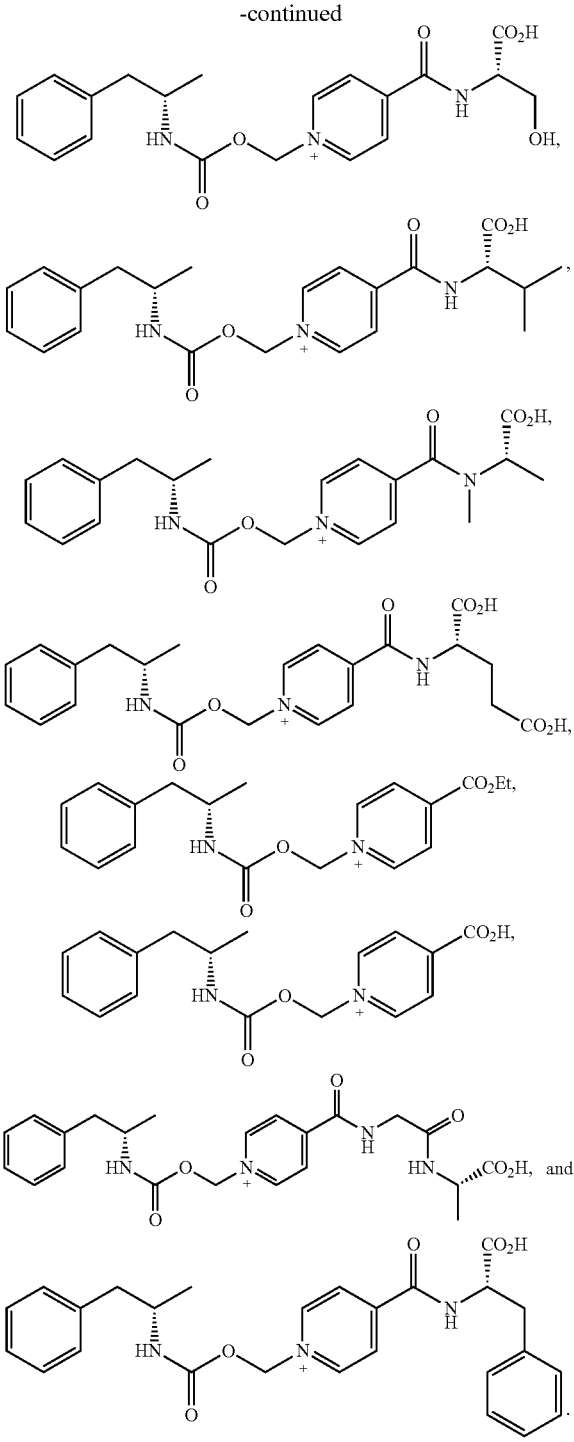

In another aspect is a composition comprising said compound or pharmaceutically acceptable salt of the compound.

In another aspect, the pharmaceutically acceptable salt of any of the compounds is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

In another aspect, the compound has a structure selected from the group consisting of:

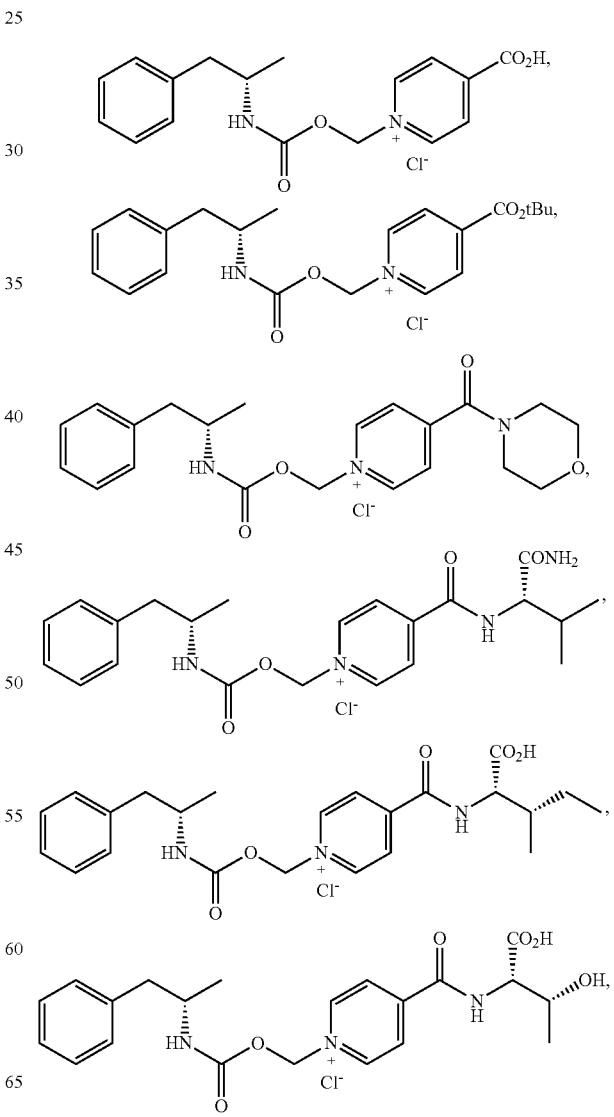

89
-continued
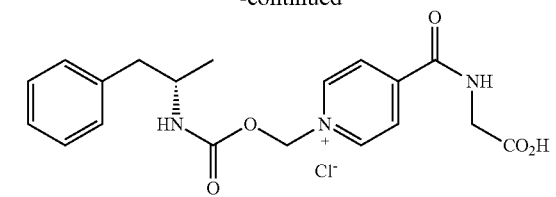
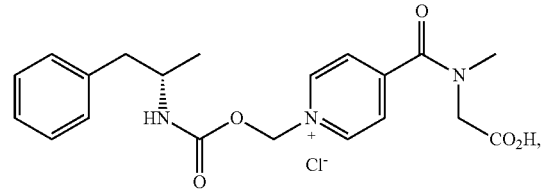
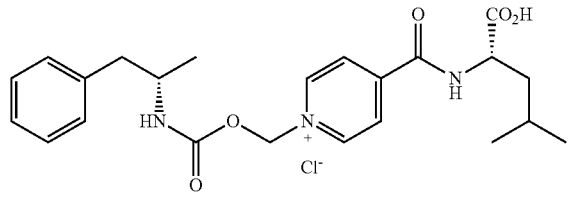
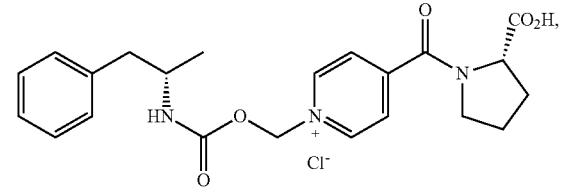
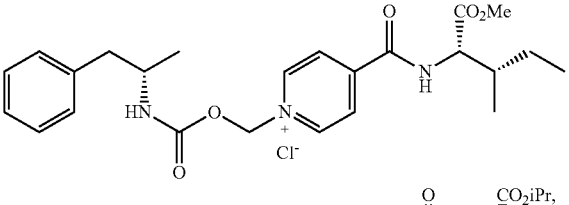
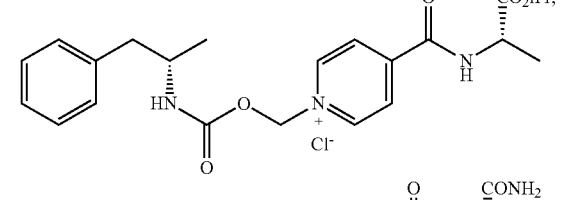
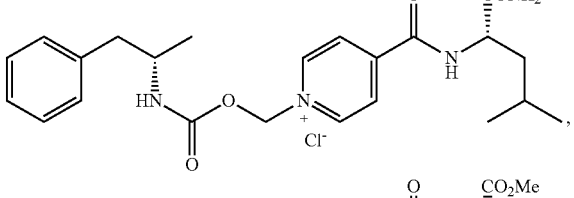
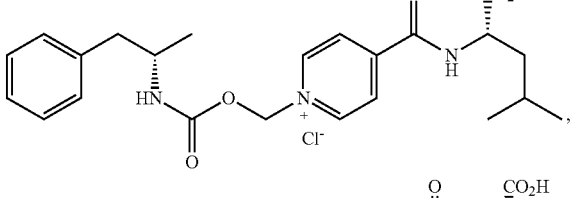
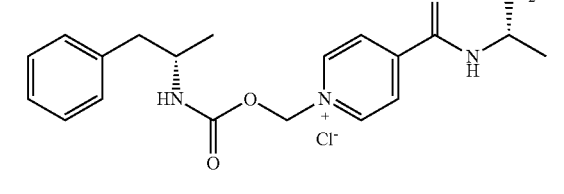
90
-continued
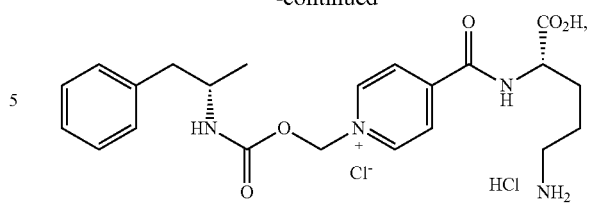
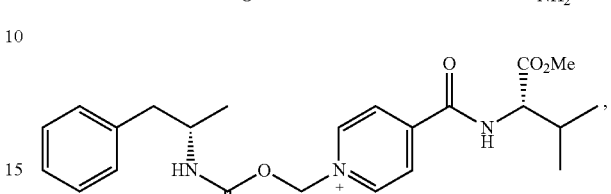
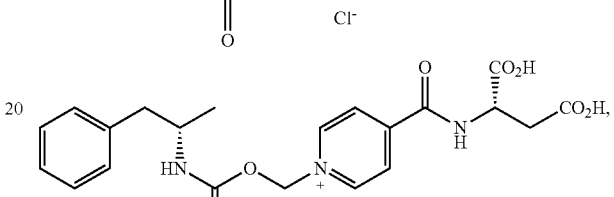
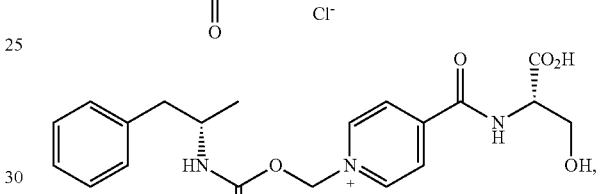
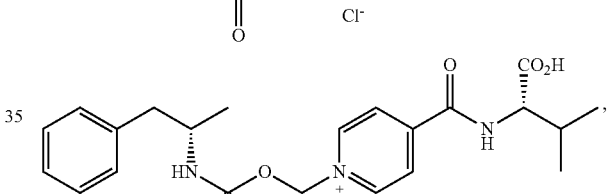
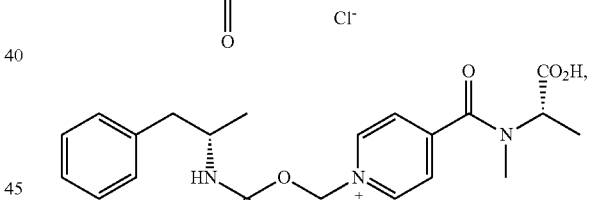
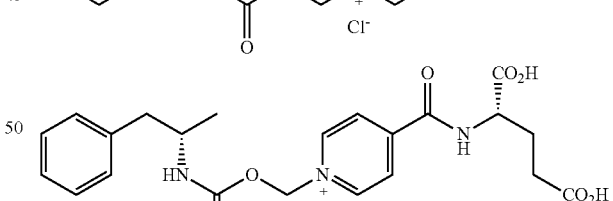
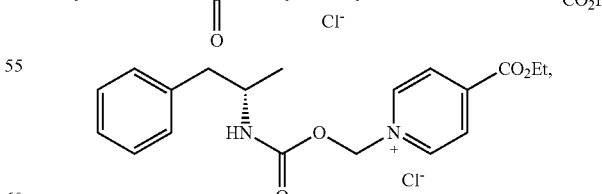
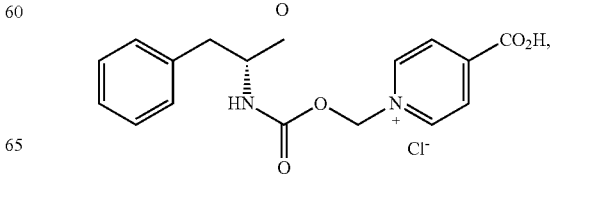

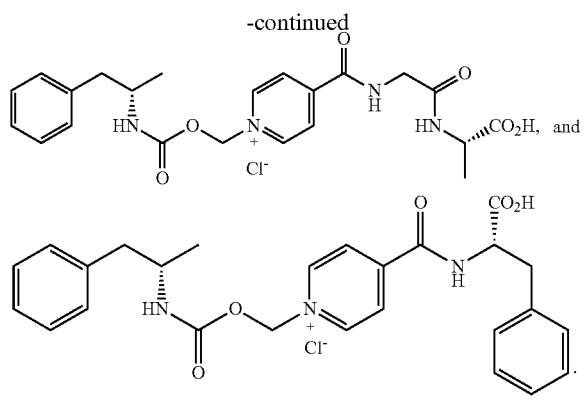

In another aspect is a composition comprising said compound or pharmaceutically acceptable salt of the compound.

In an another aspect, composition is formulated for oral administration or suppository administration. In a further aspect, the composition formulated for oral administration is in a dosage form selected from the group consisting of solid form, a tablet, a capsule, a caplet, a soft gel, a suppository, a troche, a lozenge, an oral powder, a solution, a syrup, an oral film, a thin strip, a slurry, an emulsion, an elixir, and a suspension. In yet a further aspect, the composition further comprises one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof. In a further aspect, the binder is selected from the group consisting of hydroxypropylmethyl cellulose, ethyl cellulose, povidone, acrylic and methacrylic acid co-polymers, pharmaceutical glaze, gums, and milk derivatives.

In another aspect, the compound present in an amount per unit dose of between about 0.1 mg and about 2000 mg per unit dose. In a further aspect, the compound is present in an amount per unit dose of between about 0.5 mg and about 500 mg per unit dose. In yet a further aspect, the compound is present in an amount per unit dose of between about 1 mg and about 250 mg per unit dose. In a further aspect, the compound is present in an amount per unit dose of between about 1.5 mg and about 100 mg per unit dose.

In another aspect, the composition further comprises one or more additional pharmacological substance selected from the group consisting of stimulants, anti-depressants, combinations thereof and prodrugs thereof. In another aspect, the composition further comprises one or more of methylphenidate, aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, ziprasidone, or one or more of additional amphetamine, or any combination of the foregoing. In a further aspect, the one or more additional amphetamine is unconjugated amphetamine, a conjugate of amphetamine, a prodrug of amphetamine, any isomer thereof, or any combination thereof. In another aspect, the isomer of unconjugated amphetamine is unconjugated d-amphetamine. In yet another aspect, the methylphenidate is unconjugated methylphenidate, a conjugate of methylphenidate, a prodrug of methylphenidate, any isomer thereof, or any combination thereof. In a further aspect, the isomer of unconjugated methylphenidate is unconjugated d-methylphenidate. In yet another aspect, the conjugate of methylphenidate is serdexmethylphenidate.

In one aspect, the compound is provided in an amount sufficient to provide a similar or decreased AUC when compared to unconjugated d-amphetamine when orally administered at equimolar doses. In another aspect, the compound is provided in an amount sufficient to provide a similar or decreased $C_{max}$ as compared to unconjugated d-amphetamine when administered orally at equimolar doses. In yet another aspect, the compound is provided in an amount sufficient to provide a decreased $C_{max}$ and a similar or decreased AUC as compared to unconjugated d-amphetamine when administered orally at equimolar doses. In one aspect, intranasal or intravenous administration of the at least one compound provides a decreased AUC and/or $C_{max}$ when compared to an equivalent molar amount of unconjugated d-amphetamine. In another aspect, the compound provides reduced abuse potential as compared to unconjugated d-amphetamine.

One aspect of the present invention includes a method of treating a patient having a disorder or condition requiring stimulation of the central nervous system, of treating a patient having a disease, disorder or condition mediated by controlling, preventing, limiting, or inhibiting neurotransmitter uptake, or treating a patient having a disease, disorder or condition mediated by increasing neurotransmitter concentrations in the synapse, the method comprising the step of administering to the patient in need thereof a pharmaceutically effective amount of the composition of the present invention.

In one aspect, the composition has reduced abuse potential when administered compared to unconjugated d-amphetamine. In another aspect, the disease or condition is attention-deficit hyperactivity disorder, attention deficit disorder, autistic spectrum disorder, autism, Asperger's disorder, pervasive developmental disorder, sleep disorder, obesity, depression, bipolar disorder, eating disorder, chronic fatigue syndrome, insomnia, schizophrenia, major depressive disorder, narcolepsy, postural orthostatic tachycardia syndrome, Tourette syndrome, nervous tics, substance use disorder, lethargy, depression, neural insult or obesity.

One aspect of the present invention is a kit comprising individual doses of a therapeutically effective amount of a composition comprising any compound of the present invention, a pharmaceutical salt thereof, or a combination thereof.

One aspect of the present invention is a compound having the structure of Formula I:

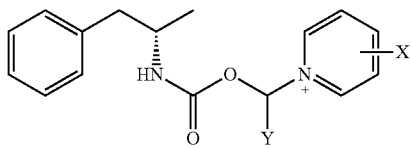

or a pharmaceutically acceptable salt of the compound, where X is selected from the group consisting of esters, carboxylic acids, amino acids, amino acid residues, amides, and derivatives thereof, and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle.

In another aspect, the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

In another aspect, X is located at the C-2 or C-4 position of the pyridine ring. In another aspect, X is located at two or more of the C-2, C-3, C-4, C-5, or C-6 position of the pyridine ring. In yet another aspect, the compound has the structure of

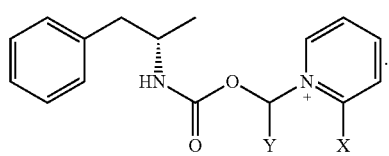

In a further aspect, the compound has the structure of

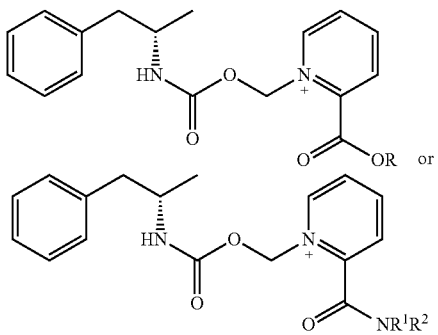

wherein where R, $R^1$, or $R^2$ is independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol. In yet another aspect, the compound has a structure of

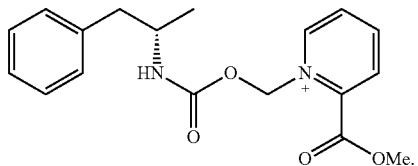

The presently described technology is now described in such full, clear, concise and exact terms as to enable any person skilled in the art to which it pertains, to practice the same. It is to be understood that the foregoing describes preferred aspects of the invention and that modifications may be made therein without departing from the spirit or scope of the invention.

The invention claimed is:

1. A compound having the structure of Formula I:

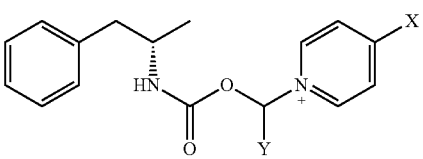

or a pharmaceutically acceptable salt of said compound,
where X is selected from the group consisting of esters, carboxylic acids, amino acids, amino acid residues, amides, and derivatives thereof,
and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle.

2. The compound of claim 1 having the structure of Formula IA or the pharmaceutically acceptable salt of said compound:

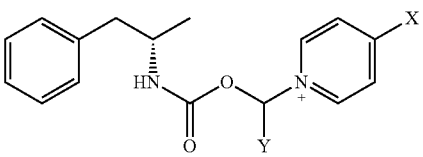

where X is A-COO—R;
where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

3. The compound of claim 1 having the structure of Formula IC or the pharmaceutically acceptable salt of said compound:

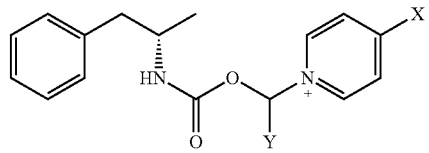

where X is A-CO—NR$^1$R$^2$;

where A is either absent or, when present, is selected from the group consisting of alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol; and where R$^1$ and R$^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

4. The compound of claim 2 or the pharmaceutically acceptable salt of said compound, wherein A is absent, Y is hydrogen, and the compound has the structure of formula IIA:

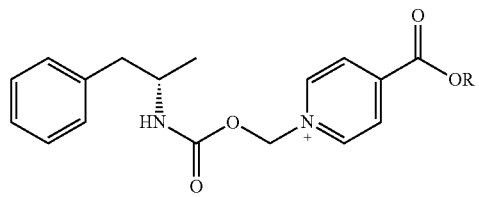

where R is selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

5. The compound of claim 3 or the pharmaceutically acceptable salt of said compound, wherein A is absent, Y is hydrogen, and the compound has the structure of Formula IIC:

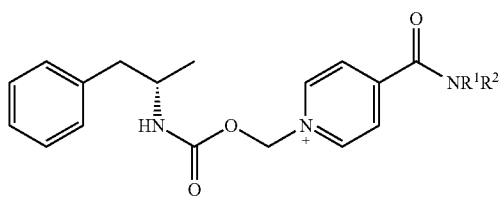

where $R^1$ and $R^2$ are independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

6. A compound having a structure selected from the group consisting of:

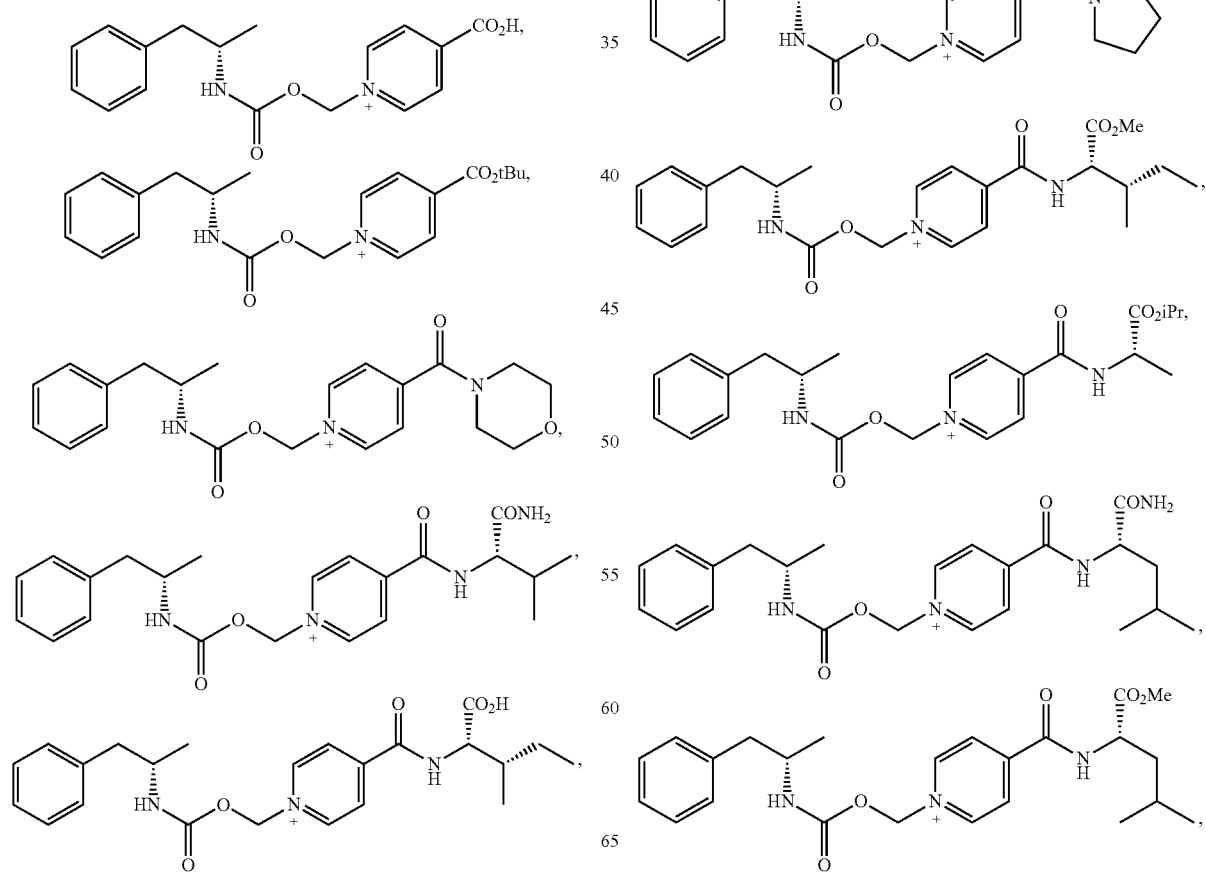

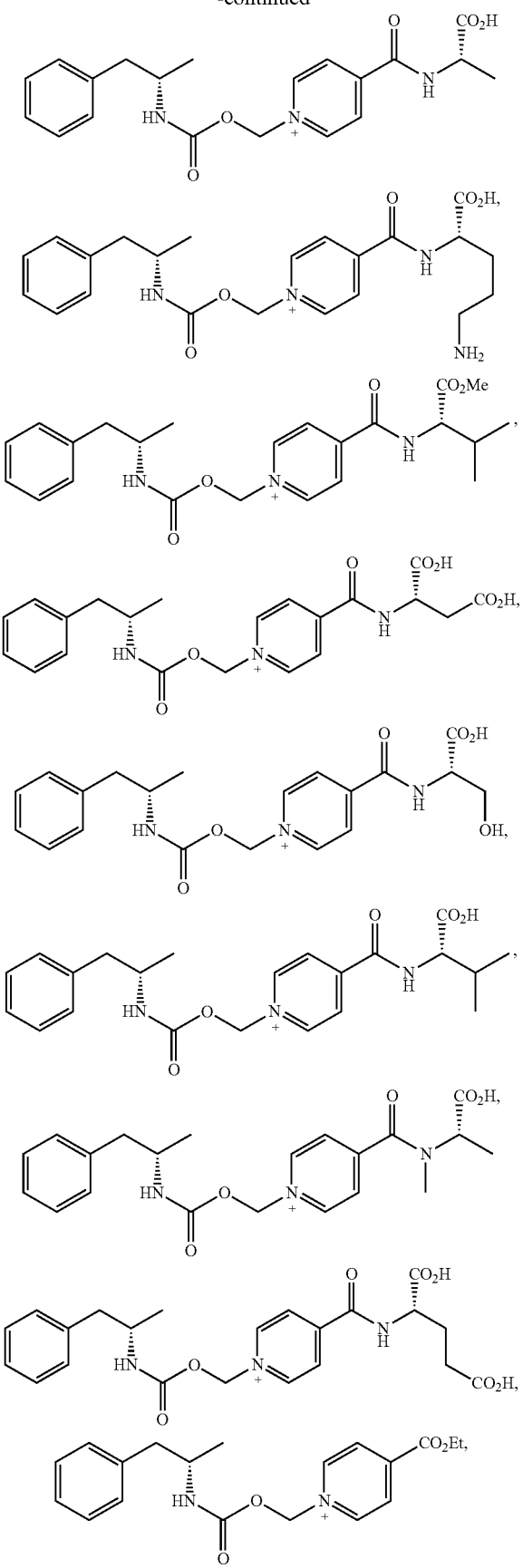

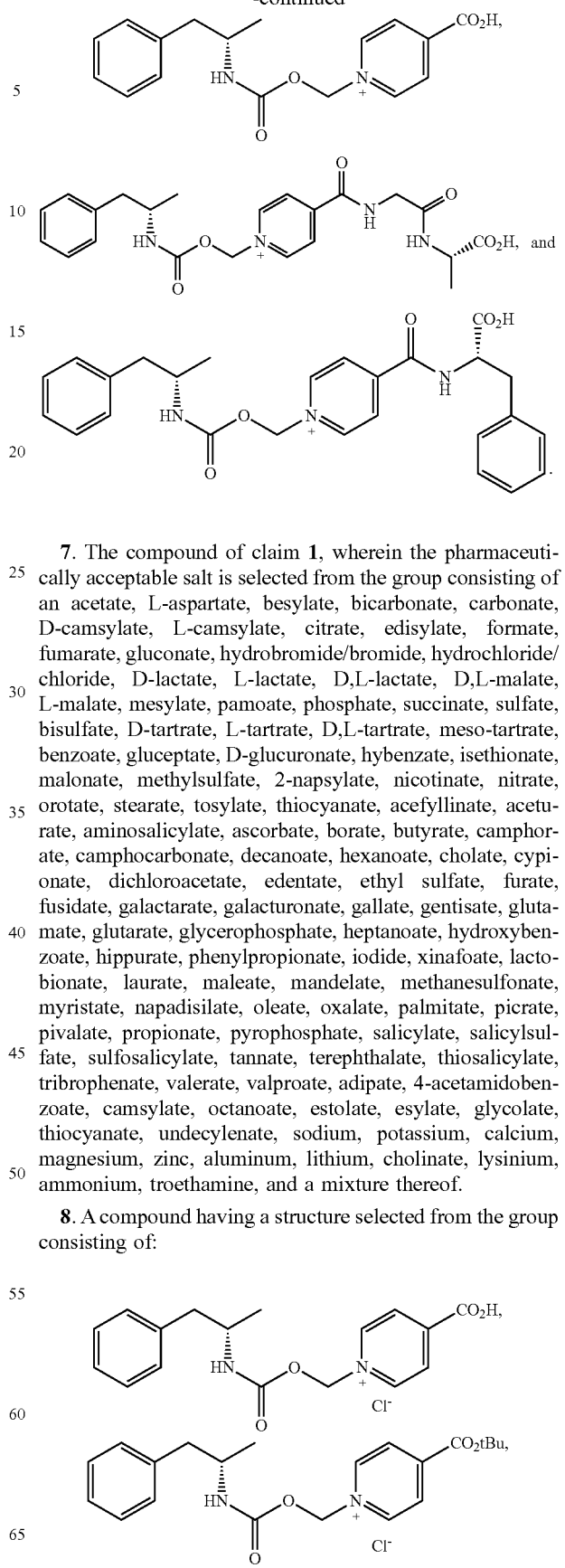

7. The compound of claim 1, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

8. A compound having a structure selected from the group consisting of:

101
-continued

102
-continued

-continued

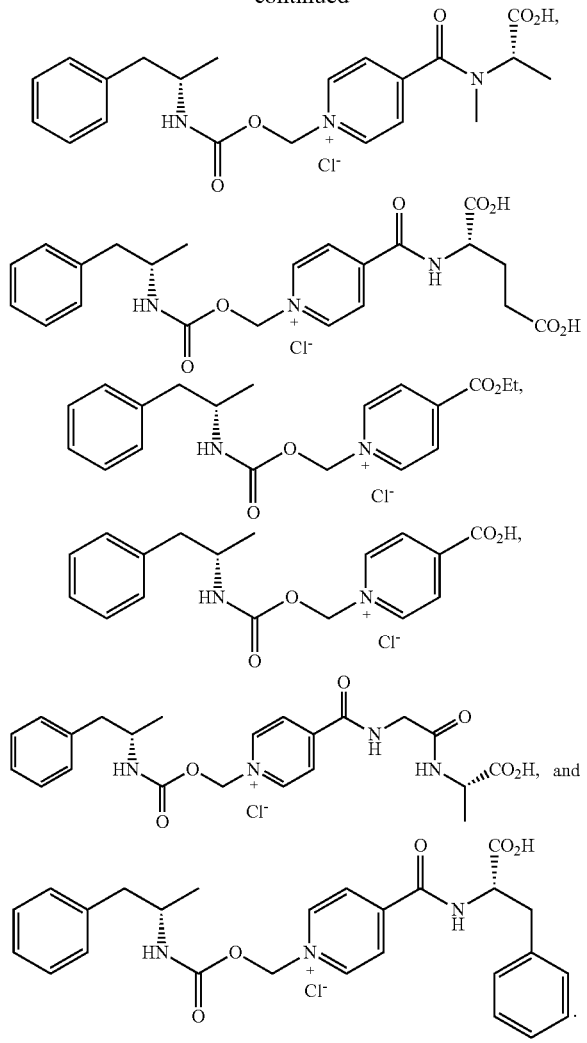

9. A composition comprising the compound of claim 1 or pharmaceutically acceptable salt of the compound.

10. The composition of claim 9, wherein the composition is formulated for oral administration or suppository administration.

11. The composition of claim 10, wherein the composition formulated for oral administration is in a dosage form selected from the group consisting of solid form, a tablet, a capsule, a caplet, a soft gel, a suppository, a troche, a lozenge, an oral powder, a solution, a syrup, an oral film, a thin strip, a slurry, an emulsion, an elixir, and a suspension.

12. The composition of claim 10, wherein the composition further comprises one or more excipients, wherein the excipients are selected from the group consisting of antiadherents, binders, coatings, disintegrants, fillers, flavors, dyes, colors, glidants, lubricants, preservatives, sorbents, sweeteners, and combinations thereof.

13. The composition of claim 12 wherein the binder is selected from the group consisting of hydroxypropylmethyl cellulose, ethyl cellulose, povidone, acrylic and methacrylic acid co-polymers, pharmaceutical glaze, gums, milk derivatives, and combinations thereof.

14. The composition of claim 9, wherein the compound present in an amount per unit dose of between about 0.1 mg and about 2000 mg per unit dose.

15. The composition of claim 13, wherein the compound is present in an amount per unit dose of between about 0.5 mg and about 500 mg per unit dose.

16. The composition of claim 15, wherein the compound is present in an amount per unit dose of between about 1 mg and about 250 mg per unit dose.

17. The composition of claim 16, wherein the compound is present in an amount per unit dose of between about 1.5 mg and about 100 mg per unit dose.

18. The composition of claim 9, wherein the composition further comprises one or more additional pharmacological substance selected from the group consisting of stimulants, anti-depressants, combinations thereof, and prodrugs thereof.

19. The composition of claim 9, wherein the composition further comprises one or more of methylphenidate, aripiprazole, atomoxetine, baclofen, clonidine, desipramine, dihydrotetrabenazine, guanfacine, haloperidol, levetiracetam, mecamylamine, etoclopramide, olanzapine, ondansetron, pergolide, pimozide, pramipexole, risperidone, selegiline, sulpiride, tetrabenazine, topiramate, ziprasidone, or one or more of additional amphetamine, or any combination thereof.

20. The composition of claim 19, wherein the one or more additional amphetamine is unconjugated amphetamine, a conjugate of amphetamine, a prodrug of amphetamine, any isomer thereof, or any combination thereof.

21. The composition of claim 20, wherein the isomer of unconjugated amphetamine is unconjugated d-amphetamine.

22. The composition of claim 19, wherein the methylphenidate is unconjugated methylphenidate, a conjugate of methylphenidate, a prodrug of methylphenidate, any isomer thereof, or any combination thereof.

23. The composition of claim 22, wherein the isomer of unconjugated methylphenidate is unconjugated d-methylphenidate.

24. The composition of claim 22, wherein the conjugate of methylphenidate is serdexmethylphenidate.

25. The composition of claim 9, wherein the compound is provided in an amount sufficient to provide a similar or decreased AUC when compared to unconjugated d-amphetamine when orally administered at equimolar doses.

26. The composition of claim 9, wherein the compound is provided in an amount sufficient to provide a similar or decreased $C_{max}$ as compared to unconjugated d-amphetamine when administered orally at equimolar doses.

27. The composition of claim 9, wherein the compound is provided in an amount sufficient to provide a decreased $C_{max}$ and a similar or decreased AUC as compared to unconjugated d-amphetamine when administered orally at equimolar doses.

28. The composition of claim 9, wherein intranasal or intravenous administration of the compound provides a decreased AUC and/or $C_{max}$ when compared to an equivalent molar amount of unconjugated d-amphetamine.

29. The composition of claim 9, wherein the compound provides reduced abuse potential as compared to unconjugated d-amphetamine.

30. A kit comprising individual doses of a therapeutically effective amount of a composition comprising the compound of claim 1, a pharmaceutical salt thereof, or a combination thereof.

31. A compound having the structure of Formula I:

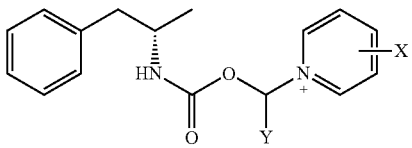

or a pharmaceutically acceptable salt of the compound, where X is selected from the group consisting of esters, carboxylic acids, amino acids, amino acid residues, amides, and derivatives thereof, wherein X is located at the C-2 or C-4 position of the pyridine ring or X is located at two or more of the C-2, C-3, C-4, C-5, or C-6 positions of the pyridine ring, and Y is selected from the group consisting of hydrogen, alkenyl, alkoxy, alkyl, alkynyl, aryl, substituted aryl, alkylaryl, cycloalkenyl, cycloalkyl, cycloalkynyl, heteroalkyl, heteroaryl, and heterocycle.

32. The compound of claim 31, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

33. The compound of 31, wherein the compound has the structure of

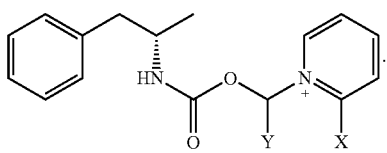

34. The compound of claim 33, wherein the compound has the structure of

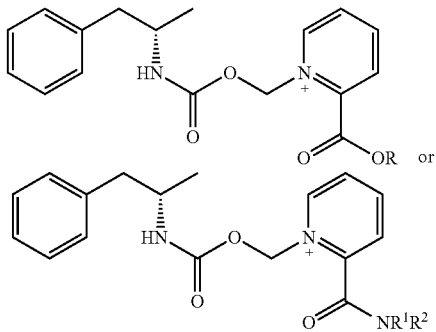

wherein where R, $R^1$, or $R^2$ is independently selected from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, polycycloalkenyl, polycycloalkenylalkyl, polycycloalkyl, polycycloalkylalkyl, and polyethylene glycol.

35. The compound of claim 34, wherein the compound has a structure of

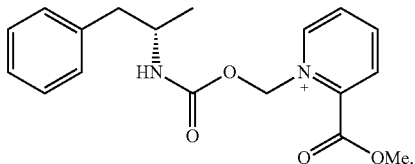

36. A kit comprising individual doses of a therapeutically effective amount of a composition comprising at least one compound of claim 6, a pharmaceutical salt thereof, or a combination thereof.

37. A kit comprising individual doses of a therapeutically effective amount of a composition comprising at least one compound of claim 8.

38. A kit comprising individual doses of a therapeutically effective amount of a composition comprising the compound of claim 31, a pharmaceutical salt thereof, or a combination thereof.

* * * * *